United States Patent [19]
Jacobson et al.

[11] Patent Number: 5,861,405
[45] Date of Patent: Jan. 19, 1999

[54] S-SUBSTITUTED 1,3,7-TRIALKYL-XANTHINE DERIVATIVES

[75] Inventors: Kenneth A. Jacobson, Silver Spring, Md.; Yishai Karton, Nes Zionz, Israel; Carola Gallo-Rodriguez, Rockville, Md.; Bilha Fischer, Silver Spring, Md.; Philip J. M. van Galen, Rockville, Md.; Michel Maillard, Cambridge, Mass.

[73] Assignee: The United States of America as represented by the Department of Health and Human Services, Washington, D.C.

[21] Appl. No.: 335,108

[22] Filed: Nov. 7, 1994

Related U.S. Application Data

[63] Continuation of Ser. No. 57,086, May 3, 1993, abandoned.

[51] Int. Cl.$^6$ ..................... C07D 473/12; C07D 473/06; A61K 31/52
[52] U.S. Cl. .................... 514/263; 544/229; 544/267; 544/271; 544/272; 544/273
[58] Field of Search .................... 544/267, 271, 544/272, 273, 224; 514/263

[56] References Cited

U.S. PATENT DOCUMENTS

| | | | |
|---|---|---|---|
| 2,840,559 | 6/1958 | Krantz, Jr. et al. | 544/273 |
| 3,309,271 | 3/1967 | Georges et al. | 167/55 |
| 3,624,215 | 11/1971 | Stein | 424/253 |
| 3,624,216 | 11/1991 | Stein | 424/253 |
| 3,641,010 | 2/1972 | Schweiss et al. | 544/273 |
| 4,120,947 | 10/1978 | Diamond | 514/263 |
| 4,297,494 | 10/1981 | Groman et al. | 544/267 |
| 4,299,832 | 11/1981 | Brown et al. | 544/267 |
| 4,397,779 | 8/1983 | Groman et al. | 544/267 |
| 4,546,182 | 10/1985 | Kjellin et al. | 544/273 |
| 4,548,820 | 10/1985 | Regnier et al. | 544/267 |
| 4,558,051 | 12/1985 | Sunshine et al. | 514/264 |
| 4,567,183 | 1/1986 | Sunshine et al. | 514/264 |
| 4,593,095 | 6/1986 | Snyder et al. | 514/263 |
| 4,612,315 | 9/1986 | Jacobson et al. | 544/269 |
| 4,696,932 | 9/1987 | Jacobson et al. | 544/271 |
| 4,755,517 | 7/1988 | Bruns et al. | 544/272 |
| 4,769,377 | 9/1988 | Snyder et al. | 544/267 |
| 4,783,530 | 11/1988 | Rzeszotarski et al. | 544/272 |
| 4,879,296 | 11/1989 | Daluge et al. | 544/270 |
| 4,883,801 | 11/1989 | Nathanson | 514/263 |
| 4,904,472 | 2/1990 | Belardinelli et al. | 514/263 |
| 4,981,857 | 1/1991 | Daluge et al. | 514/263 |
| 5,015,647 | 5/1991 | Daluge et al. | 514/263 |
| 5,047,534 | 9/1991 | Peet et al. | 514/263 |
| 5,175,291 | 12/1992 | Kufner-Muhl | 514/263 |
| 5,270,316 | 12/1993 | Suzuki | 544/273 |

FOREIGN PATENT DOCUMENTS

| | | |
|---|---|---|
| 0 215 736 | 3/1987 | European Pat. Off. . |
| 565377 | 10/1993 | European Pat. Off. . |
| 590919 | 4/1996 | European Pat. Off. . |
| WO 92/06976 | 4/1992 | WIPO . |
| 94/01114 | 1/1994 | WIPO . |
| 94/03456 | 2/1994 | WIPO . |

OTHER PUBLICATIONS

Jacobson et al., "8–(3–Chlorostyryl)caffeine (CSC) Is a Selective $A_2$–Adenosine Antagonist In Vitro and In Vivo," *FEBS Letters*, 323 (1,2), 141–144 (May 1993).
Jackson et al., *J. Pharmacol. Exper. Therapeut.*, 267, 1304–1310 (1993).
Jacobson et al., *FEBS Lett.*, 323, 141–144 (1993).
Jacobson et al., *Chem. Abstr.*, 119:159968u (1993).
Ji et al., *Drug Development Research*, 29, 292–298 (1993).
Kanda et al., *Eur. J. Pharmacol.*, 256, 263–268 (1994).
Baumgold et al., "Penetration of Adenosine Antagonists into Mouse Brain as Determined by Ex Vivo Binding," *Biochemical Pharmacology*, 43(4), 889–894 (1992).
Bruns et al., "Characterization of the $A_2$ Adenosine Receptor Labeled by [$^3$H] NECA in Rat Striatal Membranes," *Molecular Pharmacology*, 29, 331–346 (1986).

(List continued on next page.)

*Primary Examiner*—Mark L. Berch
*Attorney, Agent, or Firm*—Leydig, Voit, & Mayer, Ltd.

[57] ABSTRACT

The present invention provides 8-substituted 1,3,7-trialkylxanthines useful as $A_2$-selective adenosine receptor antagonists and compositions comprising such compounds. Examples of the 8-substituted 1,3,7-trialkyl xanthines include:

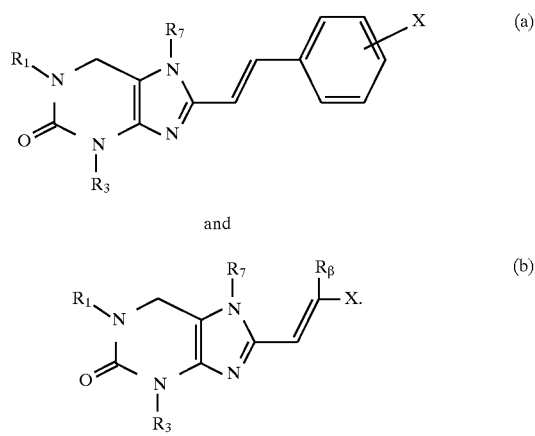

In compound (a), $R_1$, $R_3$, and $R_7$ are methyl and X is one to three substituents, which may be the same or different and selected from the group consisting of amino, $C_1$–$C_4$ alkylcarbonylamino, carboxy $C_2$–$C_4$ alkylcarbonylamino, halo, $C_1$–$C_3$ alkyloxy, amino $C_1$–$C_4$ alkyloxy, $C_1$–$C_4$ alkyloxy carbonylamino, amino $C_1$–$C_4$ alkenyloxy, isothiocyanato, and diazonium tetrafluoroborate. In compound (b), $R_1$, $R_3$, and $R_7$ are methyl, $R_\beta$ is hydrogen or methyl, and X is selected from the group consisting of R, C(=O)OR, and C(=O)NH—R, wherein R is a $C_1$–$C_6$ alkyl.

28 Claims, 18 Drawing Sheets

OTHER PUBLICATIONS

Bruns, "Adenosine Receptors in Brain Membranes: Binding of $N^6$-cyclohexyl [$^3$H] adenosine and 1,3-diethyl-8-[$^3$H] phenylxanthine," *Proc. Natl. Acad. Sci. USA,* 77(9), 5547–5551 (1980).

Bruns, "Adenosine Antagonism by Purines, Pteridines and Benzopteridines in Human Fibroblasts," *Biochemical Pharmacology,* 30, 325–333 (1981).

Cheng et al., "Relationship Between the Inhibition Constant ($K_1$) and the Concentration of Inhibitor Which Causes 50 Per Cent Inhibition ($I_{50}$) of an Enzymatic Reaction," *Biochem. Pharmacol.,* 22, 3099–3108 (1973).

Daly, "Adeosine Receptors: Targets for Future Drugs," *J. Medicinal Chemistry,* 25(3), 197–207 (1982).

Daly et al., "Caffeine Analogs: Sructure–Activity Relationships at Adenosine Receptors," *Pharmacology,* 42, 309–321 (1991).

Erickson et al., "1,3,8–Trisubstituted Xanthines. Effects of Substitution Pattern upon Adenosine Receptor $A_1/A_2$ Affinity," *J. Med. Chem.,* 34, 1431–1435 (1991).

Ferrë et al., "Adenosine–Dopamine Interactions in the Brain," *Neuroscience,* 51(3), 501–512 (1992).

Francis et al., "Structure–Activity Profile of a Series of Novel Triazoloquinazoline Adenosine Antagonists," *J. Med. Chem.,* 31, 1014–1020 (1988).

Griebel et al., "Behavioural Effects of Selective $A_2$ Adenosine Receptor Antagonists, CGS 21197 and CGS 22706, in Mice." *NeuroReport,* 2, 139–140 (1991).

Jacobson et al., "Xanthine Functionalized Congeners as Potent Ligans at $A_2$–Adenosine Receptors," *J. Med. Chem.,* 30, 211–214 (1987).

Jacobson et al., "Agonist Derived Molecular Probes for $A_2$ Adenosine Receptors," *J. Molecular Recognition,* 2(4), 170–178 (1989).

Jacobson et al., "Electrophilic Derivatives of Purines as Irreversible Inhibitors of $A_1$ Adenosine Receptors," *J. Med. Chem.,* 32 1043–1051 (1989).

Jacobson et al., "Adenosine Receptors: Pharmacology, Structure–Activity Relationships, and Therapeutic Potential," *J. Med. Chem.,* 35, 407–422 (1992).

Jacobson et al., "Chemical Modification and Irreversible Inhibition of Striatal $A_{2a}$ Adenosine Receptors," *Molecular Pharmacology,* 42, 123–133 (1992).

Jarvis et al., "[$^3$H] CGS 21680, A Selective $A_2$ Adenosine Receptor Agonist Directly Labels $A_2$ Receptors in Rat Brain," *J. Pharmacol. Exp. Therap.* 251, 888–893 (1989).

Lohse et al., "Separation of Solubilized $A_2$ Adenosine Receptors of Human Platelets from Non–Receptor [$^3$H] NECA Binding Sites by Gel Filtration," *Naunyn Schmiedeberg's Archives of Pharmacology,* 337, 64–68 (1988).

Nikodijevic et al., "Behavioral Effects of $A_1$–and $A_2$–Selective Adenosine Agonists and Antagonists: Evidence for Synergism and Antagonism," *J. Pharmacology,* 259(1), 286–294 (1991).

Sarges et al., "4–Amino [1,2,4] triazolo[4,3–a] quinoxalines. A Novel Class of Potent Adenosine Receptor Antagonists and Potential Rapid–Onset Antidepressants," *J. Med. Chem.,* 33, 2240–2254 (1990).

Schiffmann et al., "Adenosine $A_{2a}$ Receptor Expression in Stariatal Neurons: Implications for Basal Ganglia Pathophysiology," *Drug Development Research,* 28, 381–385 (1993).

Schwabe et al., "Characterization of Adenosine Receptors in Rat Brain by (-) [$^3$H] $N^6$–Phenylisopropyladenosine," *Naunyn Schmiedeberg's Arch. Pharmacology,* 313, 179–187 (1980).

Shamim et al., "Effects of 8–Phenyl and 8–Cycloalkyl Substituents on the Activity of Mono–, Di–, and Trisubstituted Alkylxanthines with Substitution at the 1–, 3–, and 7–Positions," *J. Med. Chem.,* 32, 1231–1237 (1989).

Shimada et al., "(E)–1,3–Dialkyl–7–methyl–8–(3,4,5–trimethoxy–styry)xanthines: Potent and Selective Adenosine $A_2$ Antagonists," *J. Med. Chem.,* 35, 2342–2345 (1992).

Snyder et al., "Adenosine Receptors and Behavioral Actions of Methylxanthines," *Proc. Natl. Acad. Sci. USA.,* 78(5), 3260–3264 (1981).

Stehle et al., "Molecular Cloning and Expression of the cDNA for A Novel $A_2$–Adenosine Receptor Subtype," *Mol. Endocrinol.,* 6, 384–393 (1992).

Stone et al., "Species Differences in High–Affinity Adenosine $A_2$ Binding Sites in Striatal Membranes from Mammalian Brain," *Drug Development Research,* 15, 31–46 (1988).

Ueeda et al., "2–Aralkoxyadenosines: Potent and Selective Agonists at the Coronary Artery $A_2$ Adenosine Receptor," *J. Med. Chem.,* 34, 1340–1344 (1991).

Ueno et al., "$A_1$ and $A_2$ Adenosine Receptor Regulation of Erythropoietin Production," *Life Sciences,* 43, 229–237 (1988).

Ukena et al., "Functionalized Congeners of 1,3–Dipropyl–8–Phenylxanthine: Potent Antagonists for Adenosine Receptors that Modulate Membrane Adenylate Cyclase in Pheochromocytoma Cells, Platelets and Fat Cells," *Life Sciences,* 38, 797–807 (1986).

Ukena et al., "Analogs of Caffeine: Antagonists with Selectivity for $A_2$ Adenosine Receptors," *Life Sciences,* 39, 743–750 (1986).

Ukena et al., "Species Differences in Structure–Activity Relationships of Adenosine Agonists and Xanthine Antagonists at Brain A1 Adenosine Receptors," *FEBS Letters,* 209 (1), 122–128 (1986).

van Galen et al., "Adenosine $A_1$ and $A_2$ Receptors: Structure–Function Relationships," *Medicinal Research Reviews,* 12(5), 423–471 (1992).

Leff, *BioWorld Today* vol. 6, #7, p. 1,4 (Jan. 12, 1995).

"Goodman and Gilman's Pharmacological Basis of Therapentics, 7th Edition" (1985) p. 589, 598–601 Jacobson, Biochem. Pham. 41, 1399 (1991).

Katzung, "Basic and Clinical Pharmacology, $3^{rd}$ Edition" (1987) pp. 20–21.

Craig, BioWorld Today, Oct. 18, 1994. p 1.

8-SUBSTITUTED 1,3,7-TRIALKYL-XANTHINE DERIVATIVES

This is a continuation of application Ser. No. 08/057,086 filed on May 3, 1996 abandoned.

TECHNICAL FIELD OF THE INVENTION

The present invention relates to 8-substituted 1,3,7-trialkyl-xanthine derivatives and their use as $A_2$-selective adenosine receptor antagonists.

BACKGROUND OF THE INVENTION

Xanthine alkaloids, which include caffeine, theophylline, and theobromine, are ubiquitously distributed in plants, such as the seeds of *Coffea arabica* and related species, the leaves of *Thea sinensis*, the seeds of *Theobroma cacao*, the nuts of the tree *Cola acuminata*, and the like. Extracts of these naturally occurring substances have been used throughout history as beverages and the pharmacologically significant nervous system stimulant properties of such concoctions have long been recognized.

Xanthine, itself, is 3,7-dihydro-1H-purine-2,6-dione. Chemically, therefore, xanthine and its derivatives are structurally related to uric acid and purine. Caffeine (1,3,7-trimethylxanthine), theophylline (1,3-dimethylxanthine), and theobromine (3,7-dimethylxanthine) represent the alkaloids most frequently associated with the expression "xanthine." However, numerous other xanthine derivatives have been isolated or synthesized. See, for example, Bruns, *Biochem. Pharmacol.*, 30, 325–333 (1981), which describes more than one hundred purine bases and structurally related heterocycles with regard to adenosine antagonism, and Daly, *J. Med. Chem.*, 25(3), 197–207 (1982).

Pharmacologically, the xanthines represent an important class of therapeutic agents. Observed pharmacological actions include stimulation of the central nervous system, relaxation of smooth muscle constrictions of the smaller bronchi and other smooth muscles, dilation of the small pulmonary arteries, stimulation of cardiac muscle with increased cardiac output, and the promotion of mild diuresis. Available evidence indicates that the therapeutic actions of these drugs involve blockade or antagonism of adenosine receptors.

It now has been recognized that there are not one but at least two classes of extracellular receptors involved in the action of adenosine. One of these has a high affinity for adenosine and has been found to be coupled to a number of secondary messenger systems, including inhibition of adenylate cyclase, inhibition of calcium entry, stimulation of potassium flux, and phosphoinositide metabolism (Van Galen et al., *Medicinal Res. Rev.*, 12, 423–471 (1992)). This class has been termed by some as the $A_1$ receptors. The other class of receptors has a low affinity for adenosine and has been found to elicit a range of physiological responses, including the inhibition of platelet aggregation (Lohse et al., *Naunyn Schmiedeberg's Arch. Pharmacol.*, 337, 64–68 (1988)), dilation of blood vessels (Ueeda et al., *J. Med. Chem.*, 34, 1340–1344 (1991)), erythropoietin production (Ueno et al., *Life Sciences*, 43, 229–237 (1988)), and depression of locomotor activity (Nikodijevic et al., *J. Pharm. Exp. Therap.*, 259, 286–294 (1991)). This class has been termed the $A_2$ receptors.

Subtypes of $A_2$ receptors also have been identified. For example, $A_{2a}$ receptors, which are linked via $G_S$ guanine nucleotide binding proteins to the stimulation of adenylate cyclase, are present in high density in the striatum of the CNS. They are also present on platelets, pheochromocytoma cells, and smooth muscle cells. $A_{2b}$ receptors (Bruns et al., *Mol. Pharmacol.*, 29, 331–346 (1986)) are found in the brain, fibroblasts, and intestines (Stehle et al., *Mol. Endocrinol.*, 6, 384–393 (1992)).

Characterization of the adenosine receptors is now possible with a variety of structural analogues. Adenosine analogues resistant to metabolism or uptake mechanisms have become available. These are particularly valuable, since their apparent potencies are less affected by metabolic removal from the effector system than other adenosine analogues. The adenosine analogues exhibit different rank order of potencies at $A_1$ and $A_2$ adenosine receptors, providing a simple method of categorizing a physiological response with respect to the nature of the adenosine receptor. The blockade of adenosine receptors, i.e., antagonism, provides another method of categorizing a response with respect to the involvement of adenosine receptors.

Adenosine, perhaps, represents a general regulatory substance, since no particular cell type or tissue appears uniquely responsible for its formation. In this regard, adenosine is unlike various endocrine hormones. Furthermore, there is no evidence for storage and release of adenosine from nerve or other cells. Thus, adenosine is unlike various neurotransmitter substances.

Although adenosine can affect a variety of physiological functions, particular attention has been directed over the years to those functions that might lead to clinical applications. Preeminent has been the cardiovascular effects of adenosine, which lead to vasodilation and hypotension but which also lead to cardiac depression. The antilipolytic, antithrombotic, and antispasmodic actions of adenosine have also received some attention. Adenosine stimulates steroidogenesis in adrenal cells, probably via activation of adenylate cyclase, and inhibits neurotransmission and spontaneous activity of central neurons. Finally, the bronchoconstrictor action of adenosine and its antagonism by xanthines represents an important area of research.

Although theophylline and other xanthines, such as caffeine, are relatively weak adenosine antagonists, having affinity constants in the range of 10–50 micromolar, they owe many of their pharmacological effects to blockage of adenosine-mediated functions at the $A_1$ and $A_2$ receptor sites. The $A_1$-adenosine receptor is inhibitory to adenylate cyclase and appears involved in antilipolytic, cardiac, and central depressant effects of adenosine. The $A_2$-adenosine receptor is stimulatory to adenylate cyclase and is involved in hypotensive, antithrombotic, and endocrine effects of adenosine. Some xanthines, such as 3-isobutyl-1-methylxanthine, not only block adenosine receptors but also have potent inhibitory effects on phosphodiesterases.

The brochodilator effects of the xanthines, particularly, theophylline, have received considerable commercial attention and various preparations of theophylline, such as the anhydrous base or salts thereof, including sodium acetate, sodium benzoate, sodium salicylate, calcium salicylate, etc., are available as tablets, capsules, and elixirs including sustained released forms. Other related xanthines, such as dyphyllin, have received widespread usage. Caffeine has been used alone and in combination with other drugs in the treatment of headaches.

Many of the xanthines, however, such as theophylline, have undesirable side effects. Some of these side effects may be due to actions at sites other than adenosine receptors. It is also likely that some side effects are associated with blockade of the adenosine receptors, themselves. It appears that at least some of the side-effects caused by the adenosine receptor antagonists could be avoided by the development of more potent blockers of such receptors which, because of their increased blocking action, could be employed in lower doses and, thus, would be less likely to produce side-effects not associated with the adenosine receptor blockade. Additionally, where the therapeutic effect is due to blockade of one subtype of adenosine receptor, while side-effects relate to blockade of a different subtype of adenosine receptor, drugs, which are extremely potent at one receptor and substantially less active at another adenosine receptor, also should have a reduced likelihood of side-effects.

Potent and $A_2$-selective adenosine antagonists, suitable as pharmacological tools, have long been lacking. $A_2$-selective antagonists also may have application as therapeutic agents, e.g., in the treatment of Parkinson's disease (Schiffman et al., *Drug Dev. Res.*, 28, 381–385 (1993)). The slightly selective, non-xanthine antagonist CGS 15943 was under development as an antiasthmatic (Jacobson et al., *J. Med. Chem.*, 35, 407–422 (1992)). A low affinity antagonist, 3,7-dimethyl-1-propargylxanthine (DMPX), was reported to be $A_2$-selective but by less than one order of magnitude (Ukena et al., *Life Sci.*, 39, 743–750 (1986)). It was relatively weak in blocking the in vivo effects of $N^6$-cyclohexyladenosine (CHA) compared to those of 5'-N-ethylcarboxamidoadenosine (NECA), suggesting some $A_2$ selectivity. Several non-xanthine antagonists of the triazoloquinazoline class, including CGS 15943, are $A_2$-selective but also by only one order of magnitude (Francis et al., *J. Med. Chem.*, 31, 1014–1020 (1988)). The locomotor activity of several members of this class was described previously (Griebel et al., *NeuroReport*, 2, 139–140 (1991)). A triazoloquinozaline derivative, CP66,713, was found to be 12-fold selective in binding assays at rat brain $A_{2a}$- vs. $A_1$-receptors (Sarges et al., *J. Med. Chem.*, 33, 2240–2254 (1990)). Low selectivity, interspecies differences in affinity, and low water solubility precluded extensive use of this compound. In one study, partial antagonism of $A_2$ depression of locomotor activity was achieved in vivo using CP66,713 (Nikodijevic et al., 1991, supra). At the same dose CP66,713 had no effect on $A_1$ depression of locomotor activity.

It was only recently that 8-styrylxanthines were reported as the first potentially useful compounds by Shimada et al. (*J. Med. Chem.*, 35, 2342–2345 (1992)). These authors found that 8-styryl derivatives of 1,3-dimethylxanthines were the most selective for $A_2$ receptors (selectivities greater than 5000-fold were reported), but the affinities of the corresponding 1,3-propyl analogues at both subtypes were greater (the most potent compound having a $K_i$ value of 7.8 nM at $A_2$ receptors).

The literature is replete with examples of 8-substituted xanthine derivatives, including 8-substituted 1,3,7-trialkyl-xanthines, such as 8-styryl-1,3,7-trialkyl-xanthines. For example, U.S. Pat. No. 3,641,010 (Schweiss et al.) discloses 1,3-dialkyl-7-methyl-8-styryl-xanthines and describes the compounds as cerebral stimulants of the caffeine type. WO 92/06976 discloses alkyl-substituted 8-styryl-xanthines as selective $A_2$-adenosine receptor antagonists useful in the treatment of asthma and osteoporosis. 1-methyl-3,7-disubstituted-8-benzyl-xanthine derivatives useful in the treatment of asthma and bronchitis are disclosed in European Patent Application 0 215 736. The administration of methylxanthines, which are described as adenosine antagonists, to alleviate asystole and cardiac arrhythmia associated with resuscitation is described in U.S. Pat. No. 4,904,472. Various substituted theophyllines/xanthines are disclosed in U.S. Pat. Nos. 2,840,559, 3,309,271, 3,624,215, 3,624,216, 4,120,947, 4,297,494, 4,299,832, 4,546,182, 4,548,820, 4,558,051, 4,567,183, and 4,883,801, although only the U.S. Pat. Nos. 4,593,095, 4,612,315, 4,696,932, 4,755,517, 4,769,377, 4,783,530, 4,879,296, 4,981,857, 5,015,647, and 5,047,534 describe the disclosed compounds as potent adenosine receptor antagonists. Although a number of these references disclose xanthine compounds and describe them as "potent" and/or "selective" $A_2$-adenosine receptor antagonists, the potency and/or selectivity actually realized is not that significant. Accordingly, there remains a need for highly selective and potent $A_2$-adenosine receptor antagonists. Such compounds would reduce, if not completely eliminate, the side effects associated with $A_2$-adenosine receptor antagonists of reduced potency or selectivity by increasing blocking activity at one receptor, significantly, if not completely, eliminating blocking activity at non-$A_2$-adenosine receptors and, consequently, enabling the employment of reduced dosages.

An object of the present invention is to provide $A_2$-adenosine receptor antagonists of high potency and/or selectivity. Another object of the present invention is to provide a pharmaceutical composition comprising one or more of the present inventive adenosine receptor antagonists. Yet another object of the present invention is to provide a method of selectively antagonizing $A_2$ adenosine receptors in a mammal in need of selective antagonism of its $A_2$ adenosine receptors. By means of these objects, the present invention offers advantages over currently available $A_2$-adenosine receptor antagonists by providing $A_2$-selective adenosine receptor antagonists of increased potency and/or specificity. Accordingly, the present invention also provides an improved pharmaceutical composition comprising $A_2$-selective adenosine receptor antagonists and an improved method for the selective antagonism of $A_2$ adenosine receptors in a mammal in need of such selective antagonism. The method, since it involves the use of $A_2$-selective adenosine receptor antagonists having increased potency and/or selectivity over currently available antagonists, is expected to reduce, if not completely eliminate, the side effects associated with the $A_2$-adenosine receptor antagonists by enabling the employment of reduced dosages.

BRIEF SUMMARY OF THE INVENTION

The present invention provides novel 8-substituted 1,3,7-trialkyl-xanthines. Preferably, the 8-substituted 1,3,7-trialkyl-xanthine is a 1,3,7-trialkyl-8-styryl-xanthine having the formula:

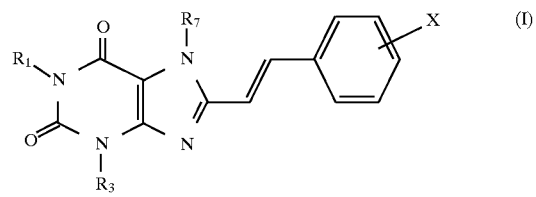

wherein $R_1$, $R_3$, and $R_7$ are methyl and X is one to three substituents, which may be the same or different and are preferably positioned at positions 3, 4, 5, and combinations thereof, such as amino, $C_1$–$C_4$ aliphatic saturated monoacyl amino, $C_1$–$C_4$ aliphatic saturated diacyl amino, halo, $C_1$–$C_3$ alkyloxy, amino $C_1$–$C_4$ alkyloxy, amino $C_1$–$C_4$ alkenyloxy, isothiocyanato, and a diazonium salt. Even more preferred is a 1,3,7-trimethyl-8-styryl-xanthine, wherein X is selected from the group consisting of 3-amino, 3-$C_1$–$C_4$ aliphatic saturated monoacyl amino, 3-$C_1$–$C_4$ aliphatic saturated diacyl amino, 3-halo, 3,5-dihalo, 4-alkoxy, 3,5-dialkoxy, 4-(amino-$C_1$–$C_4$-alkyloxy)-3,5-dialkoxy, 4-(amino-$C_1$–$C_4$-alkenyloxy)-3,5-dialkoxy, 3-isothiocyanato, and 3-diazonium salt. The $C_1$–$C_4$ aliphatic saturated monoacyl amino is preferably acetylamino, the $C_1$–$C_4$ aliphatic saturated diacyl amino is preferably succinylamino, the halo is preferably bromo, chloro, fluoro, or iodo, the $C_1$–$C_3$ alkyloxy is preferably methoxy, the amino $C_1$–$C_4$ alkenyloxy is preferably 4-amino-2-trans-buten-1-oxy, and the 3-diazonium salt is preferably $N_2^+BF_4^-$.

Also provided by the present invention is a 1,3,7-trialkyl-8-styryl-xanthine having the formula:

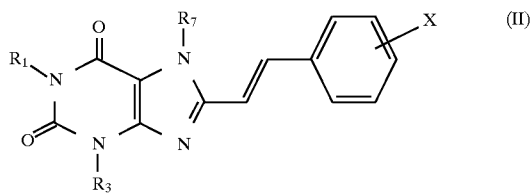

wherein $R_1$ and $R_3$ are propyl, $R_7$ is methyl, and X is one or two substituents, which may be the same or different and are preferably positioned at positions 3, 4, 5, or combinations thereof, such as amino, halo, and $C_1$–$C_3$ alkoxy. Preferably, X is 3-amino, 3-halo, 3,5-dihalo, 3,4-dialkoxy, and 3,5-dialkoxy. Even more preferably, X is 3-amino, 3-fluoro, 3,5-difluoro, 3,4-dimethoxy, and 3,5-dimethoxy.

The present invention also provides a 1,3,7-trialkyl-8-substituted-xanthine having the formula:

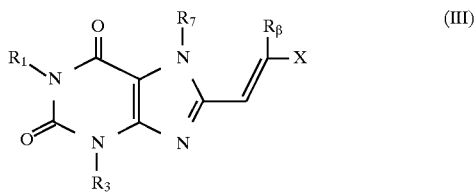

wherein $R_1$, $R_3$, and $R_7$ are methyl, $R_\beta$ is hydrogen or methyl, and X is R, C(=O)OH, C(=O)OR, or C(=O)NH—R, wherein R is a $C_1$–$C_6$ alkyl or phenyl, with the proviso that $R_\beta$ is not hydrogen when X is phenyl. Preferably, X is n-propyl, C(=O)OH, or C(=O)OC$(CH_3)_3$.

A pharmaceutical composition comprising a pharmaceutically acceptable carrier and a therapeutically effective amount of one or more of the above described compounds as well as a method of selectively antagonizing $A_2$ adenosine receptors in a mammal in need of such antagonism are also provided.

DETAILED DESCRIPTION OF THE INVENTION

Figure 1:
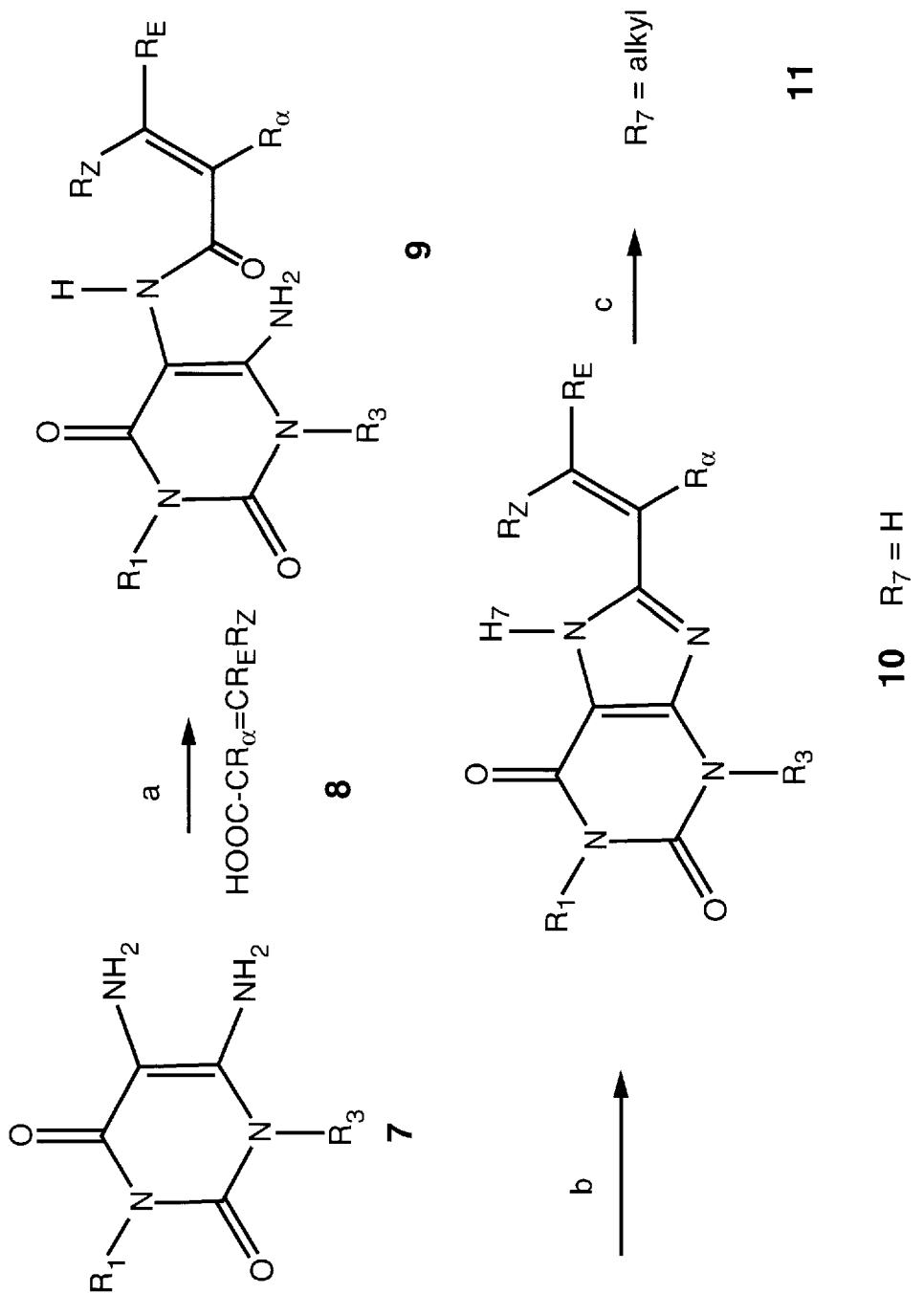
FIG. 1 is a schematic diagram, which shows the synthesis route of 8-styryl-xanthine derivatives.

The present invention provides novel 8-substituted 1,3,7-trialkyl xanthines. Preferably, the 8-substituted 1,3,7-trialkyl xanthine is a 1,3,7-trialkyl-8-styryl-xanthine having the formula:

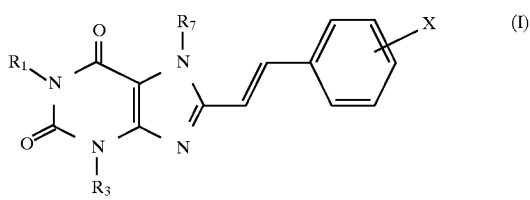

wherein $R_1$, $R_3$, and $R_7$ are methyl and X is one to three substituents, which may be the same or different, selected from the group consisting of amino, $C_1$–$C_4$ aliphatic saturated monoacyl amino, $C_1$–$C_4$ aliphatic saturated diacyl amino, halo, $C_1$–$C_3$ alkyloxy, amino $C_1$–$C_4$ alkyloxy, amino $C_1$–$C_4$ alkenyloxy, isothiocyanato, and a diazonium salt. Preferably, X is at a position selected from the group consisting of 3, 4, 5, and combinations thereof. Also, X is preferably 3-amino, 3-$C_1$–$C_4$ aliphatic saturated monoacyl amino, 3-$C_1$–$C_4$ aliphatic saturated diacyl amino, 3-halo, 3,5-dihalo, 4-alkoxy, 3,5-dialkoxy, 4-(amino-$C_1$–$C_4$-alkyloxy)-3,5-dialkoxy, 4-(amino-$C_1$–$C_4$-alkenyloxy)-3,5-dialkoxy, 3-isothiocyanato, or 3-diazonium salt. The $C_1$–$C_4$ aliphatic saturated monoacyl amino is preferably acetylamino, whereas the $C_1$–$C_4$ aliphatic saturated diacyl amino is preferably succinylamino, the halo is preferably bromo, chloro, fluoro, or iodo, the $C_1$–$C_3$ alkyloxy is preferably methoxy, the amino $C_1$–$C_4$ alkyloxy is preferably 4-amino-butyloxy, the amino $C_1$–$C_4$ alkenyloxy is preferably 4-amino-2-trans-buten-1-oxy, and the 3-diazonium salt is preferably $N_2^+BF_4^-$.

The 1,3,7-trimethyl-8-styryl-xanthines, wherein X is 3-amino, 3-iodo, 3-diazonium salt, 4-methoxy, 4-(4-aminobutyloxy)-3,5-dimethoxy, or 4-(4-amino-2-trans-buten-1-oxy)-3,5-dimethoxy, are preferred for functionalized congeners for coupling to other molecules.

Also provided by the present invention is a 1,3,7-trialkyl-8-styryl-xanthine having the formula:

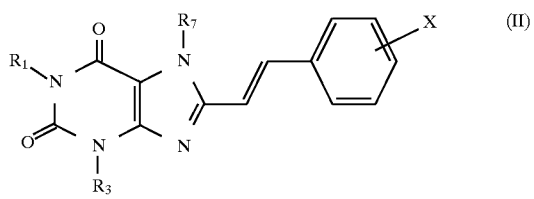

wherein $R_1$ and $R_3$ are propyl, $R_7$ is methyl, and X is one or two substituents, which may be the same or different, selected from the group consisting of amino, halo, or $C_1$–$C_3$ alkoxy.

Preferably, X is at a position selected from the group consisting of 3, 4, 5, and combinations thereof. Also, X is preferably 3-amino, 3-halo, 3,5-dihalo, 3,4-dialkoxy, or 3,5-dialkoxy. Even more preferably, X is 3-amino, 3-fluoro, 3,5-difluoro, 3,4-dimethoxy, or 3,5-dimethoxy.

The present invention also provides an 8-substituted 1,3,7-trialkylxanthine having the formula:

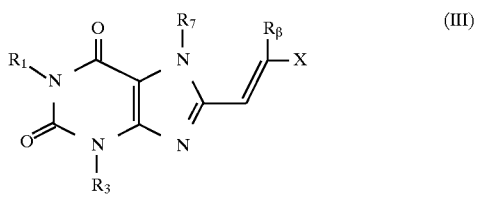

wherein $R_1$, $R_3$, and $R_7$ are methyl, $R_\beta$ hydrogen or methyl, and X is R, C(=O)OH, C(=O)OR, or C(=O)NH—R, wherein R is a $C_1$–$C_6$ alkyl or phenyl, with the proviso that $R_\beta$ is not hydrogen when X is phenyl.

The compounds of the present invention may be synthesized by any suitable means. However, the 8-styryl-xanthine derivatives of the present invention are preferably synthesized by condensation of a trans-cinnamic acid with a 1,3-dialkyl-5,6-diaminouracil to form an amide, which is cyclized under strongly basic conditions to give the 7-H xanthine derivative, which is subsequently methylated, using methyl iodide, for example. Aryl amino substituents are preferably obtained via Zn/HOAc reduction of the corresponding nitro derivative or, in the case of tertiary aniline, by direct incorporation of the corresponding cinnamic acid. The details of the synthesis of these derivatives are set forth in FIGS. 1 and 2 and Example 1.

The other 8-substituted xanthine derivatives of the present invention are preferably synthesized using a palladium-catalyzed Heck reaction. The details of the synthesis of these derivatives are set forth in FIG. 3 and Example 2.

The potency of the present compounds as adenosine receptor antagonists may be determined by a standard screening procedure (Bruns et al., PNAS USA, 77(9), 5547–5551 (September 1980)).

The compounds of the present invention may be used as is or in the form of their pharmaceutically acceptable salts and derivatives, and may be used alone or in appropriate combination with one or more other 8-substituted xanthine derivatives or other pharmaceutically active compounds.

The present invention also provides pharmaceutical compositions comprising a pharmaceutically acceptable carrier and a therapeutically effective amount of one or more of the 8-substituted 1,3,7-trialkyl-xanthine derivatives of the present invention, i.e., one or more of the 1,3,7-trimethyl-8-styryl-xanthines of Formula I, 1,3-dipropyl-7-methyl-8-styryl-xanthines of Formula II, and 1,3,7-trimethyl-8-substituted xanthines of Formula III described above, as well as their pharmaceutically acceptable salts and derivatives.

Examples of pharmaceutically acceptable acid addition salts for use in the present inventive pharmaceutical compositions include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic, for example p-toluenesulphonic acids. The xanthine derivative may be present in the pharmaceutical composition in any suitable quantity. The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of excipient will be determined in part by the particular compound, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts and suitable detergents include cationic detergents, for example, dimethyl dialkyl ammonium halides, and alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-β-aminopropionates, and 2-alkyl-imidazoline quaternary ammonium salts, as well as mixtures.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present invention also provides for antagonizing $A_2$ adenosine receptors by contacting such receptors with the 8-substituted 1,3,7-trialkyl-xanthine derivatives of the present invention.

The method of the present invention can be practiced in vitro for scientific and research purposes. For example, the present inventive xanthine derivatives may be used to probe adenosine receptors in order to isolate or characterize the receptors. In this regard, the amine and carboxylic acid derivatized analogues are most useful. For example, an amine congener (e.g. 22b or 40 of Table I) of suitable high affinity may be converted to the condensation product with the p-aminophenylacetyl (PAPA) group for radioiodination and photoaffinity cross-linking to the receptor protein. The cross-linking to the receptor may be carried out with the photoaffinity cross-linking reagent SANPAH, or by conversion of the aryl amino group to an azide, followed by photolysis in the presence of the receptor. Alternately, a chemically reactive bifunctional reagent, such as p-phenylene diisothiocyanate, may be coupled to the amine congener, in a manner that leaves one electrophilic group unreacted. Another type of reporter group, a fluorescent dye, such as fluorescein isothiocyanate, may be coupled to an amine congener to provide an affinity probe. These probes obviate the need for radioactive ligands for receptor characterization in studies utilizing membrane homogenates and tissue slices. A carboxylic acid congener (e.g. 24 of Table I) may be linked to an amine functionalized agarose matrix for the affinity chromatography of $A_{2a}$-receptors.

The method of the present invention has particular usefulness in in vivo applications, such as the therapeutic treatment of Parkinson's disease, Huntington's chorea, and other diseases of the central nervous system (CNS), particularly those involving the dopaminergic or GABA transmitter systems, both of which are modulated by $A_{2a}$ adenosine receptors. A relationship between the striatal dopaminergic and the adenosine $A_2$ systems has been proposed (reviewed in Ferre et al., *Neuroscience*, 51, 501–512 (1992)). Activation of $A_{2a}$ receptors inhibits a dopaminergic pathway in the striatum. $D_2$-dopamine receptors and $A_{2a}$ receptors are colocalized on the subset of GABAergic neurons in the striatum, which innervates the globus pallidus and expresses enkephalin. Thus, an $A_2$ antagonist would be expected to enhance dopaminergic striatopallidal transmission. The other class of striatal GABAergic neurons, those expressing substance P, are located in the striatonigral pathway. An $A_1$ antagonist would not have a direct postsynaptic action on striatopallidal neurons, but may still affect both striatopallidal and striatonigral dopaminergic pathways by enhancing the release of dopamine in the striatum. Activation of presynaptic $A_1$ receptors is associated with the inhibition of release of stimulatory neuro-transmitters in the CNS (Ferre et al., supra). Accordingly, the present inventive method is expected to have utility in the enhancement of dopaminergic activity in the brain and, therefore, is potentially useful in the treatment of diseases accompanied by a deficiency in dopaminergic function, such as Parkinson's disease. The present inventive method includes the administration to an animal, such as a mammal, particularly a human, in need of selective antagonism of its $A_2$ adenosine receptors of a therapeutically effective amount of one or more of the aforementioned present inventive 8-substituted 1,3,7-trialkyl-xanthines or pharmaceutically acceptable salts or derivatives thereof, alone or in combination with one or more other pharmaceutically active compounds.

Some of the compounds of the present invention, such as the 1,3,7-trimethyl-8-styryl xanthines, wherein X is 3-amino, 3-iodo, 3-diazonium salt, 4-methoxy, 4-(4-aminobutyloxy)-3,5-dimethoxy, or 4-(4-amino-2-trans-buten-1-oxy)-3,5-dimethoxy, may be utilized as functionalized congeners for coupling to other molecules, such as amines and peptides. The use of such congeners enables increased potency, prolonged duration of action, specificity of action, and prodrugs. Water solubility is also enhanced, which allows for reduction, if not complete elimination, of undesirable binding to plasma proteins and partition into lipids. Accordingly, improved pharmacokinetics may be realized.

One skilled in the art will appreciate that suitable methods of administering a compound of the present invention to an animal are available, and, although more than one route can be used to administer a particular compound, a particular route can provide a more immediate and more effective reaction than another route. Accordingly, the above-described methods are merely exemplary and are in no way limiting.

The dose administered to an animal, particularly a human, in the context of the present invention should be sufficient to effect a prophylactic or therapeutic response in the animal over a reasonable time frame. One skilled in the art will recognize that dosage will depend upon a variety of factors including the strength of the particular compound employed, the age, species, condition, and body weight of the animal, as well as the severity of the infection and stage of the disease. The size of the dose will also be determined by the route, timing and frequency of administration as well as the existence, nature, and extent of any adverse side-effects that might accompany the administration of a particular compound and the desired physiological effect.

Suitable doses and dosage regimens can be determined by conventional range-finding techniques. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of selective inhibition of $A_2$-adenosine receptors, e.g., from little inhibition to essentially full inhibition.

The following examples further illustrate the present invention and, of course, should not be construed as in any way limiting its scope.

EXAMPLE 1

This example describes the synthesis of 8-styryl-xanthine derivatives substituted at the 1, 3, and 7 xanthine positions and at various phenyl positions of the styryl moiety.

Figure 2:
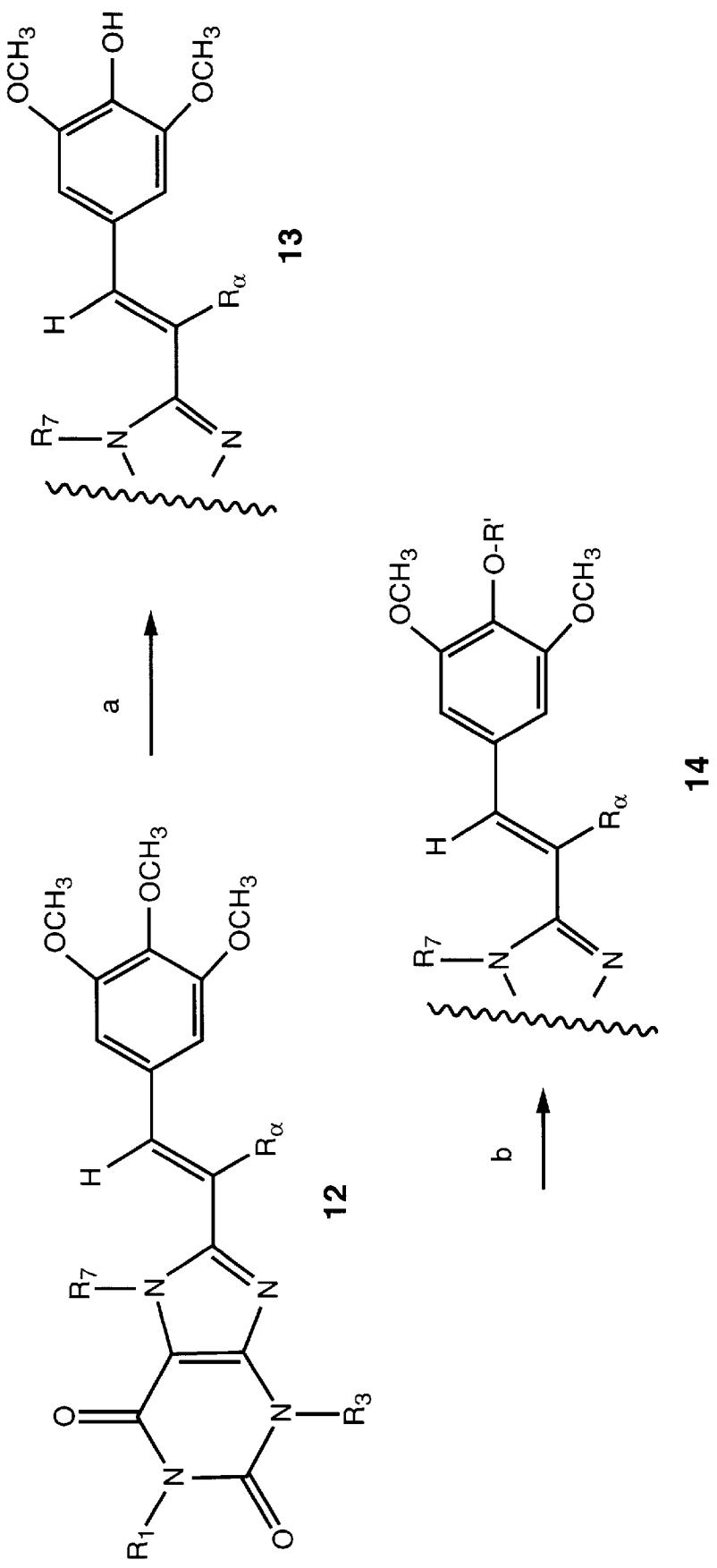
FIG. 2 is a schematic diagram, which shows the synthesis route of 8-(4-hydroxy-3,5-dimethoxystyryl)-xanthines and derivatives thereof.

8-styryl-xanthine derivatives substituted at the 1, 3, and 7 xanthine positions and at various phenyl positions of the styryl moiety were synthesized as shown in FIGS. 1 and 2. FIG. 1 is a schematic diagram of the synthesis of 8-styryl xanthine derivatives. In step (a) the reagents included 1-(3-dimethylaminopropyl)-3-ethylcarbodiimide hydrochloride (EDAC), 4-(N,N-dimethylamino)-pyridine (DMAP), and imidazole. Sodium hydroxide (NaOH) was used in step (b), which was carried out at 80° C. FIG. 2 is a schematic diagram of the synthesis of 8-(4-hydroxy-3,5-dimethoxystyryl)-xanthines and their derivatives. In step (a), which was carried out at 160° C., $C_6H_5SNa$ was used. R'—Br was used in step (b). The structures of those compounds that were synthesized in accordance with the following methods are set forth in Table I. The numbers used to refer to such compounds are those which appear in Table I.

TABLE I

Affinities of 8-styryl xanthine derivatives in radioligand binding assays at rat brain $A_1$ and $A_2$ receptors.[a]

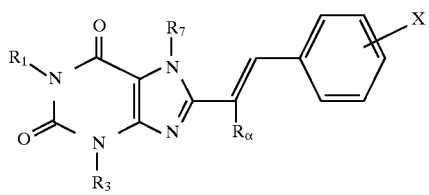

| Compd. | $R_1, R_3 = R_7 =$ | | X = | $K_i(A_1)$[a] | $K_i(A_{2a})$[a] | $A_1/A_{2a}$ ratio |
|---|---|---|---|---|---|---|
| 15a. | Me | H | H | 654 ± 170 | 291 ± 40 | 2.3 |
| 15b. | Me | Me | H | 3,890 ± 1,150 | 94 ± 36 | 41 |
| 16. | Me | H | H($R_a$ = F) | 2,190 ± 400 | 2,110 ± 810 | 1.4 |
| 17a. | Me | H | 2-methoxy | 1,730 ± 420 | 645 ± 144 | 2.7 |
| 17b. | Me | Me | 2-methoxy | 4,760 ± 720 | 267 ± 84 | 18 |
| 18. | Me | H | 3-hydroxy | 702 ± 40 | 303 ± 55 | 2.4 |

TABLE I-continued

Affinities of 8-styryl xanthine derivatives in radioligand binding
assays at rat brain $A_1$ and $A_2$ receptors.[a]

| Compd. | $R_1$, | $R_3 =$ | $R_7 =$ | X = | $K_i(A_1)$[a] | $K_i(A_{2a})$[a] | $A_1/A_{2a}$ ratio |
|---|---|---|---|---|---|---|---|
| 19a. | Me | | H | 3-methoxy | 1,830 ± 821 | 378 ± 155 | 4.8 |
| 19b. | Me | | Me | 3-methoxy | 5,430 ± 1,470 | 84.8 ± 24.0 | 64 |
| 20a. | Me | | H | 3-trifluoromethyl | 881 ± 251 | 343 ± 58 | 2.6 |
| 20b. | Me | | Me | 3-trifluoromethyl | 3,330 ± 410 | 134 ± 44 | 25 |
| 21a. | Me | | H | 3-nitro | 1,060 ± 150 | 438 ± 106 | 2.4 |
| 21b. | Me | | Me | 3-nitro | 2,140 ± 480 | 195 ± 44 | 11 |
| 22a. | Me | | H | 3-amino | 288 ± 60 | 202 ± 79 | 1.4 |
| 22b. | Me | | Me | 3-amino | 1,690 ± 360 | 57 ± 3 | 30 |
| 23. | Me | | Me | 3-(acetylamino) | 9,470 ± 2,540 | 39 ± 21 | 240 |
| 24. | Me | | Me | 3-(succinylamino) | 35,100 ± 11,700 | 143 ± 45 | 250 |
| 25. | Me | | Me | 3-t-butyloxycarbonylamino | 23,600 ± 2,500 | 784 ± 100 | 30 |
| 26. | Me | | Me | 3-di-(t-butyloxycarbonyl)amino | 10,800 ± 1,300 | 740 ± 77 | 15 |
| 27a. | Me | | H | 3-fluoro | 2,720 ± 360 | 516 ± 99 | 5.3 |
| 27b. | Me | | Me | 3-fluoro | 15,780 ± 2,860 | 83 ± 18 | 190 |
| 28a. | Me | | Me | 3-chloro | 28,200 ± 7,000 | 54 ± 19 | 520 |
| 28b. | Me | | Me | 3-bromo | 3,520 ± 80 | 29.2 ± 3.1 | 120 |
| 28c. | Me | | Me | 3-iodo | 2,370 ± 1,420 | 38.6 ± 12.5 | 61 |
| 28d. | Me | | Me | 3-diazonium ($N_2^+BF_4^-$) | 2,990 ± 560 | 64.8 ± 19.6 | 46 |
| 28e. | Me | | Me | 3-isothiocyanato | 20,300 ± 1,700 | 111 ± 1 | 180 |
| 29a. | Me | | H | 4-methoxy | 858 ± 320 | 472 ± 132 | 1.8 |
| 29b. | Me | | Me | 4-methoxy | 14,200 ± 3,500 | 327 ± 75 | 44 |
| 30a. | Me | | H | 4-dimethylamino | 3,030 ± 300 | 12,800 | 0.24 |
| 30b. | Me | | Me | 4-dimethylamino | 5.6%[b] (3 × $10^{-5}$) | 9,270 ± 150 | >1 |
| 31a. | Me | | H | 2,3-dimethoxy | 1,600 ± 250 | 600 ± 204 | 2.7 |
| 31b. | Me | | Me | 2,3-dimethoxy | 5,390 ± 1,020 | 716 ± 144 | 75 |
| 32a. | Me | | H | 3,4-dimethoxy | 5,340 ± 1,440 | 1,100 ± 250 | 48 |
| 32b. | Me | | Me | 3,4-dimethoxy | 13,790 ± 2,420 | 197 ± 33 | 70 |
| 33a. | Me | | H | 3,5-dimethoxy | 3,044 ± 520 | 120 ± 36 | 25 |
| 33b. | Me | | Me | 3,5-dimethoxy | 12.5 ± 6.3%[b] ($10^{-5}$) | 75.3 ± 29.1 | >200 |
| 34a. | Me | | H | 3,5-difluoro | 2,330 ± 830 | 366 ± 77 | 6.4 |
| 34b. | Me | | Me | 3,5-difluoro | 14,750 ± 3,890 | 65 ± 9 | 230 |
| 35. | Me | | Me | 3,5-dimethoxy-4-hydroxy | 8,700 ± 4,100 | 450 ± 66 | 19 |
| 36. | Me | | Me | 4-acetoxy-3,5-dimethoxy | 6,330 ± 1,680 | 68 ± 22 | 93 |
| 37. | Me | | Me | 4-(4-benzyloxy)-3,5-dimethoxy | 4,120 ± 460 | 139 ± 7 | 30 |
| 38. | Me | | Me | 4-(4-amino-butyloxy)-3,5-dimethoxy | 6,170 ± 1,010 | 173 ± 43 | 36 |
| 39. | Me | | Me | 4-[4-t-(butyloxycarbonyl)amino-butyloxy-3,5-dimethoxy | 11,031 | 265 ± 105 | 42 |
| 40. | Me | | Me | 4-(4-amino-2-t(ans-buten-1-oxy)-3,5-dimethoxy | 6,280 ± 1,580 | 228 ± 20 | 28 |
| 41. | Me | | Me | 4-(4-acetylamino-2-trans-buten-1-oxyl)-3,5 dimethoxy | 17 ± 7%[b] ($10^{-5}$) | 216 ± 40 | >50 |
| 42. | Me | | Me | 4-[4-t-butyloxycarbonyl)amino-2-trans buten-1-oxy]-3,5-dimethoxy | 11 ± 5%[b] ($10^{-5}$) | 353 ± 62 | >40 |
| 43a. | Me | | H | 2,3,4-trimethoxy | 26 ± 10%[b] ($10^{-5}$) | 1,610 ± 260 | >5 |
| 43b. | Me | | Me | 2,3,4-trimethoxy | 6,920 ± 330 | 206 ± 81 | 34 |
| 44a. | Me | | H | 3,4,5-trimethoxy | 2,280 ± 530 [>100,000][c] | 360 ± 170 [71][c] | 6.3 [>1100] |
| 44b. | Me | | Me | 3,4,5-trimethoxy | 9,200 ± 3,560 [>100,000][c] | 131 ± 54 [18][c] | 70 [>5600] |
| 44c. | Me | | Et | 3,4,5-trimethoxy | 6,290 ± 680 | 882 ± 239 | 7.1 |
| 44d. | Me | | hydroxyethyl | 3,4,5-trimethoxy | 26 ± 9%[b] ($10^{-5}$) | 22%[b] ($10^{-5}$) | — |
| 44e. | Me | | propargyl | 3,4,5-trimethoxy | 4,040 ± 370 | 525 ± 220 | 7.7 |
| 44f. | Me | | phenylethyl | 3,4,5-trimethoxy | 32 ± 9%[b] ($10^{-5}$) | 14%[b] ($10^{-5}$) | — |
| 45a. | Et | | H | 3,4,5-trimethoxy | 852 ± 277 | 269 ± 7 | 3.2 |
| 45b. | Et | | Me | 3,4,5-trimethoxy | 2,790 ± 960 | 81 ± 17 | 34 |
| 46. | allyl | | Me | 3,4,5-trimethoxy | 1,930 ± 100 [>100,000][c] | 131 ± 69 [15][c] | 13 [>6700] |
| 47. | Pr | | H | H | 55 ± 28 [1800 or 22[d]][c] | 44 ± 19 [26 or 85[d]][c] | 1.3 [69 or 0.26[b]] |
| 48. | Pr | | Me | 3-nitro | 272 ± 68 | 56.2 ± 6.8 | 4.8 |
| 49. | Pr | | Me | 3-amino | 113 ± 21 | 18.9 ± 5.3 | 6.0 |
| 50a. | Pr | | H | 3-fluoro | 78 ± 17 | 153 ± 31 | 0.51 |
| 50b. | Pr | | Me | 3-fluoro | 301 ± 64 | 33 ± 15 | 9.1 |
| 51a. | Pr | | H | 3-chloro | 167 ± 39 | 216 ± 66 | 0.77 |

TABLE I-continued

Affinities of 8-styryl xanthine derivatives in radioligand binding assays at rat brain $A_1$ and $A_2$ receptors.[a]

| Compd. | $R_1$, $R_3$ = | $R_7$ = | X = | $K_i(A_1)$[a] | $K_i(A_{2a})$[a] | $A_1/A_{2a}$ ratio |
|---|---|---|---|---|---|---|
| 51b. | Pr | Me | 3-chloro | 874 ± 222 | 61.3 ± 17.6 | 14 |
| 52a. | Pr | H | 3,4-dimethoxy | 71 ± 11 | 48.5 ± 8.6 | 1.3 |
| | | | | [1700][c] | [6700][c] | [0.25] |
| 52b. | Pr | Me | 3,4-dimethoxy [KF17837] | 577 ± 42 | 31.1 ± 11.8 | 19 |
| | | | | [1500][c] | [7.8][c] | [190] |
| 53a. | Pr | H | 3,5-dimethoxy | 632 ± 152 | 210 ± 140 | 3.0 |
| 53b. | Pr | Me | 3,5-dimethoxy | 2,630 ± 20 | 24.0 ± 6.0 | 110 |
| 54a. | Pr | H | 3,5-difluoro | 146 ± 25 | 346 ± 97 | 0.42 |
| 54b. | Pr | Me | 3,5-difluoro | 382 ± 40 | 53 ± 15 | 7.2 |
| 55a. | Pr | H | 2,3,4-trimethoxy | 97 ± 19 | 64.0 ± 15.6 | 1.5 |
| 55b. | Pr | Me | 2,3,4-trimethoxy | 379 ± 128 | 68.5 ± 12.6 | 5.5 |
| 56a. | Pr | H | 2,4,5-trimethoxy | 143 ± 19 | 323 ± 74 | 0.44 |
| 56b. | Pr | Me | 2,4,5-trimethoxy | 689 ± 239 | 327 ± 52 | 2.1 | a. Expressed in nM (single determination or mean ± S.E.M. for 3 or more determinations) vs [$^3$H]PIA (1 nm) at rat $A_1$-receptors and vs [$^3$H]CGS21680 (5 nM) at rat striatal $A_2$-receptors
b. Percent displacement of specific binding at the concentration indicated in parentheses
c. Values in brackets are from Shimada et. al., J. Med. Chem., 35, 2342–2345 (1992) and represent $K_i$ values vs. [$^3$H]NECA in rat striatum and vs. [$^3$H]CHA in guinea pig brain, unless noted
d. Affinities at both $A_1$ and $A_2$ receptors measured in rat brain from Erickson et. al., J. Med. Chem., 34, 1431–1435 (1991)

A trans-cinnamic acid (8, FIG. 1) was condensed with a 1,3-dialkyl-5,6-diamino-uracil, 7, such as 5,6-diamino-1,3-dimethyl-uracil to obtain an amide, 9. The substituted cinnamic acid (1 equiv) was dissolved in a minimum volume of DMF containing 1,3-dialkyl-5,6-diamino-uracil (1.5 equiv). 1-(3-dimethylaminopropyl)-3-ethyl carbodiimide HCl (1 equiv) was added, followed by a catalytic amount (0.05 equiv) of 4-(N,N-dimethylamino)-pyridine and 0.05 equiv of imidazole. The mixture was stirred at room temperature for 3 h, and saturated sodium chloride solution was added (for 1,3-dipropyl derivatives, water was used here), to form a precipitate or amorphous insoluble fraction. The insoluble residue was filtered and dissolved in 4N aqueous sodium hydroxide containing sufficient methanol to obtain a clear solution. The mixture was heated at 60° C. for 2 hours or until the starting material completely disappeared, as judged using thin layer chromatography (TLC) (silica plate, CHCl$_3$; CH$_3$OH; HOAc; 85:10:5 v/v). The mixture was cooled and acidified to pH=1 with 6N aqueous hydrochloric acid solution. The precipitate was washed with water, dried and further purified using a preparative silica plate (85–95% CHCl$_3$, 5–15% methanol; 1–5% HOAc).

The resulting amide, 9, was cyclized under strongly basic conditions to give the 7-H xanthine derivative, 10, which was methylated using methyl iodide at 50°–60° C. An 8-styrylxanthine derivative (1 equiv) was dissolved in a minimum of N,N-dimethylformamide (DMF). Excess finely powdered anhydrous potassium carbonate was added and the solution was left for 10 min in an ultrasonic bath. Methyl iodide (5 equiv) was added. The mixture was stirred at 60° C. for 30 minutes or until the starting material completely disappeared as judged using TLC (silica, chloroform:methanol:acetic acid; 95:4:1 v/v). The reaction mixture was cooled, and excess concentrated aqueous ammonia solution was added. The precipitate was washed with water, dried in vacuo, and further purified, either by crystallization or by chromatography on a preparative thin layer plate (85–95% chloroform, 5–15% methanol; 1–5% acetic acid). The trans orientation of the 8-styryl group was verified for each of the derivatives based on the proton-proton coupling constants of the olefinic protons (typically $\geq$15 Hz).

[3,5-dimethoxy-4-hydroxy]-8-styrylxanthines were demethylated and then O-alkylated. 1,3,7-trialkyl-8-(3,4,5-trimethoxystyryl)-xanthine (1 equiv) was dissolved in minimum DMF, and 1.5 equiv of sodium thiophenoxide were added. The solution was heated to 150°–160° C. for 20 min or when judged complete using TLC. An appropriate halide (2 equiv for monohalide and 8 equiv for dihalide) was added, followed by finely powdered, anhydrous K$_2$CO$_3$. The solution was left in an ultrasonic bath for 15 min and further heated at 50°–80° C. for 2 h or until judged complete using TLC. The reaction mixture was cooled and extracted with petroleum ether. The crude product was precipitated by water (for product of reaction with monohalides) or reacted further (for dihalides) with concentrated aqueous ammonia and chromatographed on preparative TLC using 90–95% chloroform:5–10% methanol and 1% aqueous ammonia.

The 4-hydroxy intermediate, compound 35, was also isolated and recrystallized. $^1$H NMR DMSO,d$_6$ d 3.23 and 3.46 (each S, 3H, N$_1$ and N$_3$ CH$_3$); 3.83 (S, 6H 3,5-diOCH$_3$); 4.03 (S, 3H, N$_7$CH$_3$); 7.08 (S, 2H, Ar), 7.18 and 7.61 (each d, 1H, C=C, J=15.7 Hz), 8.82 (br s, 1H, ArOH).

Synthesis of hydroxyl ring-substituted 8-styrylxanthines was attempted by the usual route (FIG. 1), starting with the 3- or 4-hydroxycinnamic acid. The intermediate amide was formed in low yield, and the cyclization provided the desired xanthine in only very low yield (e.g. 18). Carrying out the sequence with hydroxyl protection in order to obtain a free hydroxyl group in the p-position of the final product was attempted, but proved unsatisfactory. Acetyl ester and p-methoxybenzyl ether derivatives formed the amide intermediate, 9, but the cyclization step in 4N NaOH failed. The attempted deprotection of mono-methoxy derivatives in the series using sodium thiophenolate, trimethylsilyl iodide, or nitrogen bases at high temperature was unsuccessful. It was, however, possible to selectively demethylate 8-(3,4,5-trisubstituted)-styrylxanthines, 12 (FIG. 2), using sodium thiophenolate in DMF at 160° C. The position of the free hydroxyl group (4-) in 13 was determined by proton NMR. This hydroxyl group could be readily acylated or alkylated (in some cases carried out in situ following the deprotection reaction) to provide 14.

Aryl amino substituents were obtained via Zn/HOAc reduction of the corresponding nitro derivative (e.g. 21) or, in the case of tertiary aniline (e.g. 30a), by direct incorporation of the corresponding cinnamic acid. The N-7 position of 30a was selectively alkylated using methyl iodide at 50°–60° C. to provide 30b. Catalytic hydrogenation of the nitrostyryl derivative 21 afforded the saturated aniline analogue 57.

7-methoxy-2-benzofuranecarboxylic acid, trans-cinnamic acid and the following derivatives thereof were obtained from Aldrich (St. Louis, Mo.): α-fluoro, 2-methoxy, 3,4-dimethoxy, 3,5-difluoro, and 3,5-dimethoxy. β-Methyl-3-nitrocinnamic acid was obtained from the Sigma-Aldrich Library of Rare Chemicals collection. 3- and 4-Methoxy derivatives of trans-cinnamic acid were obtained from Fluka (Ronkonoma, N.Y.). The following derivatives of trans-cinnamic acid were purchased from Lancaster (Windham, N.H.): 2,3-dimethoxy, 3,4,5-trimethoxy, 2,3,4-trimethoxy, 2,4,5-trimethoxy, and 3-fluoro. The following derivatives of trans-cinnamic acid were obtained from Janssen Chimica (Geel, Belgium): 3-trifluoromethyl, 3-chloro, and 3-nitro. 2-Chloroadenosine was obtained from Research Biochemicals, Inc. (Natick, Mass.). Compound 46 was the gift of Dr. Ray Olsson (Univ. So. Florida, Tampa, Fla.). 8-Cyclohexylcaffeine, 2, was the gift of Dr. John W. Daly (National Institutes of Health). Analytical TLC plates and silica gel (230–400 mesh) were obtained from VWR (Bridgeport, N.J.).

All xanthine derivatives were judged to be homogeneous using thin layer chromatography following final purification. New compounds were characterized (and resonances assigned) by 300 MHz proton nuclear magnetic resonance mass spectroscopy using a Varian GEMINI-300 FT-NMR spectrometer. Unless noted, chemical shifts are expressed as ppm downfield from tetramethylsilane. Synthetic intermediates were characterized by chemical ionization mass spectrometry ($NH_3$) and xanthine derivatives by fast atom bombardment mass spectrometry (positive ions in a glycerol matrix) on a JEOL SX102 mass spectrometer. In the EI mode accurate mass was determined using a VG7070F mass spectrometer. C, H, and N analyses were carried out by Atlantic Microlabs (Norcross, Ga.), and ±0.4% was acceptable.

1,3-Dimethyl-8-(2-methoxystyryl)xanthine (17a)

Compound 17a was made from 2-methoxycinnamic acid and triturated with hot methanol. mp above 300° C. $^1$H NMR DMSO-$d_6$ d 3.27 (s, 3H $N_3$—$CH_3$); 3.35 (s, 3H $N_7$—$CH_3$); 3.5 (s, 3H $OCH_3$); 3.9 (s, 3H, $N_7$—$CH_3$); 7.1 (d, 1H, J=18 Hz); 7.0–7.2 (m, 2H); 7.4 (m, 1H); 7.7 (d, 1H, J=8 Hz); 7.8 (d, 1H, J=18 Hz). MS (CI/$NH_3$) m/e 313 ($MH^+$, base) 281, 117.

1,3,7-Trimethyl-8-(2-methoxystyryl)xanthine (17b)

Compound 17b was made from 17a. mp 238°–240° C. $^1$H NMR DMSO-$d_6$ d 3.24 (s, 3H $N_3CH_3$); 3.48 (s, 3H $N_7CH_3$); 3.90 (s, 3H $OCH_3$); 4.06 (s, 3H, $N_7CH_3$); 7.0–7.14 (m, 2H); 7.34 (d, 1H, J=16 Hz); 7.4 (m, 1H); 7.9 (d, 1H, J=8 Hz); 8.0 (d, 1H, J=16 Hz). MS (CI/$NH_3$) m/e 327 ($MH^+$) base peak.

1,3-Dimethyl-8-(3-trifluoromethylstyryl)xanthine (20a)

Compound 20a was made from 3-trifluoromethylcinnamic acid. mp>300° C. $^1$H NMR DMSO-$d_6$ d 3.26 (s, 3H N—$CH_3$); 3.48 (s, 3H N—$CH_3$); 7.19 (d, 1H J=16 Hz); 7.64 (t, 1H J=8 Hz); 7.70 (d, 1H J=7 Hz); 7.72 (d, 1H J=16 Hz); 7.94 (d, 1H J=8 Hz); 7.96 (s, 1H). MS (CI) m/e 350 (base), 329, 292.

1,3,7-Trimethyl-8-(3-trifluoromethylstyryl)xanthine (20b)

Compound 20b was made from 20a. mp 232°–236° C. $^1$H NMR DMSO-$d_6$ d 3.25 (s, 3H N—$CH_3$); 3.49 (s, 3H N—$CH_3$); 4.09 (s, 3H $N_7$—$CH_3$); 7.58 (d, 1H J=16 Hz); 7.67 (t, 1H J=8 Hz); 7.72 (d, 1H J=8 Hz); 7.78 (d, 1H J=16 Hz); 8.09 (d, 1H J=7 Hz); 8.26 (s,1H). MS (EI) m/e 364.

1,3-Dimethyl-8-(3-nitrostyryl)xanthine (21a)

Compound 21a was made from 3-nitrocinnamic acid (temperature raised to 80° C. for 3 h, recrystallized from methanol). mp>300° C. $^1$H NMR DMSO-$d_6$ d 3.25 (s, 3H N—$CH_3$); 3,48 (s, 3H N—$CH_3$); 7.22 (d, 1H J=16 Hz); 7.70 (t, 1H J=8 Hz); 7.76 (d,1H J=16 Hz); 8.10 (d, 1H J=8 Hz); 8.18 (d. 1H J=8 Hz); 8.41 (s, 1H). MS (EI) m/e327 (base), 310, 280.

1,3,7-Trimethyl-8-(3-nitrostyryl)xanthine (21b)

Compound 21b was made from 21a. mp 306°–308° C. $^1$H NMR DMSO-$d_6$ d 3.23 (s, 3H N—$CH_3$); 3.47 (s, 3H N—$CH_3$); 4.08 (s, 3H $N_7$—$CH_3$); 7.63 (d, $^1$H J=16 Hz); 7.71 (t, 1H J=8 Hz); 7.80 (d, 1H J=16 Hz); 8.18 (d, 1H J=8 Hz); 8.23 (d, 1H J=8 Hz); 8.70 (s, 1H). MS (EI) m/e 341 (base); 294.

1,3-Dimethyl-8-(3-aminostyryl)xanthine (22a)

Compound 22a was made from 21a reducing with Zn/acetic acid for 3 h. mp>300° C. $^1$H NMR DMSO-$d_6$ d 3.24 (s, 3H N—$CH_3$); 3.46 (s, 3H N—$CH_3$); 5.19 (s, 2H —$NH_2$); 6.56 (d, 1H J=8 Hz); 6.74 (d, 1H J=8 Hz); 6.76 (s, 1H); 6.84 (d, 1H J=16 Hz); 7.05 (t, 1H J=8 Hz); 7.49 (d, 1H J=16 Hz). MS (CI/$NH_3$) m/e 315 (M+$NH_4^+$), 298 ($MH^+$, base).

1,3,7-Trimethyl-8-(3-aminostyryl)xanthine (22b)

Compound 22b was made from 21b using Zn/acetic acid as reducing agent for 3 h. mp 222°–224° C. $^1$H NMR DMSO-$d_6$ d 3.22 (s, 3H N—$CH_3$); 3.46 (s, 3H N—$CH_3$); 4.00 (s, 3H $N_7$—$CH_3$); 5.14 (s, 2H —$NH_2$); 6.58 (d, 1H J=8 Hz, H-4); 6.87 (s, 1H, H-2); 6.92 (d, 1H J=8 Hz, H-6); 7.07 (t, 1H J=8 Hz, H-5); 7.14 (d, 1H J=16 Hz); 7.51 (d, 1H J=16 Hz). MS (CI/$NH_3$) m/e 312 ($MH^+$).

1,3,7-Trimethyl-8-(3-acetylaminostyryl)xanthine (23)

Compound 23 was made from 22b with acetic anhydride in DMF and DMAP for 1 h. mp>300° C. $^1$H NMR DMSO-$d_6$ d 2.06 (s, 3H —$COCH_3$), 3.23 (s, 3H N—$CH_3$); 3.47 (s, 3H N—$CH_3$); 4.03 (s, 3H $N_7$—$CH_3$); 7.24 (d, 1H J=16 Hz); 7.34 (t, 1H J=8 Hz); 7.50 (t, 1H J=8 Hz); 7.54 (d, 1H J=8 Hz); 7.61 (d, 1H J=16 Hz); 7.86 (s, 1H). MS (CI/$NH_3$) m/e 354 ($MH^+$).

1,3,7-Trimethyl-8-(3-succinylaminostyryl)xanthine (24)

Compound 24 was made from 22b with succinic anhydride in DMF and DMAP. mp>300° C. $^1$H NMR DMSO-d$_6$ d 2.28 (t, 2H J=7 Hz); 2.43 (t, 2H J=7 Hz); 3.23 (s, 3H N—CH$_3$); 3.47 (s, 3H N—CH$_3$); 4.03 (s, 3H N$_7$—CH$_3$); 7.24 (d, 1H J=16 Hz); 7.32 (t, 1H J=8 Hz); 7.45 (d, 1H J=8 Hz); 7.54 (d, 1H J=8 Hz); 7.61 (d, 1H J=16 Hz); 7.82 (s, 1H). MS (CI/NH$_3$) m/e 394 (M—OH), 312, 209 (base). UV characteristics: $\lambda_{max}$ in methanol 349 nm, log e=4.48. The maximal aqueous solubility following dissolution in K$_2$HPO$_4$ (0.1M) was determined to be 19 mM.

1,3,7-Trimethyl-8-(3-tert-butyloxycarbonyl aminostyryl)xanthine (25)

Compound 25 was made from 22b with di-tert-butyl dicarbonate and DMAP in DMF. mp>300° C. $^1$H NMR DMSO-d$_6$ d 1.40 (s, 9H CH$_3$COO); 3.17 (s, 3H N—CH$_3$); 3.41 (s, 3H N—CH$_3$); 3.89 (s, 3H N7-CH$_3$); 7.23 (d, 1H J=16 Hz); 7.33 (d, 1H J=8 Hz); 7.51 (t, 1H J=8 Hz); 7.57 (s, 1 H); 7.67 (d, 1H J=16 Hz); 7.75 (d, 1H J=8 Hz). MS (CI/NH$_3$) 414 (M—CH$_3$+NH$_4^+$, base), 338, 314, 312.

1,3,7-Trimethyl-8-[3-[di-(tert-butyloxycarbonyl)amino]styryl]xanthine (26)

Compound 26 was made from 22b with Di-tert-butyl dicarbonate and DMAP in DMF. mp 175°–177° C. $^1$H NMR DMSO-d$_6$ d 1.39 (s, 18H CH$_3$COO); 3.23 (s, 3H N—CH$_3$); 3.46 (s, 3H N—CH$_3$); 4.03 (s, 3H N$_7$—CH$_3$); 7.17 (d, 1H J=8 Hz); 7.42 (t, 1H J=8 Hz); 7.43 (d, 1H J=16 Hz); 7.67 (d, 1H J=16 Hz); 7.69 (d, 1H J=8 Hz); 7.74 (s, 1H). MS (CI/NH$_3$) 514 (M—CH$_3$+NH$_4^+$); 414 (base).

1,3-Dimethyl-8-(4-methoxystyryl)xanthine (29a)

Compound 29a was made from 4-methoxycinnamic acid, m.p.>320° C. $^1$H NMR DMSO-d$_6$ 3.24 (s, 3H N$_3$CH$_3$); 3.46 (s, 3H N$_7$—CH$_3$); 3.78 (s, 3H OCH$_3$); 6.85 (d, 1H, J=16 Hz); 7.0 (d, 2H, J=8 Hz); 7.55 (d, 2H, J=8 Hz); 7.6 (d, 1H, J=16 Hz). MS (CI/NH$_3$) m/e 313 (MH$^+$, base) 172.

1,3,7-Trimethyl-8-(4-methoxystyryl)xanthine (29b)

Compound 29b was made from 29a, m.p.>320° C. $^1$H NMR DMSO-d$_6$ d 3.22 (s, 3H N$_3$CH$_3$); 3.45 (s, 3H N$_7$CH$_3$); 3.8 (s, 3H OCH$_3$); 4.0 (s, 3H, N$_7$CH$_3$); 7.0 (d, 1H, J=8 Hz); 7.2 (d, 1H, J=16 Hz); 7.66 (d, 1H, J=16 Hz), 7.72 (d, 1H, J=8 Hz). MS (CI/NH$_3$) m/e 327 (MH$^+$, base) 205.

1,3-Dimethyl-8-(4-dimethylaminostyryl)xanthine (30a)

A solution of 4-dimethylaminocinnamic acid (0.1 g, 0.52 mmol), 1-hydroxy benzotriazole (0.14 g, 1.04 mmol) and EDAC (0.19 g, 1.04 mmol) in DMF (1 ml) was sonicated for 1 h. 1,3-Dimethyl-5,6-diaminouracil (0.088 g, 0.52 mmol) was added and the mixture was heated for 3 h at 80° C. The dark red solution was cooled to room temperature and the product was obtained as a deep yellow precipitate (0.045 g). An additional crop was obtained by cooling the mother liquor in an ice bath and adding 10 volumes of brine (combined yield 38%). $^1$H NMR CD$_3$OD d 7.54 (d, 1H, J=15.5 Hz), 7.45 (d, 2H, 8.8 Hz), 6.74 (d, 2H, J=8.8 Hz), 6.56 (d, 1H, J=15.5 Hz), 3.42, 3.27 (s, 3H, CH$_3$), 3.00 (s, 6H, N(CH$_3$)$_2$). MS (CI) m/e 344 (MH$^+$).

The above amide (0.045 g, 0.13 mmol) was suspended in methanol (1 ml) and 4N NaOH (1 ml) was added. The resulting solution was stirred at 80°–90° C. for 1.5 h. 18% HCl was added carefully to the ice cooled reaction solution to pH 7–8. A yellow precipitate was obtained (0.018 g, 43%). 1H NMR DMSO-d$_6$ d 7.54 (d, 1H, J=16 Hz), 7.44 (d, 2H, J=8.5 Hz), 6.74 (d, 2H, J=16 Hz), 6.738 (d, 2H, J=16 Hz), 3.47, 3.25 (s, 3H, CH$_3$), 2.97 (s, 6H, N(CH$_3$)$_2$). MS (CI) m/e 326 (MH$^+$).

1,3-Dimethyl-8-(2,3-dimethoxystyryl)xanthine (31a)

Compound 31a was made from 2,3-dimethoxycinnamic acid (recrystallized from methanol). mp 299°–301° C. $^1$H NMR DMSO-d$_6$ d 3.25 (s, 3H N$_3$—CH$_3$); 3.47 (s, 3H N—CH$_3$); 3.78 (s, 3H OCH$_3$); 3.82 (s, 3H OCH$_3$); 7.05 (d, 1H J=17 Hz); 7.05 (dd, 1H J=2 Hz J=8 Hz); 7.11 (t, 1H J=8 Hz); 7.26 (dd, 1H J=2 Hz J=8 Hz); 7.84 (d, 1H J=17 Hz). MS (CI/NH$_3$) m/e 360 (M+NH$_4^+$), 343 (base peak).

1,3,7-Trimethyl-8-(2,3-dimethoxystyryl)xanthine (31b)

Compound 31b was made from 31a, mp 233°–235° C. $^1$H NMR DMSO-d$_6$ d 323 (s, 3H N—CH$_3$); 3.47 (s, 3H N—CH$_3$); 3.78 (s, 3H O—CH$_3$); 3.83 (s, 3H O—CH$_3$); 4.02 (s, 3H N$_7$—CH$_3$); 7.06 (d, 1H J=8 Hz); 7.10 (t, 1H J=8 Hz); 7.32 (d, 1H J=16 Hz); 7.51 (d, 1H J=8 Hz); 7.90 (d, 1H J=16 Hz). MS (EI) m/e 356 (base); 325.

1,3-Dimethyl-8-(3,4-dimethoxystyryl)xanthine (32a)

Compound 32a was made from 3,4-dimethoxycinnamic acid, mp>320° C. $^1$H NMR DMSO-d$_6$ d 3.25 (s, 3H N$_3$CH$_3$); 3.46 (s, 3H N$_7$—CH$_3$); 3.78 (s, 3H OCH$_3$); 3.82 (s, 3H, OCH$_3$), 6.96 (d, 1H, J=16 Hz); 6.98 (d, 1H, J=8 Hz); 7.14 (d, 1H, J=8 Hz); 7.25 (s, 1H). MS (CI/NH$_3$) m/e 343 (MH$^+$, 172 (base peak).

1,3,7-Trimethyl-8-(3,4-dimethoxystyryl)xanthine (32b)

Compound 32b was made from 32a, mp 230°–232° C. $^1$H NMR DMSO-d$_6$ d 3.29 (s, 3H N$_3$—CH$_3$); 3.52 (s, 3H N$_7$CH$_3$); 3.85 (s, 3H OCH$_3$); 3.9 (s, 3H, OCH$_3$), 4.09 (s, 3H, N$_7$CH$_3$); 7.05 (d, 1H, J=8 Hz); 7.25 (d, 1H, J=16 Hz); 7.30 (d, 1H, J=8 Hz), 7.48 (s, 1H), 7.66 (d, 1H, J=16 Hz). MS (CI) m/e 357 (MH$^+$ base), 209.

1,3-Dimethyl-8-(3,5-dimethoxystyryl)xanthine (33a)

Compound 33a was made from 3,5-dimethoxycinnamic acid, mp>320° C. $^1$H NMR DMSO-d$_6$ d 3.24 (s, 3H N$_3$CH$_3$); 3.46 (s, 3H N$_7$CH$_3$); 3.78 (s, 6H OCH$_3$); 6.5 (s, 1H), 6.78 (s, 2H), 7.02 (d, 1H, J=16 Hz); 7.54 (d, 1H, J=16 Hz). MS (CI) m/e 343 (MH$^+$ base), 166, 136.

1,3,7-Trimethyl-8-(3,5-dimethoxystyryl)xanthine (33b)

Compound 33b was made from 33a, mp 228°–230° C. $^1$H NMR DMSO-d$_6$ d 3.22 (s, 3H N$_3$CH$_3$); 3.45 (s, 3H N$_3$CH$_3$); 3.79 (s, 6H OCH$_3$); 4.04 (s, 3H, N$_7$CH$_3$), 6.5 (s, 1H), 6.97 (s, 2H), 7.32 (d, 1H, J=16 Hz), 7.58 (d, 1H, J=16 Hz).

1,3,7-Trimethyl-8-(3,5-dimethoxy-4-benzyloxystyryl) xanthine (37)

Compound 37 was made from benzyl bromide, mp 190°–195° C. $^1$H NMR CDCl$_3$ d 3.42 (s, 3H N$_3$CH$_3$), 3.63 (s, 3H N$_5$CH$_3$); 3.89 (s, 6H OCH$_3$); 5.06 (s, 2H, OCH$_2$), 6.8 (s, 2H); 6.78 (d, 1H, J=16 Hz); 7.3–7.5 (m, 5H); 7.7 (d, 1H, J=16 Hz). MS (CI) m/e 463 (MH$^+$ base), 375, 357.

1,3,7-Trimethyl-8-[3,5-dimethoxy-4-[4-aminobutyloxy]styryl]xanthine (38)

Compound 38 was made from 1,4-dibromobutane. MS (CI) m/e 444 (MH+ base), 373, 359.

1,3,7-Trimethyl-8-[3,5-dimethoxy-4-[4-(tert-butyloxycarbonylamino)butyloxy]styryl]xanthine (39)

Compound 39 was made from 38 using di-tert-butyl dicarbonate in $CHCl_3$ (30 min). The chloroform was removed under a stream of $N_2$, and the crude product was purified using a preparative plate (silica, ethyl acetate/petroleum ether 70:30). $^1H$ NMR $CDCl_3$ d 1.41 (s, 9H $CH_3$), 1.6–1.8 (m, 4H, $CH_2$), 3.2 (m, 2H $CH_2NH$), 4.0 (m, 2H, $OCH_2$), 3.39 (s, 3H, $N_3CH_3$), 3.6 (s, 2H, $N_7CH_3$), 3.88 (s, 6H, $OCH_3$, 4.05 (s, 3H, $N_7CH_3$), 6.74 (s, 2H), 6.75 (d, 1H, J=16 Hz), 7.7 (d, 1H, J=16 Hz). MS (CI) m/e 544 (MH+ base) 44, 359.

1,3,7-Trimethyl-8-[3,5-dimethoxy-4-[4-(aminobutyloxy) styryl]xanthine (40)

Compound 40 was made from 1,4-dibromo-trans-2-butene. $^1H$ NMR $CDCl_3$ d 3.41 (s, 3H $N_3CH_3$); 3.63 (s, 3H $N_7CH_3$); 3.91 (s, 6H $OCH_3$); 4.06 (s, 3H, $N_7CH_3$); 4.43 (s, 2H, $CH_2NH_2$); 5.94 (s, 2H, $OCH_6$); 6.78 (s, 2H), 6.79 (d, 1H, J=16 Hz). MS (CI) m/e 442 (MH+ base) 373,357,124.

7-Ethyl-1,3-trimethyl-8-[3,4,5-trimethoxystyryl] xanthine (44c)

Compound 44c was made from compound 44a, except that ethyl iodide was used during methylation, instead of methyl iodide. $^1H$ NMR $DMSO,d_6$ d 1.34 (t, 3H, $CH_3$ Et, J=7 Hz); 3.25 and 3.47 (each s, 3H $NCH_3$); 3.70 (s, 4H 4-$OCH_3$); 3.86 (s, 6H 3,5-di-$OCH_3$); 4.54 (q, 2H, N7-$CH_2$); 7.13 (s, 2H, Ar), 7.30 and 7.68 (each d, 1H, C=C, J=16 Hz).

1,3-Dipropyl-7-methyl-8-styrylxanthine (47)

5-Amino-6-nitroso-1,3-dipropyluracil was suspended in DMF (10 mmol/100 ml) and hydrogenated over 5% Pd/C at 40 psi overnight. The clear solution was filtered through Celite and could be stored at −20° C.

Trans-cinnamic acid (0.47 g) and EDAC (0.65 g) were added to 2.1 mmol of the above solution and stirred for 4 h. An additional 0.3 g of EDAC was added. After 2 additional h, half-saturated NaCl solution was added and the mixture was extracted with ethyl acetate (6x). The organic layer was dried over $Na_2SO_4$ and evaporated to an oil, which was used without further purification.

The above oil was dissolved in methanol (30 ml) and treated with 4N NaOH (20 ml). After refluxing for 15 min, the mixture was cooled, ice was added, and it was acidified using 6N HCl. A precipitate formed and was recovered by filtration. The NMR and MS were consistent with the assigned structure of 47. Recrystallized from DMF/water.

$e_{342}$ for 47 in methanol ($\lambda_{max}$) was 35,100. A smaller absorption peak was at 265 nm.

1,3,7-Trimethyl-8-[2-(3-aminophenyl)ethyl]xanthine (57)

Compound 54 was made from 21b with $H_2$/Pd 50 psi in DMF for 3 h. mp 158°–160° C. $^1H$ NMR $DMSO-d_6$ d 2.82 (t, 2H J=8 Hz); 2.96 (t, 2H J=8 Hz); 3.20 (s, 3H N—$CH_3$); 3.42 (s, 3H N—$CH_3$); 3.69 (s, 3H $N_7$—$CH_3$); 4.95 (s, 2H —$NH_2$); 6.34–6.39 (3H, H-2 H-4 H-6); 6.90 (t, 1H J=8 Hz, H-5). MS (CI/$NH_3$) m/e 314 (MH+).

The physical characteristics and elemental analyses of the xanthine derivatives are summarized in Table II.

TABLE II

Characterization of xanthine derivatives and elemental analysis.

| Compd. | Yield % | mp (°C.) | Formula | Calculated: C | H | N | Found: C | H | N |
|---|---|---|---|---|---|---|---|---|---|
| 15a. | 51 | >280 | $C_{15}H_{14}N_{14}N_4O_2 \cdot \frac{1}{2}H_2O$ | 61.85 | 5.19 | 19.23 | 62.42 | 5.12 | 18.78[b] |
| 15b. | 81 | 220–222 | $C_{16}H_{16}N_4O_2 \cdot \frac{1}{4}H_2O$ | 63.88 | 5.53 | 18.62 | 63.93 | 5.68 | 17.60[b] |
| 16. | 57 | >280 | $C_{15}H_{13}N_4O_2F$ | 60.00 | 4.36 | 18.66 | 60.02 | 4.37 | 18.66 |
| 17a. | 31 | >300 | $C_{16}H_{16}NO_3 \cdot \frac{2}{3}H_2O$ | 60.14 | 5.30 | 17.53 | 60.44 | 5.13 | 17.11 |
| 17b. | 74 | 238–240 | $C_{17}H_{18}N_4O_3$ | 62.57 | 5.56 | 17.17 | 62.41 | 5.58 | 17.09 |
| 18. | 3 | >300 | $C_{15}H_{14}N_4O_3$ | 60.40 | 4.73 | 18.78 | | | |
| 19a. | 65 | >280 | $C_{16}H_{16}N_4O_3$ | | | | | | |
| 19b. | 61 | 212–215 | $C_{17}H_{18}N_4O_3 \cdot \frac{1}{2}H_2O$ | 60.89 | 5.71 | 16.71 | 60.93 | 5.83 | 15.86[b] |
| 20a. | 55 | >300 | $C_{16}H_{13}N_4O_2F_3$ | 54.86 | 3.74 | 15.99 | 54.74 | 3.76 | 15.84 |
| 20b. | 84 | 232–236 | $C_{17}H_{15}N_4O_2F_3 \cdot \frac{1}{2}H_2O$ | 54.69 | 4.32 | 15.01 | 54.93 | 4.15 | 14.81 |
| 21a. | 56 | >300 | $C_{15}H_{13}N_4O_4$ | 55.05 | 4.00 | 21.40 | 55.06 | 4.08 | 21.22 |
| 21b. | 84 | 306–308 | $C_{16}H_{15}N_4O_4$ | 56.30 | 4.43 | 20.52 | 56.31 | 4.50 | 20.46 |
| 22a. | 85 | >300 | $C_{15}H_{15}N_5O_2 \cdot \frac{1}{2}H_2O$ | 58.82 | 5.27 | 22.86 | 59.03 | 5.25 | 22.65 |
| 22b. | 92 | 222–224 | $C_{16}H_{17}N_5O_2 \cdot 0.85H_2O$ | 58.83 | 5.77 | 21.44 | 58.93 | 5.87 | 21.37[c] |
| 23. | 77 | >300 | $C_{18}H_{19}N_5O_3 \cdot \frac{3}{5}H_2O$ | 59.36 | 5.59 | 19.23 | 59.21 | 5.48 | 18.99[c] |
| 24. | 78 | >300 | $C_{20}H_{21}N_5O_5 \cdot 0.7H_2O$ | 56.65 | 5.33 | 16.52 | 56.96 | 5.23 | 16.18[c] |
| 25. | 59 | >300 | $C_{21}H_{25}N_4O_4 \cdot \frac{1}{2}H_2O$ | 59.99 | 6.23 | 16.66 | 59.94 | 5.87 | 16.00[b,c] |
| 26. | 27 | 175–177 | $C_{26}H_{33}N_5O_6 \cdot \frac{2}{3}H_2O$ | 60.20 | 6.57 | 13.50 | 61.47 | 6.57 | 13.05c |
| 27a. | 87 | >310 | $C_{15}H_{13}N_4O_2F \cdot \frac{1}{2}H_2O$ | 58.25 | 4.56 | 18.11 | 58.68 | 4.39 | 17.58[b,c] |
| 27b. | 75 | 208–209 | $C_{16}H_{15}N_4O_2F$ | 61.14 | 4.81 | 17.82 | 61.07 | 4.80 | 17.73 |
| 28. | 10 | 205 | $C_{16}H_{15}N_4O_2Cl$ | 58.10 | 4.57 | 16.94 | 58.18 | 4.55 | 16.89 |
| 29a. | 4 | >320 | $C_{16}H_{16}N_4O_3$ | 61.53 | 5.16 | 17.94 | 61.35 | 5.11 | 17.89 |
| 29b. | 55 | 220–222 | $C_{17}H_{18}N_4O_3$ | 62.57 | 5.56 | 17.17 | 62.43 | 5.58 | 17.08[c] |
| 30a. | 43 | >230 | $C_{17}H_{19}N_5O_2$ | | | | | | c |
| 30b. | 29 | >230 | $C_{18}H_{21}N_5O_2$ | 63.70 | 6.24 | 20.63 | 64.10 | 6.55 | 18.15[b,c] |
| 31a. | 32[a] | 299–301 | $C_{17}H_{18}N_4O_4$ | 59.64 | 5.30 | 16.37 | 59.60 | 5.34 | 16.29 |
| 31b. | 49 | 233.5–235 | $C_{18}H_2ON_4O_4 \cdot \frac{1}{2}H_2O$ | 59.17 | 5.79 | 15.33 | 59.45 | 5.64 | 15.30 |
| 32a. | 4 | >295 | $C_{17}H_{18}N_4O_4$ | 59.64 | 5.30 | 16.37 | 59.55 | 5.28 | 16.31[c] |

TABLE II-continued

Characterization of xanthine derivatives and elemental analysis.

| Compd. | Yield % | mp (°C.) | Formula | Calculated: C | H | N | Found: C | H | N |
|---|---|---|---|---|---|---|---|---|---|
| 32b. | 63 | 230–232 | $C_{18}H_2ON_4O_4·½H_2O$ | 59.17 | 5.79 | 15.33 | 59.15 | 5.73 | 15.23 |
| 33a. | 18 | >320 | $C_{17}H_{18}N_4O_4$ | 59.64 | 5.30 | 16.37 | 59.56 | 5.34 | 16.35 |
| 33b. | 63 | 228–230 | $C_{18}H_2ON_4O_4$ | 60.67 | 5.66 | 15.72 | 60.60 | 5.67 | 15.65 |
| 34a. | 76 | >310 | $C_{15}H_{12}N_4O_2F_2$ | 56.61 | 3.80 | 17.60 | 56.66 | 3.85 | 17.51 |
| 34b. | 87 | 238–239 | $C_{16}H_{14}N_4O_2F_2·¾H_2O$ | 55.57 | 4.52 | 16.20 | 55.94 | 4.64 | 16.15 |
| 35. | 54 | 269$^d$ | $C_{20}H_{22}N_4O_6$ | 58.06 | 5.41 | 15.05 | 57.79 | 5.48 | 14.95$^c$ |
| 36. | 57 | 274–279 | $C_{18}H_2ON_4O_5·¼H_2O$ | 57.34 | 5.41 | 13.37 | 57.18 | 5.33 | 13.46$^c$ |
| 37. | 75 | 190–194 | $C_{25}H_{26}N_4O_5·½H_2O$ | 63.68 | 5.77 | 11.88 | 63.51 | 5.71 | 11.47 |
| 38. | 90$^e$ | 207–212 | $C_{22}H_{29}N_5O_5$ | | | | | | c |
| 39. | 15$^d$ | 184.5–186.5 | $C_{27}H_{37}N_5O_7·0.5H_2O$ | 58.68 | 6.93 | 12.67 | 58.54 | 6.84 | 12.30$^c$ |
| 40. | 18 | 200–206 | $C_{22}H_{27}N_5O_5$ | 58.66 | 6.27 | 14.55 | 59.28 | 6.33 | 14.83$^{b,c}$ |
| 41. | 71 | 229–232$^d$ | $C_{24}H_{29}N_5O_6$ | 57.48 | 6.23 | 13.96 | 57.53 | 6.24 | 13.77$^c$ |
| 42. | 75 | 192–195 | $C_{27}H_{35}N_5O_7$ | 59.88 | 6.51 | 12.93 | 59.58 | 6.39 | 12.59$^c$ |
| 43a. | 72 | 165 | $C_{18}H_{20}N_4O_5$ | 58.06 | 5.41 | 15.05 | 58.34 | 5.58 | 14.06$^b$ |
| 43b. | 43 | 189–193 | $C_{19}H_{22}N_4O_5·½H_2O$ | 57.71 | 5.86 | 14.17 | 57.59 | 5.88 | 13.37$^b$ |
| 44a. | 63 | >280 | $C_{18}H_{20}N_4O_5$ | 58.06 | 5.41 | 15.05 | 57.99 | 5.46 | 14.99 |
| 44b. | 82 | 245–247 | $C_{19}H_{22}N_4O_5$ | 59.06 | 5.74 | 14.50 | 58.99 | 5.75 | 14.49 |
| 44c. | 84 | 225–229 | $C_{20}H_{24}N_4O_5$ | 59.99 | 6.04 | 13.99 | 60.00 | 6.08 | 13.90 |
| 44d. | 70 | 251–254 | $C_{20}H_{24}N_4O_2$ | 57.69 | 5.81 | 13.45 | 57.59 | 5.77 | 13.40 |
| 44e. | 79 | 235–237 | $C_{21}H_{22}N_4O_5$ | 61.46 | 5.40 | 13.65 | 61.43 | 5.67 | 13.53 |
| 44f. | 71 | 215–218 | $C_{26}H_{28}N_4O_5$ | 65.53 | 5.92 | 11.76 | 65.32 | 5.91 | 11.64 |
| 45a. | 20$^a$ | 286–289 | $C_{20}H_{24}N_4O_5·¼H_2O$ | 59.32 | 6.10 | 13.84 | 59.69 | 5.98 | 13.56$^c$ |
| 45b. | 64 | 207–210 | $C_{21}H_{26}N_4O_5$ | 60.86 | 6.32 | 13.52 | 60.68 | 6.34 | 13.45$^c$ |
| 47. | 52$^a$ | 257–260 | $C_{19}H_{22}N_4O_2$ | 67.44 | 6.55 | 16.56 | 67.52 | 6.58 | 16.49 |
| 48. | 91 | 215–217 | $C_{20}H_{23}N_4O_4$ | 60.44 | 5.83 | 17.62 | 60.66 | 5.97 | 17.38 |
| 49. | 92 | 145–148 | $C_{20}H_{25}N_5O_2·¾H_2O$ | 63.06 | 7.01 | 18.38 | 63.08 | 6.62 | 18.37 |
| 50a. | 61 | 264–265 | $C_{19}H_{21}N_4O_2F$ | 64.03 | 5.94 | 15.72 | 63.89 | 5.97 | 15.65 |
| 50b. | 83 | 155–157 | $C_{20}H_{23}N_4O_2F·¼H_2O$ | 64.07 | 6.32 | 14.94 | 63.97 | 6.26 | 14.89$^c$ |
| 51a. | 18$^a$ | 257–259 | $C_{19}H_{21}N_4O_2Cl$ | 61.21 | 5.68 | 15.03 | 61.31 | 5.74 | 15.09 |
| 51b. | 67 | 164–166 | $C_{20}H_{23}N_4O_2Cl$ | 60.00 | 6.17 | 13.99 | 59.67 | 5.79 | 13.84$^c$ |
| 52a. | 48 | 250–253 | $C_{21}H_{26}N_4O_4·¼H_2O$ | 62.59 | 6.63 | 13.90 | 62.82 | 6.63 | 13.44 |
| 52b. | 78 | 164–164 | $C_{22}H_{28}N_4O_4·¾H_2O$ | 62.03 | 6.98 | 13.15 | 62.26 | 6.75 | 12.79$^c$ |
| 53a. | 100 | 150–152 | $C_{21}H_{26}N_4O_4·⅔H_2O$ | 62.18 | 6.66 | 13.81 | 62.54 | 6.41 | 13.44$^c$ |
| 53b. | 59 | 166–167 | $C_{22}H_{28}N_4O_4$ | 64.06 | 6.84 | 13.58 | 64.20 | 6.90 | 13.42$^c$ |
| 54a. | 78 | 275–278 | $C_{19}H_{20}N_4O_2F_2·¾H_2O$ | 58.83 | 5.59 | 14.44 | 59.09 | 5.26 | 14.30 |
| 54b. | 85 | 161–163 | $C_{20}H_{22}N_4O_2F_2·0.9H_2O$ | 59.37 | 5.93 | 13.9 | 59.12 | 5.92 | 14.26 |
| 55a. | 32 | 241–244 | $C_{22}H_{28}N_4O_5$ | 61.67 | 6.59 | 13.08 | 61.59 | 6.61 | 13.04 |
| 55b. | 88 | 107.5–109 | $C_{23}H_{30}N_4O_5$ | 61.43 | 6.83 | 12.66 | 62.16 | 6.85 | 12.60 |
| 56a. | 11 | 252–254 | $C_{22}H_{28}N_4O_5$ | 61.67 | 6.59 | 13.08 | 61.56 | 6.61 | 13.06 |
| 56b. | 82 | 193–194 | $C_{23}H_{30}N_4O_5·½H_2O$ | 61.18 | 6.92 | 12.41 | 61.44 | 6.80 | 12.44 |
| 57. | 67 | 158–160 | $C_{16}H_{19}N_5O_2$ | 61.33 | 6.11 | 22.35 | 61.40 | 6.14 | 22.32$^c$ |
| 58a. | 78 | >280 | $C_{16}H_{14}N_4O_4·½H_2O$ | 57.31 | 4.51 | 16.71 | 57.51 | 4.42 | 16.46 |
| 58b. | 99 | 273–275 | $C_{17}H_{16}N_4O_4$ | 60.00 | 4.74 | 16.46 | 59.88 | 4.86 | 16.26 | a. Yield calculated from 1,3-dialkyl-6-amino-5-nitrosouracil.
b. Analyses: % N found (calcd.) 15b, 17.60 (18.62); 19b, 15.86 (16.71); 25, 16.00 (16.66); 27a, 17.58 (18.11); 30b, 18.15 (20.63); 43a, 14.06 (15.06); 43b, 13.37 (14.17); % C found (calcd.) 15a, 62.42 (61.85); 40, 58.66 (59.28).
c. Accurate mass, measured (ppm from calculated), in EI mode, unless noted: 18, 298.1055 (–3.7); 22b, 311.1373 (5.6); 23, 353.1483 (–1.4); 24, 411.1556 (3.2); 25 411.1894 (–3.1); 26, 511.2450 (3.7); 27a, 300.1018 (2.3); 29b, 326.1371 (–2.4); 30a, 325.1537 (–0.5); 30b, 339.1688 (–4.1); 32a, 342.1326 (–0.6); 35, 372.1436 (0.7); 36, 414.1543 (0.9); 38 (FAB), 444.2255 (0.8); 39, 543.2684 (–1.7); 40, 441.2001 (–2.5); 41, 483.2131 (2.7); 42, 541.2544 (1.4); 45a (FAB), 401.1812 (–1.3); 45b, 414.1898 (–1.3); 50b, 370.1795 (–2.7); 51b, 386.1492 (–4.5); 52b, 412.2110 (–0.1); 53a, 398.1937 (–4.3); 53b, 412.2093 (–4.3); 57, 313.1521 (–5.7).
d. From compound 44b.
e. From compound 39.

EXAMPLE 2

This example describes the use of a palladium-catalyzed Heck reaction to attach an 8-vinyl or 8-styryl group to a xanthine.

Figure 3:
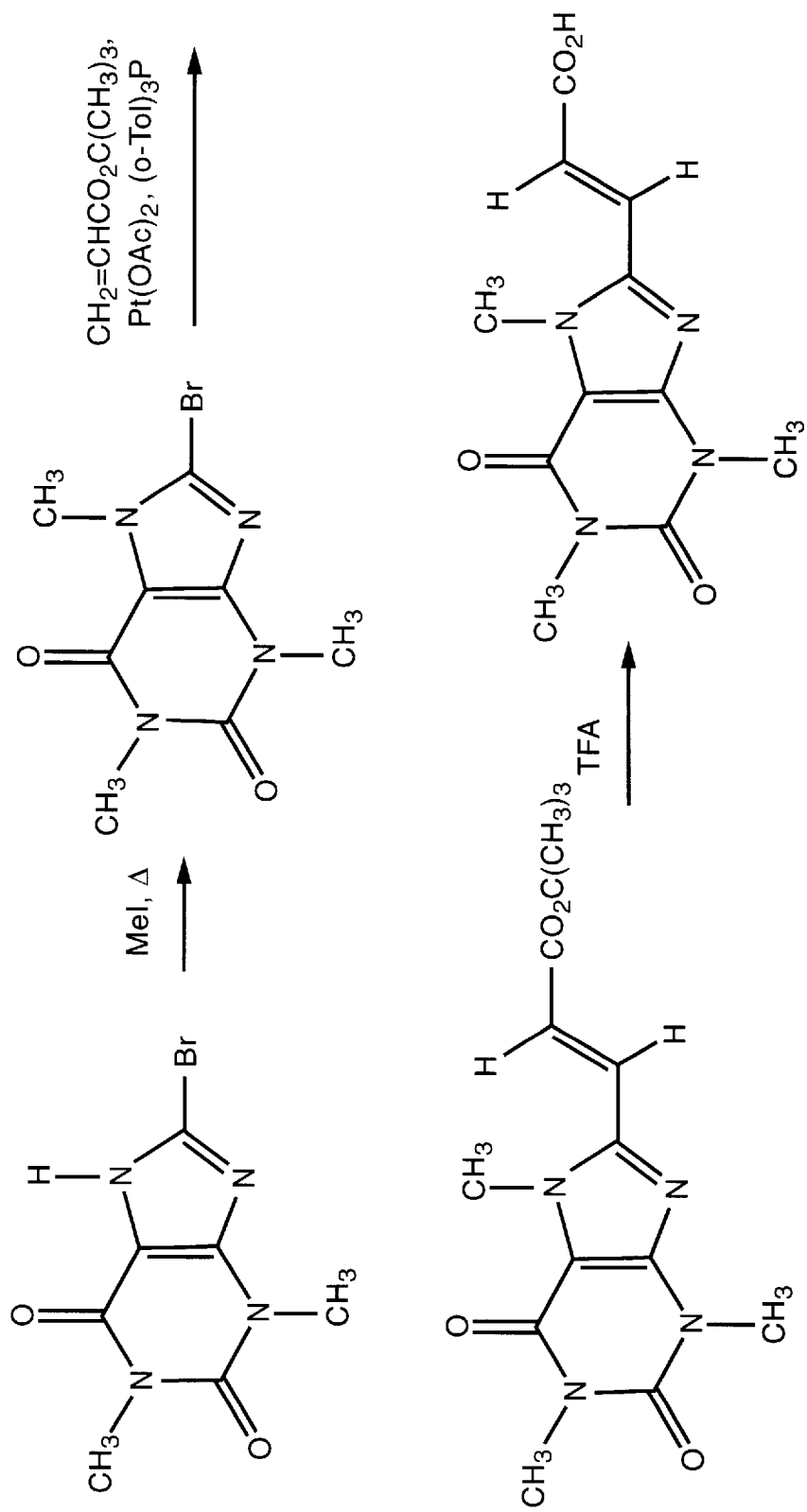
FIG. 3 is a schematic diagram, which shows the use of a palladium-catalyzed Heck reaction to attach an 8-vinyl or 8-styryl group to a xanthine.

8-styryl- and 8-vinyl-xanthine derivatives were synthesized as shown in FIG. 3. FIG. 3 is a schematic diagram of the synthesis, wherein methyl iodide and heat were used in the first step, $CH_2=CHCO_2C(CH_3)_3$, $Pt(OAc)_2$, and (o-Tol)$_3$P were used in the second step, and trifluoroacetic acid (TFA) was used in the last step.

For example, a mixture of 8-bromo-caffeine (450 mg, 1.65 mmol), tert-butylacrylate (0.390 ml, 2.69 mmol), $Pd(AcO)_2$ (3.7 mg, 16.5 μmol), tri-o-tolylphosphine (20 mg, 66 μmol), triethylamine (2 ml) and acetonitrile (2 ml) was warmed at 100° C. for 16 h with stirring in a capped tube. After cooling to room temperature, $CHCl_3$ was added and the mixture was filtered. The organic layer was extracted twice with 1N HCl, washed with brine several times, dried ($MgSO_4$), and then evaporated to dryness. The residue was created with MeOH (1 ml), and hexane was added, to afford 152 mg of the crystalline product 8-(trans-2-tert-Butyloxycarbonylvinyl)-1,3,7-trimethylxanthine. The mother liquors were evaporated, and the remaining product was purified by preparative TLC (hexane:ethyl acetate 1:1)

to give 49 mg (38% overall). mp: 214°–215° C. $^1$H NMR DMSO-d$_6$: d 1.48 (s, 9H, CH$_3$), 3.22 (s, 3H, NCH$_3$), 3.42 (s, 3H, NCH$_3$), 4.03 (s, 3H, N$_7$CH$_3$), 6.73 (d, 1H, J=15 Hz), 7.51 (d, 1H, J=15 Hz). MS (CI NH$_3$) m/e 321 (MH$^+$).

8-(trans-2-tert-Butyloxycarbonylvinyl)-1,3,7-trimethylxanthine (76 mg, 238 μmol) was dissolved in 3 ml TFA and stirred for 1 h. After evaporation, the residue was triturated with ether to provide the pure product 8-(trans-2-Carboxyvinyl)-1,3,7-trimethylxanthine (55 mg, 88% yield). mp: 278d °C. $^1$H NMR DMSO-d$_6$: d 3.27 (s, 3H, NCH$_3$), 3.44 (s, 3H, NCH$_3$), 4.02 (s, 3H N$_7$CH$_3$), 6.78 (d, 1H, J=15.4 Hz), 7.55 (d, 1H, J=15.4 Hz), 8.4 (br s, 1H, COOH). MS (CI NH$_3$) m/e 265 (MH$^+$). Alternatively, compound 8-(trans-2-Carboxyvinyl)-1,3,7-trimethylxanthine was prepared from 8-(trans-2-tert-Butyloxycarbonylvinyl)-1,3,7-trimethylxanthine in DMF/water (1:1) solution by saponification with sodium hydroxide in 49% yield.

TABLE III

Affinities of 8-styryl xanthine derivatives radioligand binding assays at rat brain A$_1$ and A$_2$ receptors,[a] wherein R$_1$, R$_3$, and R$_7$ are methyl, and R$_β$ is hydrogen or methyl

| X = | K$_i$(A$_1$)[a] | K$_i$(A$_2$)[a] | A$_1$/A$_2$ ratio |
|---|---|---|---|
| n-propyl(R$_β$ = H) | 6,000 | 1,600 | 3.8 |
| C(=O)OC(CH$_3$)$_3$ (R$_β$ = H) | 18,000 | 590 | 31 |
| C(=O)OH(R$_β$ = H) | >100,000 | 30,000 | >3 |
| phenyl (R$_β$ = Me) | 8,680 ± 2300 | 1,420 ± 160 | 6 |
| C(=O)NH-phenyl(R$_β$ = H) | 50,000 | 2,530 ± 520 | 19.8 | a. Expressed in nM (single determination or mean ± S.E.M. for 3 or more determinations) vs. [$^3$H]PIA (1 nM) at rat A$_1$-receptors and vs. [$^3$H]CGS21680 (5 nM) at rat striatal A$_2$-receptors.

EXAMPLE 3

This example describes a radioligand binding assay, which was used to assess the affinity of the 1,3,7-trialkyl-8-substituted xanthine compounds for adenosine receptors.

The 1,3,7-trialkyl-8-substituted xanthine compounds of the present invention were tested in a radioligand binding assay for affinity at adenosine receptors in rat brain membranes. The compounds were assayed for affinity at rat A$_1$ cortical receptors using [$^3$H]N$^6$-phenylisopropyladenosine (Schwabe et al., *Naunyn-Schmiedenberg's Arch. Pharmacol.*, 313, 179–187 (1980)) and at rat striatal A$_{2a}$ receptors using [$^3$H]CGS 21680 (Tables I, III, and IV) (Jarvis et al., *J. Pharmacol. Exp. Therap.*, 251, 888–893 (1989)).

Rat cerebral cortical membranes and striatal membranes were prepared (Francis et al., 1980, supra; and Sarges et al., 1990, supra) and treated with adenosine deaminase (2 U/ml) for 30 min at 37° C. prior to storage at −70° C. Solid samples of the adenosine derivatives were dissolved in DMSO and stored in the dark at −20° C. The stock solutions were diluted with DMSO to a concentration of ≧0.1 mM prior to adding to the aqueous medium. The final concentration of DMSO in the assay medium was generally 2%.

Inhibition of binding of 1 nM [$^3$H]N$^6$-phenylisopropyladenosine (Dupont NEN, Boston, Mass.) to A$_1$ receptors in rat cerebral cortex membranes was measured as described (Schwabe et al., 1980, supra). Membranes (~100 μg protein per tube) were incubated for 1.5 h at 37° C. in a total volume of 0.5 ml of 50 mM Tris hydrochloride, at pH 7.4. Test drugs were dissolved in DMSO and added in 10 μl aliquots, resulting in a final DMSO concentration of 2%. Bound and free radioligand were separated by addition of 3 ml of a buffer containing 50 mM Tris hydrochloride, pH 7.4, at 5° C., followed by vacuum filtration using a Brandel Cell Harvester (Brandel, Gaithersburg, Md.) and a Whatman GF/B glass fiber filter with additional washes totaling 9 ml of buffer. Non-specific binding was determined with 10 μM 2-chloroadenosine.

Inhibition of binding of 5 nM [$^3$H]CGS 21680 (2-[4-[(2-carboxyethyl)-phenyl]ethylamino]-5'-N-ethylcarboxamido-adenosine) was carried out as follows. Membranes (~80 μg protein per tube, prepared according to Jarvis et al., 1989, supra) were incubated for one hour at 25° C. in a total volume of 0.5 ml of 50 mM Tris hydrochloride 50 mM, containing 10 mM MgCl$_2$ at pH 7.4. Test drugs were dissolved in DMSO and added in 10 μl aliquots, resulting in a final DMSO concentration of 2%. Non-specific binding was defined using 20 μM 2-chloroadenosine. Filtration was carried out using a Brandel Cell Harvester, as above, using Tris HCl/MgCl$_2$ as the washing buffer.

At least six different concentrations spanning three orders of magnitude, adjusted appropriately for the IC$_{50}$ of each compound, were used. IC$_{50}$ values, computer-generated using a non-linear regression formula on the GraphPAD program (Institute for Scientific Information), were converted to apparent K$_i$ values using K$_D$ values (Francis et al., 1988, supra; and Sarges et al., 1990, supra) of 1.0 and 14 nM for [$^3$H]PIA and [$^3$H]CGS 21680 binding, respectively, and the Cheng-Prusoff equation (Cheng et al., *Biochem. Pharmacol.*, 22, 3099–3108 (1973)).

Small alkyl substituents at the 1 and 3 position were identical and varied from methyl to propyl. Substituents at the 7-position varied from H to 2-phenylethyl. A number of related xanthines (not 8-styryl) were prepared for comparison (Table IV). K$_i$ values of nearly 10$^{-8}$M at A$_2$ receptors and selectivities of hundreds of fold were achieved.

TABLE IV

Affinities of related xanthine derivatives in radioligand binding assays at rat brain A$_1$ and A$_2$ receptors.[a]

| Compound | R$_7$ = | R$_8$ = | K$_i$(A$_1$)[a] | K$_i$(A$_2$)[a] | A$_1$/A$_2$ ratio |
|---|---|---|---|---|---|
| 2. | Me | cyclohexyl | [28,000][b] | 17,100 | 1.6 |
| 57. | Me | 2-(3-amino-phenyl)ethyl | 15%[c](10$^{-5}$) | 18,000 | |
| 58a. | H | 7-methoxybenzofuran-2-yl | 1,700 ± 70 | 3,900 ± 940 | 0.5 |
| 58b. | Me | 7-methoxybenzofuran-2-yl | | 4,740 | | a. Expressed in nM (single determination or mean ± S.E.M. for 3 or more determinations) vs. [$^3$H]PIA (1 nM) at rat A$_1$-receptors and vs. [$^3$H]CGS21680 (5 nM) at rat striatal A$_2$-receptors.
b. Shamim et al., J. Med. Chem., 32, 1231–1237 (1989)
c. Percent displacement of specific binding at the concentration indicated in parentheses.

The greatest effect of elongating N—Me to N—Pr groups at the N-1 and N-3 positions was a substantial increase in A$_1$-affinity, thus diminishing A$_2$-selectivity. A 1,3-diethyl-7- methylxanthine, 45b, was nearly as $A_2$-selective (34-fold) as the 1,3-dimethyl analogue, 44b, which was 70-fold selective. The corresponding diallyl analogue, 46 (reported previously by Shimada et al., 1992, supra) to be >6700 $A_2$-selective), was only 13-fold selective in rat brain in this study.

The N-7 position was either H— or substituted with groups as large as 2-phenylethyl (compound 44f). Only small, hydrophobic groups (including ethyl and propargyl) at this position were tolerated in binding to either receptor. The 7-methyl analogues were found to exhibit the greatest degree of $A_2$-selectivity.

Figure 4:
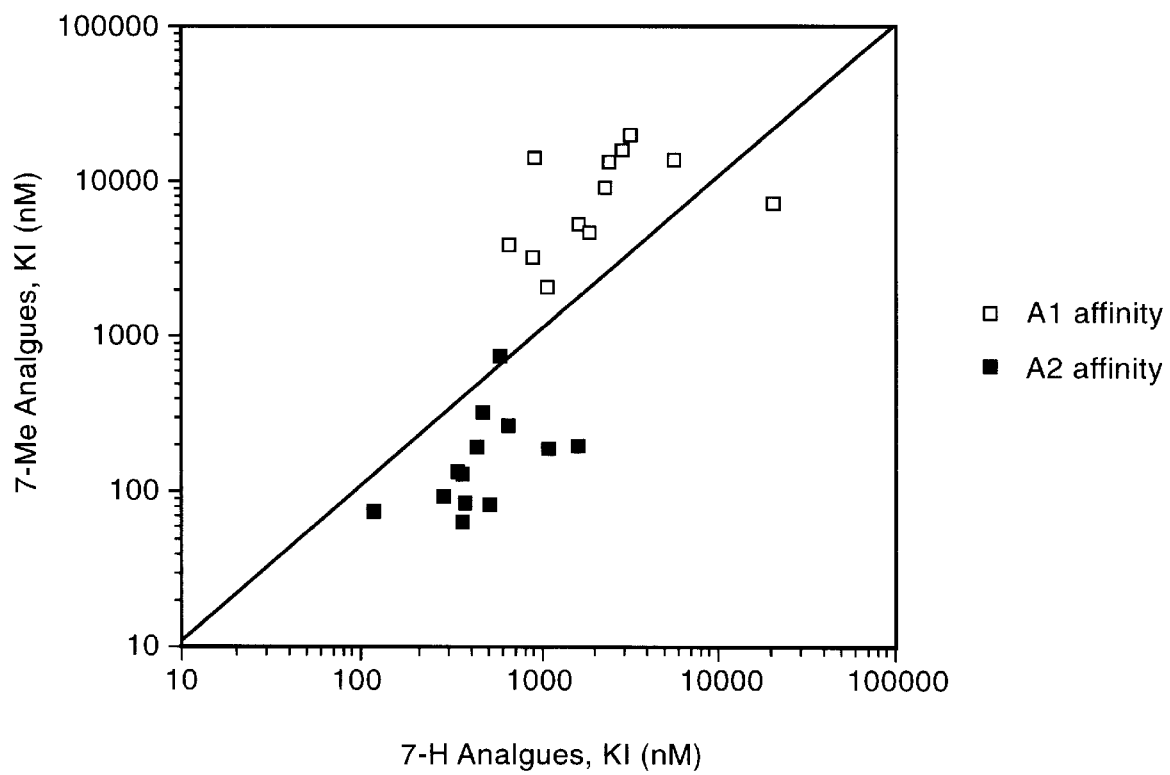
FIG. 4 is a graph of the $K_i$ of 7-methyl analogues (nM) versus the $K_i$ of 7-H analogues (nM), which shows the correlation of affinity at adenosine receptors for 7-H versus 7-methyl analogues of 1,3-dimethyl-8-styryl-xanthine derivatives.
Figure 5:
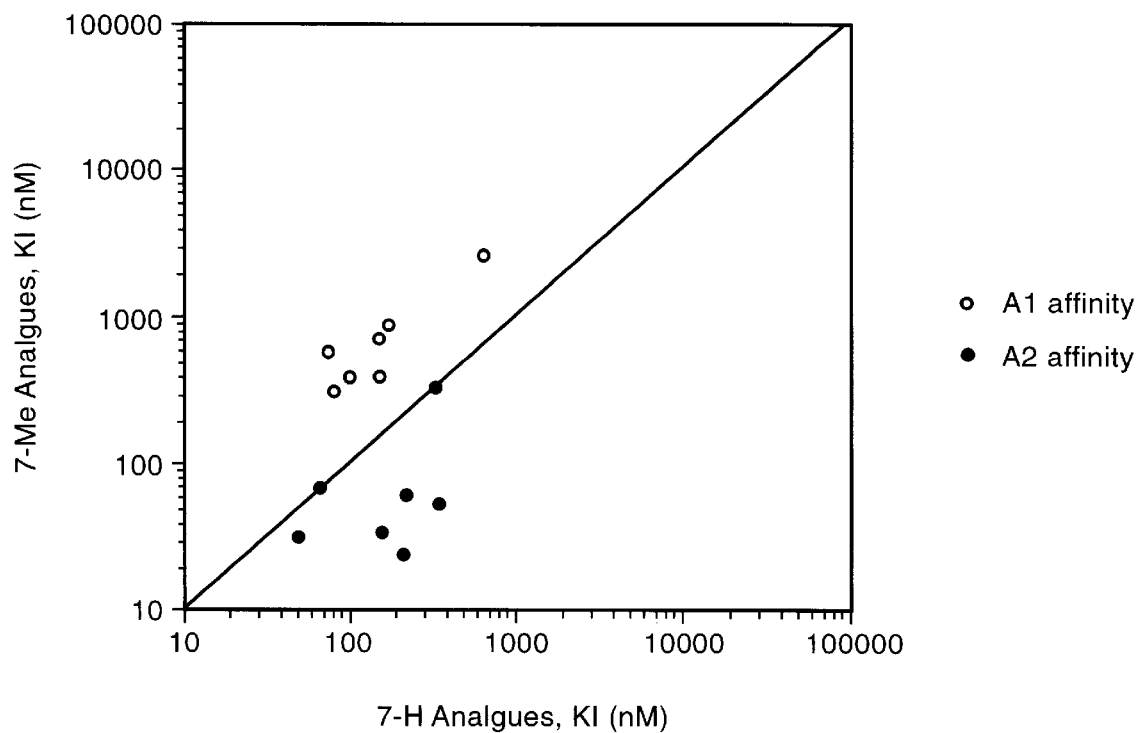
FIG. 5 is a graph of the $K_i$ of 7-methyl analogues (nM) versus the $K_i$ of 7-H analogues (nM), which shows the correlation of affinity at adenosine receptors for 7-H versus 7-methyl analogues of 1,3-dipropyl-8-styryl-xanthine derivatives.

FIGS. 4 and 5 are graphs of $K_i$ (nm) for 7-methyl analogues versus $K_i$ (nM) for 7-H analogues, which show correlations of affinity at adenosine receptors for the 7-H to 7-Me modification, which generally results in decreased $A_1$ affinity and increased $A_2$ affinity. The correlations of affinity for the 7-H to 7-methyl modification in 1,3-dimethyl-8-styryl-xanthine derivatives is shown in FIG. 4, whereas the correlations of affinity for the 7-H to 7-methyl modification in 1,3-dipropyl-8-styryl-xanthine derivatives is shown in FIG. 5. In both figures, inhibition constants in nM are given for $A_1$ (□, FIG. 4; ○, FIG. 5) and $A_2$ (■, FIG. 4; ●, FIG. 5) receptors. In general, among 8-styrylxanthine derivatives, the 1,3,7-trimethylxanthines were $A_2$-selective by factors between 10 and 500-fold, whereas the corresponding 1,3-dimethylxanthines were generally $A_2$-selective by factors of only 2 and 5-fold. The 7-hydroxyethyl and phenylethyl substituents were nearly inactive, in addition to having less favorable aqueous solubility. In the 1,3-dipropyl series (FIG. 5), each 7-H analogue was relatively non-selective. The selectivity of the 1,3-dipropyl-7-methyl-8-styryl xanthines (resulting from decreased Al affinity upon methylation) was highly dependent on the styryl substitution.

The effects of substitution of the 8-styryl group could be compared within the 1,3-dimethyl series and within the 1,3,7-trimethyl series. The unsubstituted styryl analogue 15a (7-H) was non-selective, but was moderately selective (41-fold) following methylation (15b). Fluorine substitution in the α-position resulted in diminished potency at both $A_1$- (3-fold) and $A_2$-receptors (7-fold). Monomethoxy substitution of the phenyl ring (compounds 17, 19, and 29) resulted in selectivity of 18- to 63-fold in the 7-Me series, but did not result in significant $A_2$-selectivity in the 7-H series. Compound 19, the meta derivative, was the most potent and selective monomethoxy derivative, with a $K_i$ value of 85 nM at $A_2$-receptors. The analogue bearing a 3-hydroxystyryl group in the 7-H series, 18, was equipotent with the methoxy compound, 19b, at $A_2$-receptors and more potent at $A_1$-receptors.

The $A_2$-potency of 1,3,7-trimethyl-xanthines having a variety of styryl 3-position substituents varied in the order: acetylamino>chloro, amino>fluoro, methoxy>H>trifluoromethyl>nitro. Although the 3-chloro derivative (28, $K_i$ value of 54 nM) was slightly less potent than the 3-acetylamino derivative (23, $K_i$ value of 39 nM, 240-fold selective), it was more selective (520-fold). It was equipotent to the amino derivative, 22b, but considerably more selective. Very bulky substituents at the 3-position (urethanes 25 and 26) reduced potency at $A_2$-receptors roughly 20-fold, but moderate $A_2$-selectivity remained. A water-solubilizing 3-succinylamino group (24) resulted in decreased potency (134 nM) but high selectivity (250-fold).

For comparison to the methoxy group at the styryl 4-position, a highly electron donating group, e.g. dimethylamino, was incorporated and resulted in greatly diminished potency at both receptors. Only the 7-Me form, 30b, displayed $A_2$-selectivity.

Dimethoxy substitutions at various positions of the phenyl ring were compared, and substantial differences were observed. The order of both potency and selectivity was 3,5>3,4>2,3. In the 1,3,7-trimethyl series, 3,5-dimethoxy or 3,5-difluoro substituents (33b and 34b, respectively) resulted in >200-fold selectivity.

In the 1,3-dipropyl-7-methyl- series, A2-selectivity was generally merely 5- to 19-fold, with only one exception (53b). The 3-chlorostyryl analogue, 51b, analogous to the most selective agent in the 1,3,7-trimethyl series, was only 14-fold selective. 1,3-Dipropyl-7-methyl-8-(3,5-dimethoxystyryl)xanthine, 53b, proved to be a potent ($K_i$ vs. [$^3$H]CGS 21680 was 24 nM) and $A_2$-selective (110-fold) adenosine antagonist, i.e., 5-fold more selective than the corresponding 3,4-dimethoxy analogue, 52b. Compound 52b was prepared by Shimada et al. (1992, supra, [KF17837]) and was reported to be 190-fold selective, versus 19-fold in this study.

High selectivities were also observed among 1,3,7-dimethylxanthines that were trisubstituted on the phenyl ring. 1,3,7-trimethyl-8-(3,4,5-trimethoxy)-styryl-xanthine, 44b, was 70-fold $A_2$-selective in binding in the rat brain (versus >5600-fold reported by Shimada et al., 1992, supra). The corresponding 1,3-dimethyl analogue was only 10-fold $A_2$-selective. In general, the order of both potency and selectivity for trisubstituted phenyl substituents was 3,4,5>2, 3,4>2,4,5. Among 3,4,5-substituted analogues there was considerable substitution of the 4-methoxy group tolerated at $A_2$-receptors. The moderately selective 3,5-dimethoxy-4-hydroxy analogue, 35, was acylated (36) and alkylated (37, 38), resulting in enhanced $A_2$-selectivity and potency. The 4-acetoxy-3,5-dimethoxy analogue, 36, was 93-fold $A_2$-selective. Functional groups that also tended to increase water solubility, such as alkyl amines (38 and 40) were included. These amino derivatives may serve as functionalized congeners (Jacobson, J. Med. Chem., 32, 1043–1051 (1989a)) since it appears that long chain extension is possible without disrupting receptor binding. Moderately potent and selective acylated derivatives were prepared from the amine functionalized. Butyl versus trans-butenyl amine were compared to examine the effect of altering conformational flexibility at this distal site. No major differences in potency or selectivity between butyl and butenyl analogues were found.

In an attempt to account for the discrepancy in $K_i$ values between the present study and Shimada et al. (1992, supra), the effects of varying concentrations of DMSO in the assay medium were examined. DMSO was needed because of the limited aqueous solubility (in the range of $10^{-5}$M) of most of the 8-styrylxanthines tested. To avoid precipitation associated with serial aqueous dilutions, the only point at which DMSO was added to aqueous medium was immediately prior to the incubation.

Figure 6A:
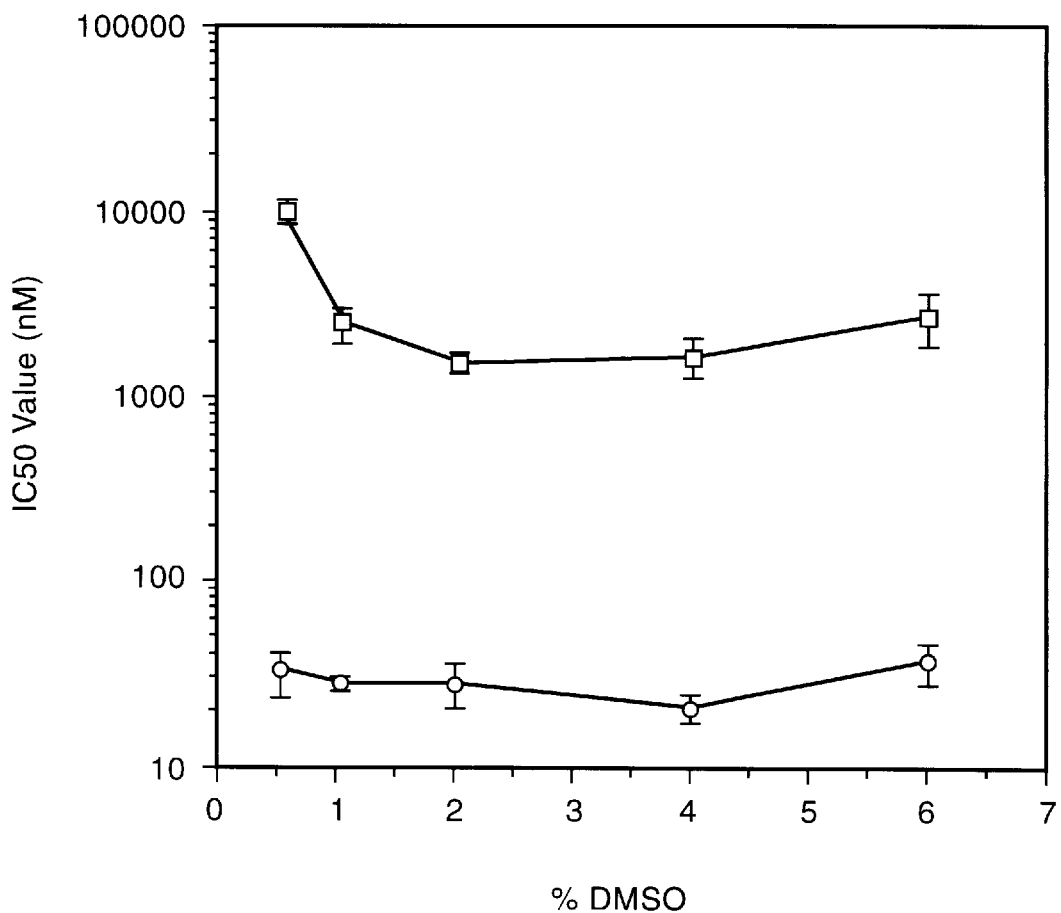
FIG. 6A is a graph of $IC_{50}$ versus % dimethylsulfoxide (DMSO), which shows the dependence of observed $IC_{50}$ on the concentration of DMSO in competitive radioligand binding of 1,3-dipropyl-8-(3,5-dimethoxy-styryl)-xanthine.
Figure 6B:
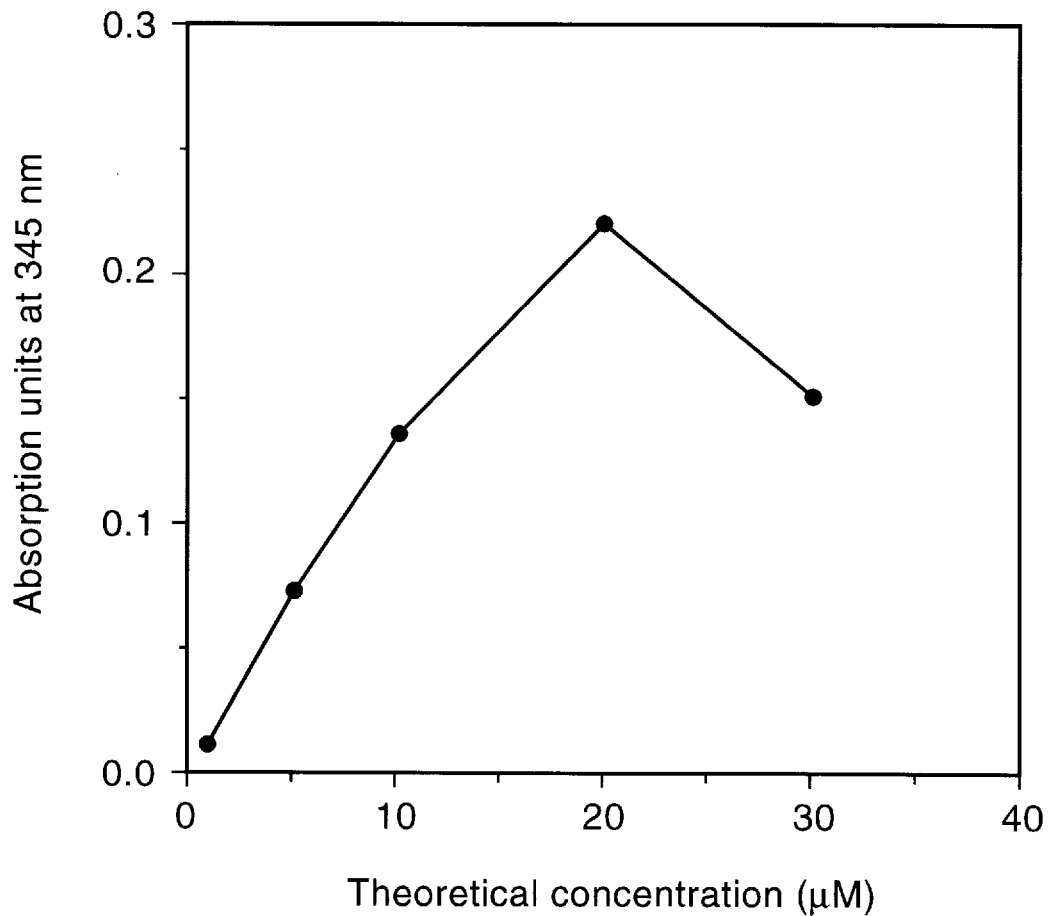
FIG. 6B is a graph of absorption units at 345 nm versus theoretical concentration, which shows the UV absorption of water solutions following the addition of 1,3-dipropyl-8-(3,5-dimethoxy-styryl)-xanthine dissolved in DMSO.

The effects of varying concentrations of DMSO (ranging from 0.5–6%) on the apparent affinity of compound 53b (FIG. 6A) was measured. FIG. 6A is a graph of $IC_{50}$ (nM, mean±S.E.M. for 3 or more determinations) versus % DMSO for [$^3$H]PIA (1 nM) at rat A receptors (squares) and [$^3$H]CGS21680 (5 nM) at rat striatal $A_2$ receptors (circles), which shows the dependence of observed $IC_{50}$ values on DMSO concentration in competitive radioligand binding assays. The apparent affinity of compound 53b at $A_2$ receptors was constant within the range of 0.5% to 6% DMSO. In addition, the total specific binding of [$^3$H]CGS 21680 to striatal membranes was maintained, even at 6% DMSO. However, $A_1$ affinity appeared to be somewhat dependent on DMSO concentration (at 0.5 and 1% DMSO), and at 6% DMSO the total specific binding of [$^3$H]PIA (data not shown) diminished to roughly 30% of its value at 1%. At the lowest concentration (0.5% DMSO), higher concentrations of the drug were required to displace [$^3$H]PIA. This effect of increase in the apparent $K_i$ value at ≦1% DMSO most likely relates to the xanthine precipitating from the solution, since the UV absorption does not increase in a linear fashion with the amount of xanthine added to a fixed aqueous volume as shown in FIG. 5B, which is a graph of absorption units at 345 nm versus theoretical concentration, which shows the UV absorption of water solutions following addition of 1,3-dipropyl-8-(3,5-dimethoxystyryl)-xanthine dissolved in 0.5% DMSO (theoretical final concentration assuming complete dissolution given on abscissa), with a peak absorption occurring at 345 nm with a molar extinction coefficient ($\epsilon$) of 13,200. The UV absorption decreases beyond 20 μM, suggesting supersaturation.

Related, non-styryl xanthines (Table IV) were tested in adenosine receptor binding for comparison to the 8-styryl derivatives. Cyclohexylcaffeine, 2, which was found to be $A_2$ selective in effects on adenylate cyclase (Shamim et al., *J. Med. Chem.*, 32, 1231–1237 (1989)), was non-selective in binding. The saturated aniline derivative 57 was ~300 fold-less potent at $A_2$ receptors than the corresponding styryl derivative, 22b. Ring-constrained styryl analogues, 58, containing a 8-(2-benzofuran) group were synthesized. Both the 7-H and 7-Me analogues were only weak antagonists of binding at adenosine receptors (Table IV).

The selectivity factors in the present study were generally much less than in Shimada et al. (1992, supra). The principal reason may be that $A_1$-affinity in this study was measured in the same species as $A_2$-affinity (rat), whereas Shimada et al. measured $A_1$ affinity in guinea pig brain and $A_2$ affinity in rat brain. The species dependence of affinity of alkylxanthines at both $A_1$ and $A_{2a}$ receptors is well documented (Ukena et al., *FEBS Letters*, 209, 122–128 (1986a); Stone et al., *Drug Dev. Res.*, 15, 31–46 (1988)). Invariably, $A_1$ affinity is higher in the rat than in the guinea-pig, but the affinity ratios have been found to vary from only 2-fold for theophylline to as much as 20-fold for 8-phenyltheophylline (Ukena et al., 1986a, supra). Indeed, the $A_1$ affinities in rat reported here differ even more: up to 33-fold (e.g., compound 47: $A_1$ affinity in rat is 55 nM versus 1800 nM in guinea-pig (Shimada et al., 1992, supra); Erickson et al.,*J. Med. Chem.*, 34, 1431–1435 (1991) have determined a $K_i$ value at rat $A_1$ receptors of 22 nM). Thus, comparing guinea-pig $A_1$ values to rat $A_2$ affinities results in artificially high selectivity ratios. Therefore, the affinities reported by Shimada et al. are inaccurate, given that same-species comparisons were not performed. In addition, some unexplained and substantial differences (e.g. compound 50a) were observed between $K_i$-values versus [$^3$H]CGS 21680 in this study and versus [$^3$H]NECA in Shimada et al. (1992, supra) (both having been measured in rat striatal membranes).

Another potential reason for discrepancies with previous results in binding assays was the amount of DMSO present. Shimada et al. (1992, supra) utilized approximately 1% DMSO in the assay medium, whereas 2% was used in this study. At 0.5% DMSO a 1,3-dipropyl-7-methylxanthine derivative, 53b, did not remain dissolved in aqueous solution at concentrations greater than 10 μM (FIG. 5A). This would affect, in particular, $A_1$ displacement curves for many compounds in this study, for which data points beyond xanthine concentrations of 10 μM are required. Thus, the addition of insufficient DMSO to the medium (or serial aqueous dilutions) might tend to overestimate the selectivity of the $A_2$-selective xanthines, but would not be expected to alter the apparent affinity at $A_2$ receptors (FIG. 5A).

In summary, the position of styryl ring substitution (meta favored) is a determinant of potency and selectivity (compare 17b, 19b, and 29b). Increasing the size of small alkyl groups at the 1- and 3-xanthine position (e.g. 45b versus 44b) increases potency at both receptors and decreases $A_2$ selectivity. $A_2$-selectivity and moderate affinity are maintained with long chain extension from the para-position of the styryl ring (e.g. 41). It would seem that this position of the 8-styryl group, when bound to the receptor, is located in a relatively insensitive region. $A_2$-selectivities of thousands of fold reported previously (Shimada et al., 1992, supra) were not observed in this study, although the selectivities of up to 520-fold (compound 28a), promise to be useful in physiological studies. $A_2$-antagonists of particular interest are: compounds 23, 24, 27b, 28a, 33b, and 34b ($A_2$-selectivity of 200-fold or greater); compounds 23, 28a, 49, 50b, 52b, 53b, and 54b ($A_2$-affinity 50 nM or less); compounds 22b, 38, and 40 (amine functionalized). Compound 24 also has enhanced water solubility; the maximal solubility in a 0.1M potassium phosphate solution at pH 7.4 was 19 mM.

EXAMPLE 4

This example describes the synthesis of 8-(3-isothiocyanatostyryl)-caffeine, which is a selective irreversible inhibitor of binding to $A_{2a}$-adenosine receptors.

2-Chloroadenosine was obtained from Research Biochemicals, Inc. (Natick, Mass.). [$^3$H]N$^6$-phenylisopropyladenosine, and [$^3$H]CGS 21680 were obtained from Dupont NEN (Boston, Mass.).

1,3,7-trimethyl-8-(3-aminostyryl)-xanthine (50 mg, 0.16 mmol) was dissolved in 2 ml chloroform, and saturated sodium bicarbonate solution (1 ml) was added. After cooling the mixture in an ice bath, thiophosgene (0.1 ml, 1.3 mmol) was added at once with vigorous stirring. After 5 min, the reaction was complete, and additional solvent was added to break the emulsion. The phases were separated, and the organic phase was washed several times with water and dried (MgSO$_4$). The solvent was evaporated, and the solid yellow residue was recrystallized from chloroform/acetonitrile to provide 32 mg (57% yield) of the homogeneous product, 8-(3-isothiocyanatostyryl)caffeine (ISC) or 1,3,7-trimethyl-8-(3-isothiocyanatostyryl)xanthine hemihydrate (TLC system chloroform: methanol: acetic acid, 95:4:1, $R_f$=0.41). Mp 268°–271° C. $^1$H NMR CDCl$_3$ d 3.43 (s, 3H N—CH$_3$); 3.63 (s, 3H N—CH$_3$); 4.07 (s, 3H N7-CH$_3$); 6.93 (d, 1H J=16 Hz, olefin); 7.21 (d, 1H J=8 Hz); 7.39 (t, 1H J=8 Hz, C5 arom); 7.44 (s, 1H, C2 arom); 7.47 (d, 1H J=8 Hz); 7.75 (d, 1H J=16 Hz, olefin). MS (EI) M$^+$ 353. IR (NaBr) 2124 cm$^{-1}$. Elemental analysis (C$_{17}$H$_{15}$N$_5$O$_2$S.0.5 H$_2$O): calculated, 56.34% C, 4.45% H, 19.33% N; found 56.43% C, 4.16% H, 19.07% N.

EXAMPLE 5

This example describes the radioligand binding assay that was used to assess the irreversible, inhibitory activity of ISC at $A_2$-adenosine receptors.

Striatal tissue was isolated by dissection of rabbit, bovine, and rat brain, obtained frozen from Pel-Freeze Biologicals Co. (Rogers, Ark.), and guinea pig brain, obtained frozen from Keystone Biologicals (Cleveland, Okla.). Membranes were homogenized in 20 volumes of ice cold 50 mM Tris HCl (pH 7.4) using a Polytron (Kinematica, GmbH, Lucerne, Switzerland) at a setting of 6 for 10 sec. For each species except rat, the homogenization was carried out in the presence of protease inhibitors (5 mM EDTA, 0.1 mM phenylmethanesulfonyl fluoride, 0.01 mg/ml soybean trypsin inhibitor, 5 µg/ml leupeptin, 1 µg/ml pepstatin A). The membrane suspension was then centrifuged at 37,000×g for 10 min at 4° C. The pellet was resuspended (20 mg tissue/ml) in the above buffer solution, preincubated at 30° C. for 30 min with 3 IU/ml of adenosine deaminase, and the membranes were again homogenized and centrifuged. Finally the pellet was suspended in buffer (100 mg wet weight per ml) and stored frozen for no longer than two weeks at −70° C. Protein was determined using the BCA protein assay reagents (Pierce Chemical Co., Rockford, Ill.).

Striatal membranes were treated with inhibitor as follows. Membranes were incubated with ISC in pH 7.4 Tris buffer containing adenosine deaminase for 1 h at 25° C., and subjected to three washing cycles, which consisted of centrifugation at 37,000×g and resuspension of the pellet in Tris buffer, prior to radioligand binding. For kinetic experiments with the affinity label, aliquots were removed periodically and quenched with a large volume of buffer solution (30×) prior to radioligand binding. For protection experiments, membranes were preincubated with theophylline at 25° C. for 20 min, and then ISC was added immediately for an additional incubation at 25° C. for 30 min. At the end of this sequence, the membranes were washed by repeated centrifugation and resuspension and subjected to [$^3$H]CGS 21680 binding.

Washing cycles for inhibition experiments required resuspending the membrane pellet by gentle vortex mixing. At the final step, prior to radioligand binding, the membranes were homogenized manually using a glass tissue grinder.

In competition studies, to avoid precipitation of the xanthine in the 100 µM concentration range, the tubes in that range containing all components were warmed to ~50° C., prior to the incubation carried out for 90 min at 37° C.

For saturation and competition studies, $B_{max}$, $K_d$, and $IC_{50}$ values were determined using the Ligand and Inplot (Graphpad, San Diego, Calif.) computer programs. $IC_{50}$ values were converted to apparent $K_i$ values using $K_D$ values in rat striatum of 1.0 and 15 nM for [$^3$H]PIA and [$^3$H]CGS 21680 binding, respectively, and the Cheng-Prusoff equation (Cheng and Prusoff, 1973, supra).

Competition by ISC of binding of [$^3$H]CGS 21680 (an $A_{2a}$-selective agonist) and [$^3$H]R-PIA (an $A_1$-selective agonist) in striatal membranes from four species was measured (Table V) under "reversible" conditions. Major species differences have been noted previously for xanthines binding at $A_{2a}$-adenosine receptors (Stone et al., 1988, supra). In rat striatum, the $IC_{50}$ at $A_{2a}$-receptors was found to be 146 nM (corresponding to an apparent $K_i$ value of 111 nM, assuming reversibility). At $A_1$-receptors the $IC_{50}$ was found to be 43 µM (corresponding to a $K_i$ value of 20 µM). Thus, the selectivity ratio of ISC for $A_{2a}$- versus $A_1$-receptors in the rat based on $IC_{50}$ values was 290-fold (180-fold, based on $K_i$ values). The selectivity ratio in guinea pig striatum was nearly identical. In other species, $A_{2a}$-selectivity was maintained (bovine, 120-fold, and rabbit, 180-fold), although the affinity was diminished. At rabbit $A_{2a}$ receptors, the apparent $K_i$ value of ISC was 290 nM based on the reported $K_d$ value of 28.6 nM for binding of [$^3$H]CGS 21680 (Jacobson et al., Mol. Pharmacol., 42, 123–133 (1992)). The Hill coefficients for displacement of binding of [$^3$H]CGS 21680 in the four species were approximately equal to 1. The $A_2$-selectivity of ISC was consistent with the previously determined $A_2$-selectivity of the amino precursor and the 3-chloro derivative (30-fold and 520-fold selectivity, respectively, based on $K_i$ values).

TABLE V

Potencies of ISC in inhibiting radioligand binding at central $A_1$ and $A_{2a}$, receptors in four mammalian species.[a]

| Species | $IC_{50}(A_1)$[a] | $IC_{50}(A_2)$[a] | $A_1/A_2$ ratio |
|---|---|---|---|
| Rat | 42,600 ± 3600[b] | 146 ± 2.6[c] | 291 |
| Guinea pig | 51,400 ± 17,700 | 160 ± 1.6 | 320 |
| Bovine | 63,400 ± 5,900 | 516 ± 64 | 122 |
| Rabbit | 75,600 ± 12 | 413 ± 135[d] | 183 | a. Express in nM (single determination or mean ± S.D. for 3 or more determinations vs. [$^3$H]PIA (1 nM) at striatal $A_1$-receptors and vs [$^3$H]CGS 21680 (5 nM) at striatal $A_{2a}$-receptors. Non-specific binding was determined in the presence of 10 µM 2-chloroadenosine.
b. Corresponds to $K_i$ value of 20,300 ± 1700 nM.
c. Corresponds to $K_i$ value of 111 ± 0.5 nM and a selectivity ratio of 182.
d. Corresponds to $K_i$ value of 347 ± 112 nM.

Figure 7A:
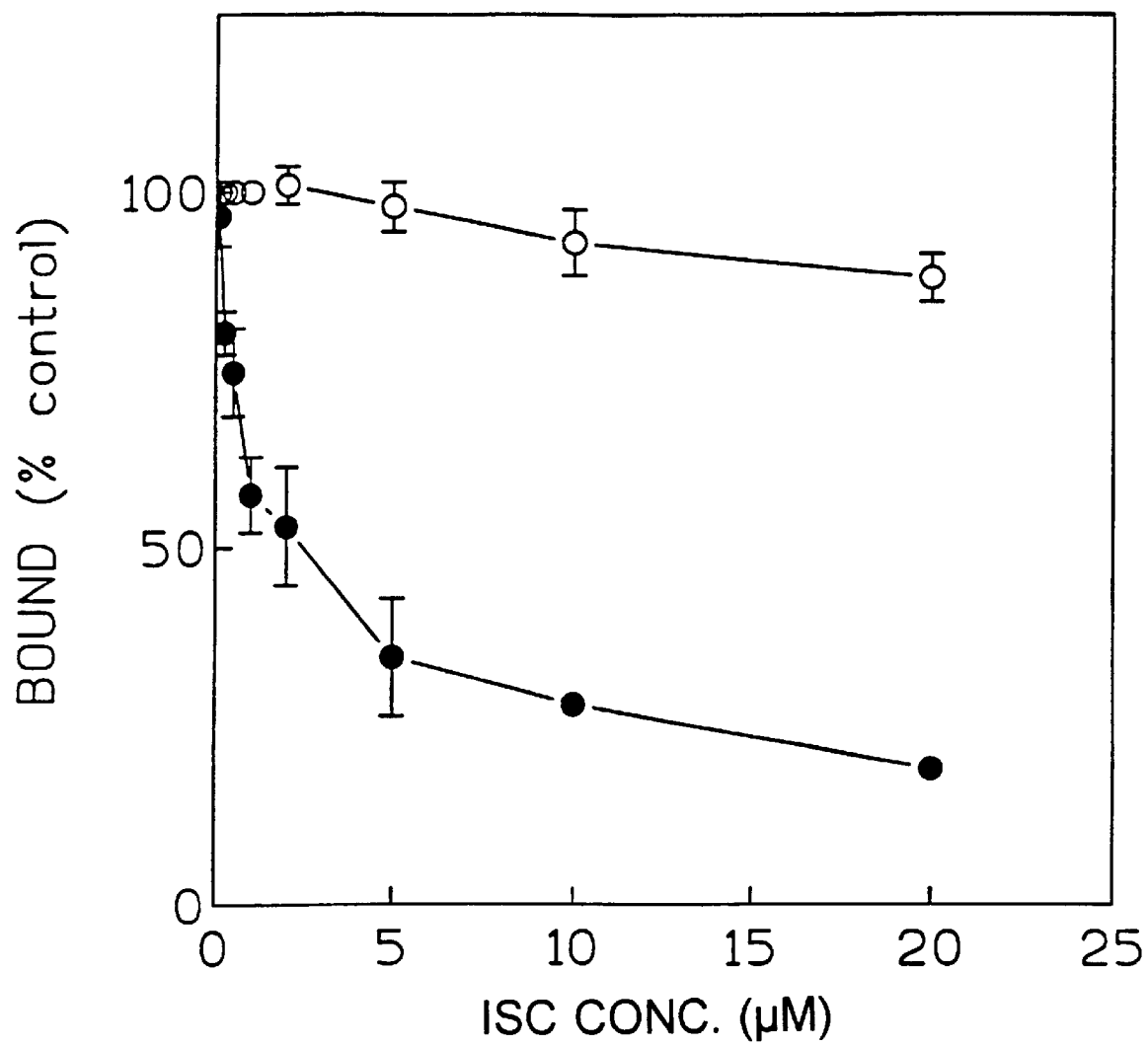
FIGS. 7A, B, C and D are graphs of bound radioligand (% control) versus 8-(3-isothiocyanatostyryl)-caffeine (ISC) concentration ($\mu$M), which show the dose-dependent inhibition by ISC of radioligand binding at $A_1$- and $A_{2a}$-adenosine receptors in rat, guinea pig, bovine, and rabbit striatal membranes, respectively.

ISC was examined for the ability to irreversibly inhibit $A_{2a}$-receptors. Preincubation of rat striatal membranes with ISC caused a dose-dependent, irreversible antagonism of the binding of 5 nM [$^3$H]CGS 21680 (an $A_{2a}$-selective agonist), with an $IC_{50}$ value of 2.7 µM (FIG. 7A). This $IC_{50}$ value was 18-times greater than the $IC_{50}$ value in competitive displacement of [$^3$H]CGS 21680 in the same tissue (Table V). Preincubation with 20 µM ISC resulted in the loss of approximately 80% of the specific binding of [$^3$H]CGS 21680. The irreversible nature of inhibition by the isothiocyanate derivative was demonstrated by the failure of repeated washing to regenerate the $A_{2a}$-receptor binding site. Nearly all of the binding of [$^3$H]N$^6$-phenylisopropyladenosine (PIA) to striatal $A_1$ receptors was recovered following washout by repeated cycles (4×) of centrifugation and resuspension of the membranes in fresh buffer. Thus, at $A_1$-adenosine receptors in rat striatal membranes, ISC at a high concentration of 20 µM was barely effective as an irreversible inhibitor. At this concentration only 12±2.9% of [$^3$H]PIA binding was lost compared to 81±1.6% of [$^3$H]CGS 21680 binding.

Exposure of the ISC-treated striatal membranes to the weak adenosine antagonist 3-isobutyl-1-methyl-xanthine (IBMX, 100 µM) overnight also did not regenerate any $A_{2a}$-receptor binding (data not shown). Treatment with IBMX was used to remove non-chemically bound ligand from the membranes in a previous study of chemically reactive xanthines as irreversible inhibitors of $A_1$-receptors (Jacobson et al., 1989, supra). Such treatment was found to be unnecessary, since no difference in binding was observed. Increasing the temperature of pre-incubation with ISC to 37° C. also did not affect significantly the fraction of binding irreversibly inhibited (data not shown).

Figure 7B:
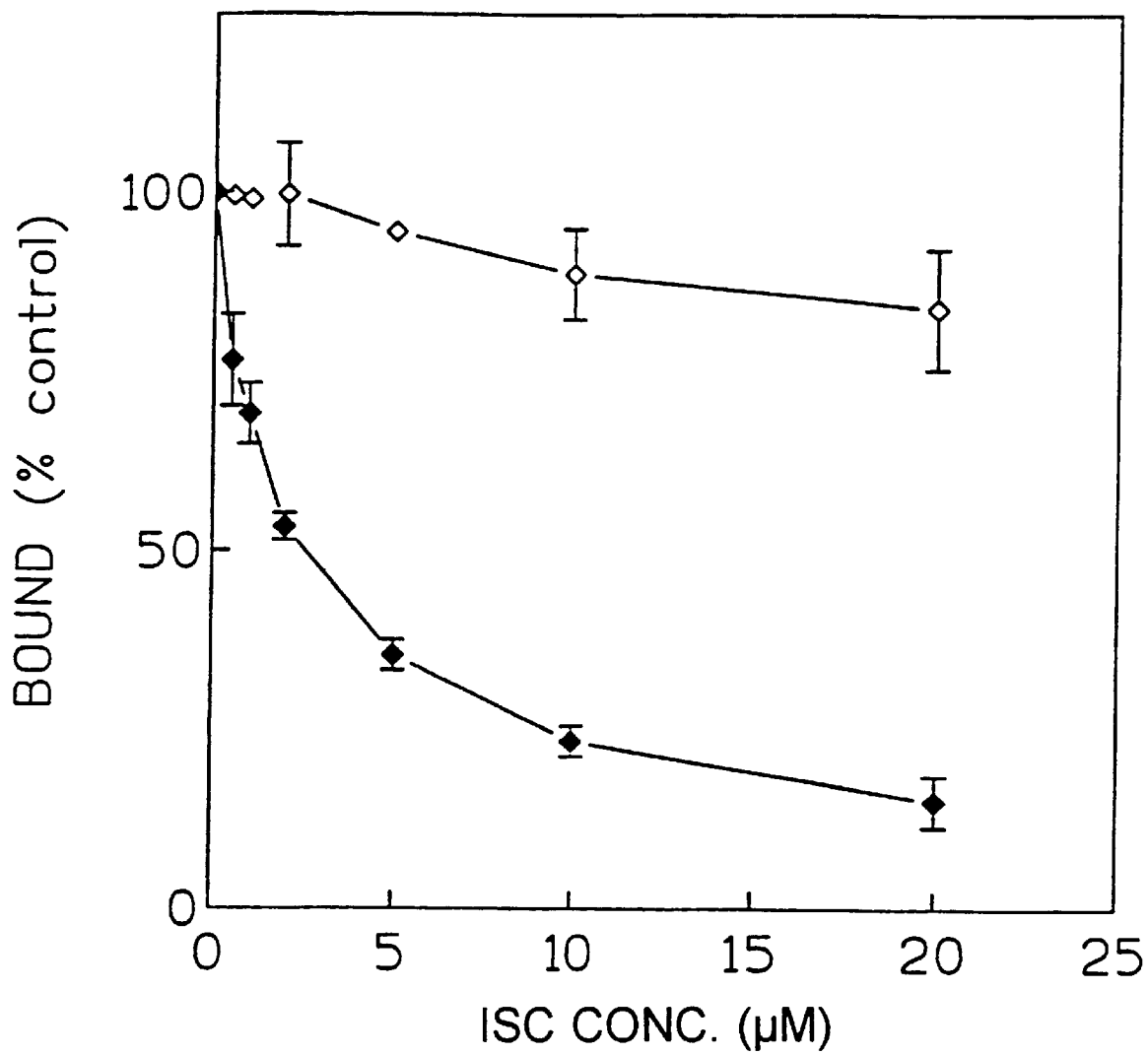
Figure 7C:
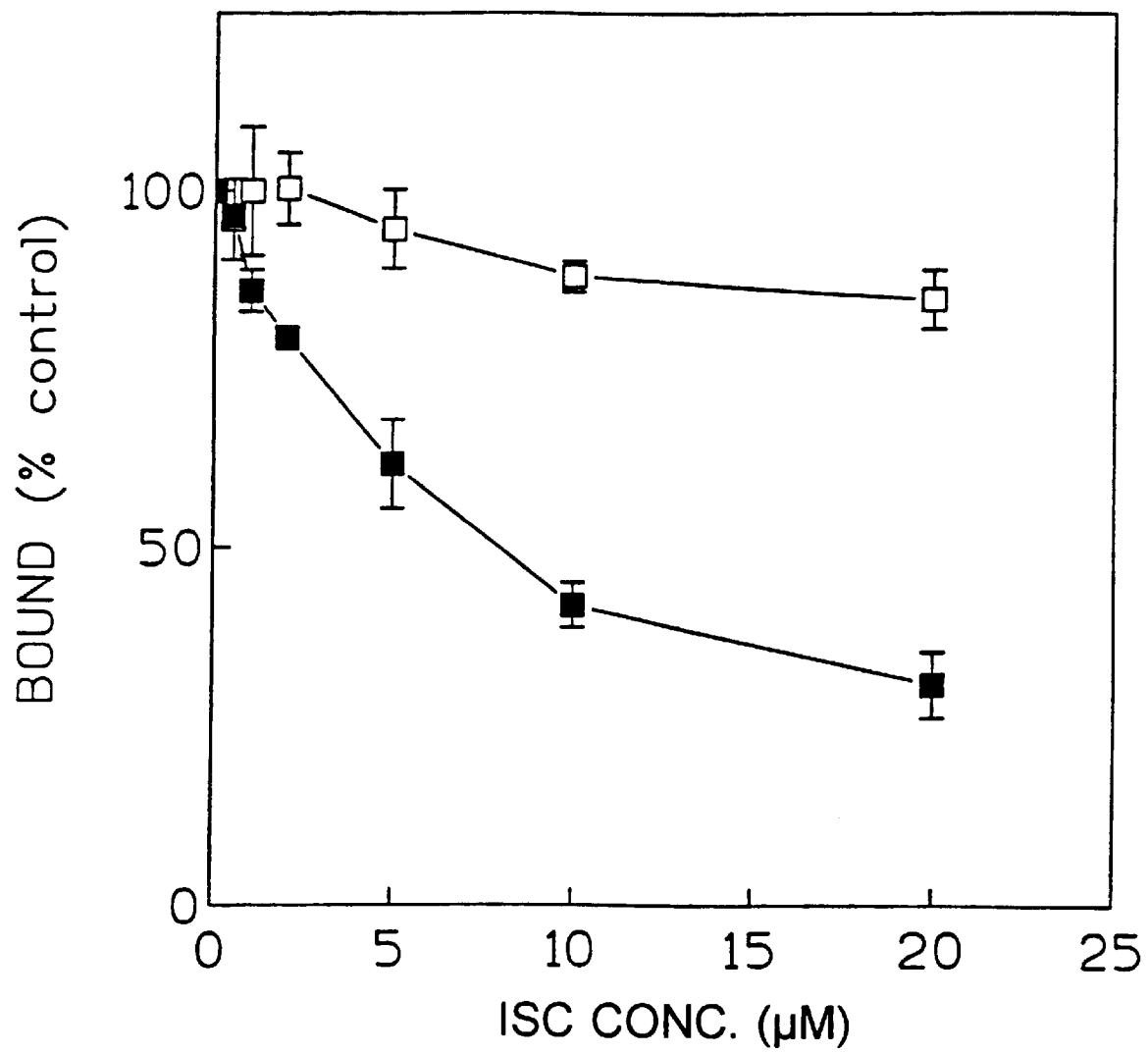
Figure 7D:
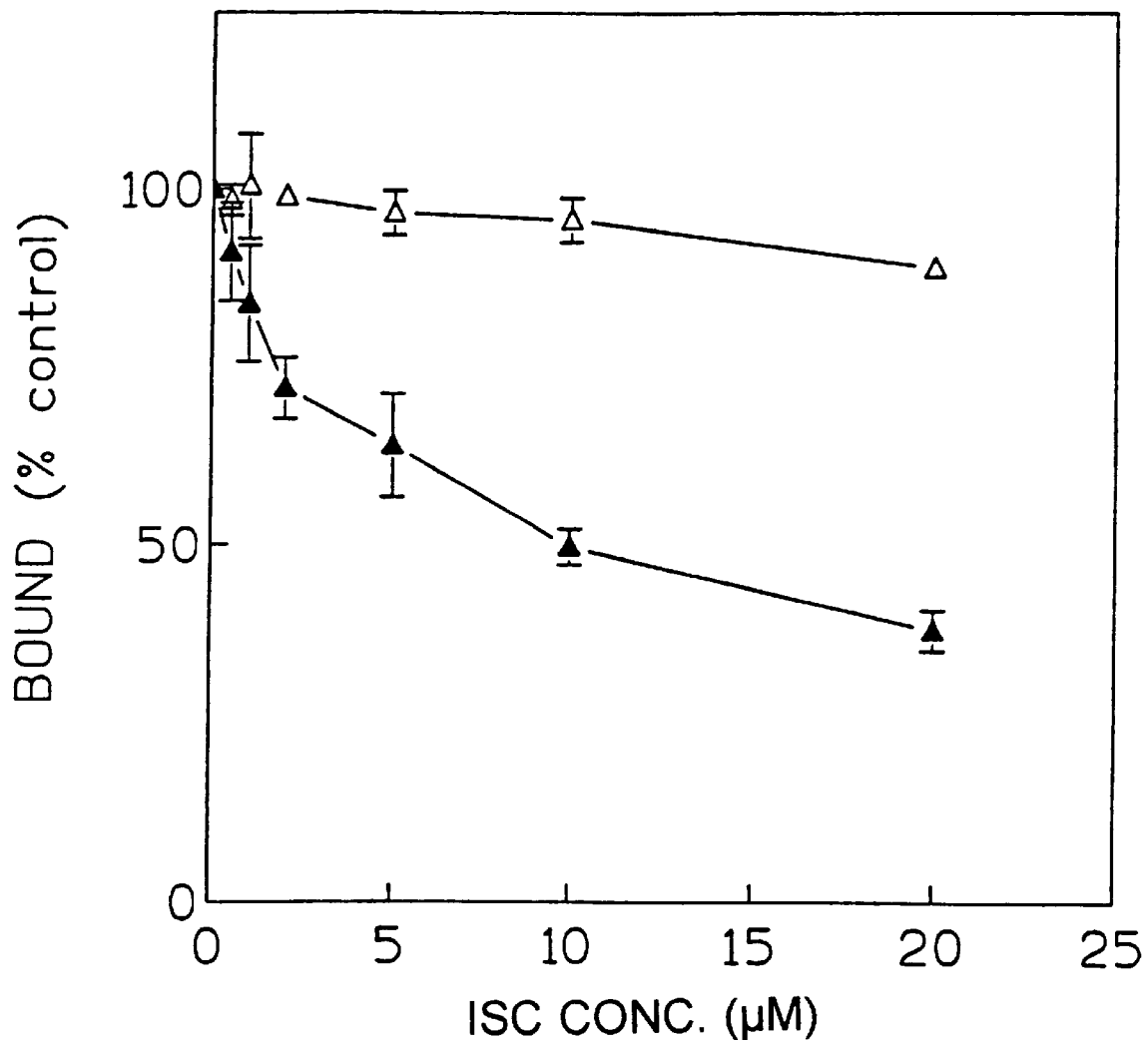

The irreversibility was examined in three other species (FIGS. 7B, C, and D). FIGS. 7A, B, C, and D show the dose-dependent inhibition by 8-(3-isothiocyanatostyryl)-caffeine (ISC) of radioligand binding at $A_1$- and $A_{2a}$-adenosine receptors in rat, guinea pig, bovine, and rabbit striatal membranes (n=4 or more), respectively. The preincubation with ISC or control was carried out for 1 h at 25° C. and the subsequent binding assay involved a 90 min incubation followed by rapid filtration. The radioligand binding step consisted of incubation (n=3) with 5 nM [$^3$H]CGS 21680 for $A_{2a}$-receptors or 1 nM [$^3$H]PIA for $A_1$-receptors. In the guinea pig striatum, the inhibition occurred at concentrations similar to those used with rat striatum ($EC_{50}$ value 2.8 $\mu M$). In rabbit and bovine striatum, ISC caused an irreversible inhibition of $A_{2a}$ receptors, but at considerably higher concentrations than in rat striatum. The $EC_{50}$ values for ISC irreversibly inhibiting bovine and rabbit $A_{2a}$ receptors were 8 and 10 $\mu M$, respectively.

The irreversibility is likely due to the presence of the chemically reactive isothiocyanate group, since the binding of the corresponding analogue in which the isothiocyanate was replaced by a chloro group was completely reversible (data not shown).

Figure 8:
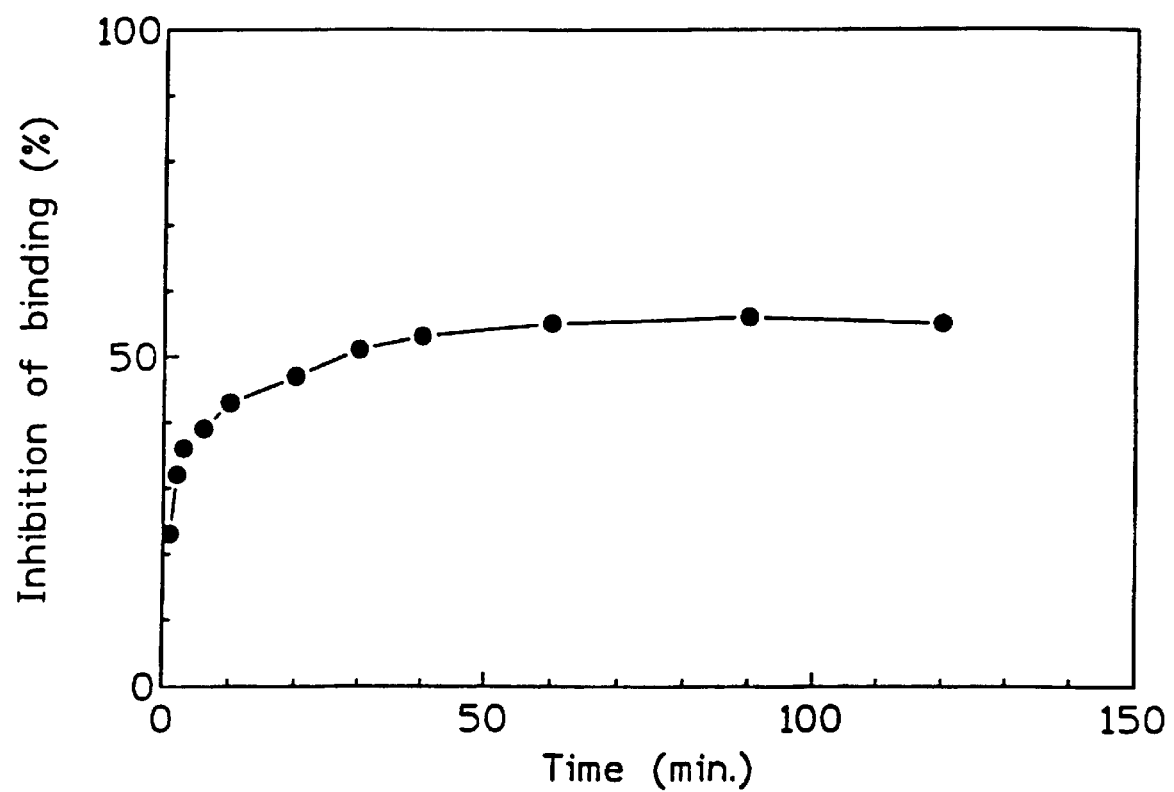
FIG. 8 is a graph of inhibition of binding (%) versus time (min), which shows the time course for inhibition of rabbit striatal $A_{2a}$-adenosine receptors at 25° C. by 2 $\mu$M ISC.

The time course for inactivation of rat $A_{2a}$ receptors by 2 $\mu M$ ISC is shown in FIG. 8. FIG. 8 is a graph of % inhibition of binding versus time (min), which shows the time course for inhibition of rabbit striatal $A_{2a}$-adenosine receptors at 25° C. by 2 $\mu M$ ISC. The membranes were washed by centrifugation (3×) prior to radioligand binding. [$^3$H]CGS 21680 was used at a concentration of 5 nM. The curve represents the data from three separate experiments. The time course for inactivation was rapid, although the degree of irreversible inhibition was not complete even after 2 h. Approximately 3 min was required for inhibition of 50% of its final value at 2 h (at 2 h approximately 55% of the specific [$^3$H]CGS 21680 binding relative to control membranes was lost). This concentration was only 14-fold greater than the $IC_{50}$ value for ISC in the "competitive" binding assay vs. [$^3$H]CGS 21680 (Table V). The fraction of receptors inactivated by this isothiocyanate derivative increased as the concentration of ISC was raised (FIG. 7).

Figure 9A:
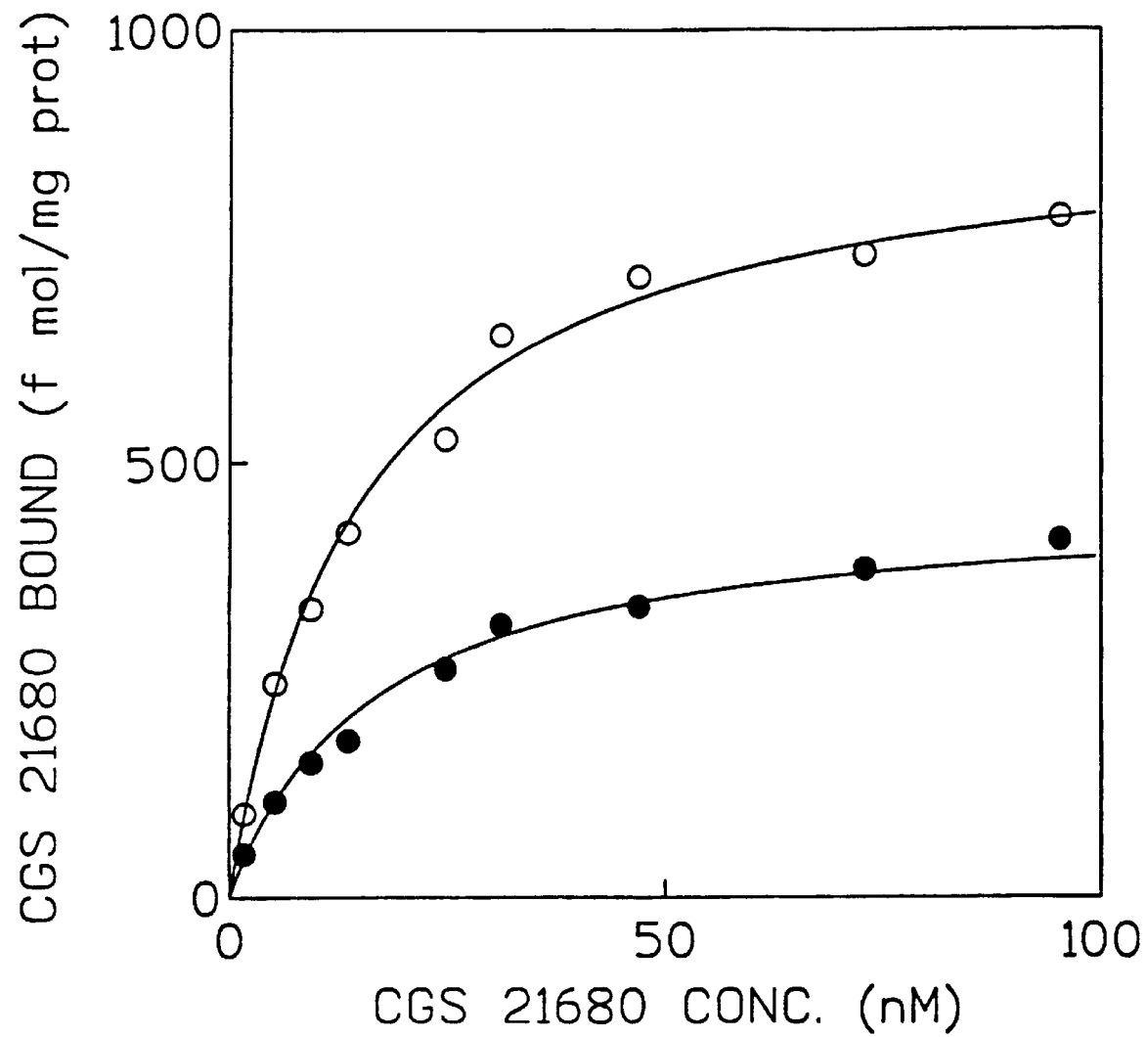
FIG. 9A is a graph of CGS 21680 bound (f mol/mg protein) versus CGS 21680 concentration (nM), which shows the saturation curve for the binding of [$^3$H]CGS 21680 to $A_{2a}$-adenosine receptors in rat striatal membranes.
Figure 9B:
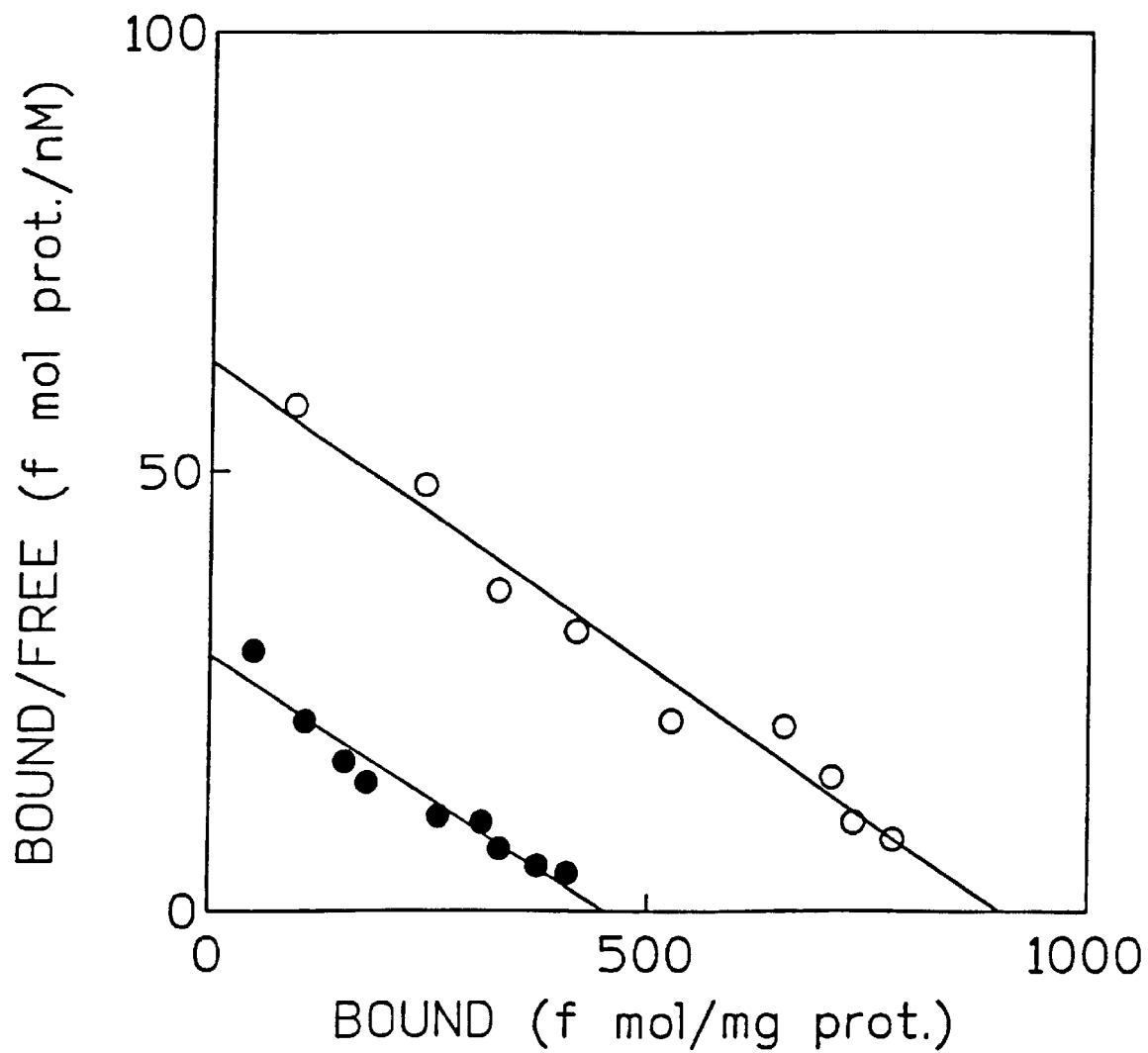
FIG. 9B is a Scatchard transformation for the binding of [$^3$H]CGS 21680 to $A_{2a}$-adenosine receptors in rat striatal membranes.

Saturation of binding of [$^3$H]CGS 21680 to rat striatal receptors following treatment with ISC and washing was measured and is shown in FIGS. 9A and B. FIG. 9A is a graph of CGS 21680 bound (f mol/mg protein) versus CGS 21680 concentration (nM), which represents the saturation curve for the binding of [$^3$H]CGS 21680 to $A_{2a}$ adenosine receptors in control (○) and experimental (●, i.e., following preincubation at 25° C. for 1 h with 2 $\mu M$ ISC) rat striatal membranes. FIG. 9B is a Scatchard transformation for the binding of [$^3$H]CGS 21680 to $A_{2a}$ adenosine receptors in rat striatal membranes. The volume of incubation for radioligand binding (approximately 150 $\mu g$ protein/tube) was 1 ml. Membranes were incubated with radioligand at 25° C. for 90 min. Specific binding in control and treated membranes is shown. Non-specific binding in control and treated membranes was nearly identical and amounted to 8–10% of total binding at 5 nM [$^3$H]CGS 21680. Following a preincubation resulting in partial inhibition, the $B_{max}$ value relative to control membranes at the remaining $A_{2a}$ sites was reduced without a significant effect on the $K_d$ value. Following treatment with 5 $\mu M$ ISC, the $K_d$ value for [$^3$H]CGS 21680 binding was 15.7 nM, and the $B_{max}$ value was 450 fmol/mg protein, compared to 14.3 nM and 900 fmol/mg protein for control. When the ISC-treated membranes were stored for one day at −20° C. prior to the saturation experiment, a reduction in $B_{max}$ (to 27 nM) was noted, while the affinity of CGS 21680 in the control membranes was unchanged.

Figure 10:
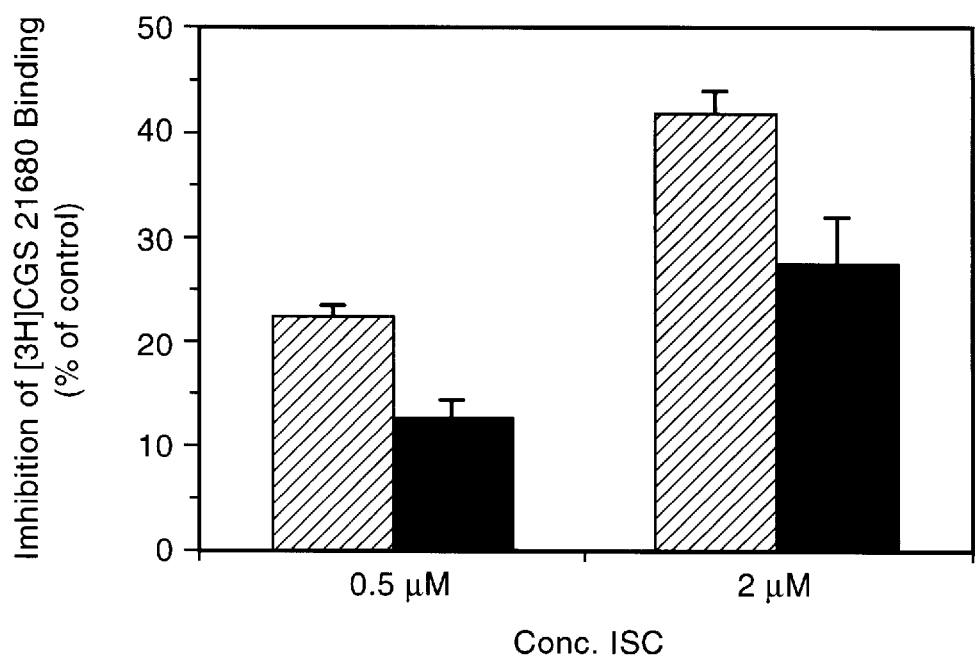
FIG. 10 is a bar graph of inhibition of [$^3$H]CGS 21680 binding (% of control) versus ISC concentration, which shows theophylline protection of rat striatal $A_{2a}$ receptors from ISC inhibition.

Inhibition of binding of [$^3$H]CGS 21680 at $A_{2a}$-receptors by ISC could be prevented by the adenosine receptor antagonist theophylline. The receptor was protected in the presence of 1 mM theophylline, with degrees of protection of 45% and 37% at 0.5 $\mu M$ and 2 $\mu M$ ISC, respectively (FIG. 10). FIG. 10 is a bar graph of inhibition of [$^3$H]CGS 21680 binding as a percentage of control versus 0.5 $\mu M$ and 2 $\mu M$ concentration of ISC, which shows theophylline protection of rat striatal $A_{2a}$ receptors from ISC inhibition. The percent irreversible inhibition relative to the level of specific binding of 5 nM [$^3$H]CGS 21680 in control membranes is shown (n=3). Shaded bars are for ISC alone, at the indicated concentration. Solid bars are for the combination of ISC and theophylline (1 mM).

ISC appears to be moderately selective for $A_{2a}$-versus $A_1$-receptors in four species. The chemical mechanism for the irreversibility is presumably acylation by the reactive isothiocyanate group of a nucleophilic group located on or in the vicinity of the antagonist binding site of the receptor protein. Following partial inactivation, the remaining rat $A_{2a}$-binding sites retained the same $K_d$ value for saturation by [$^3$H]CGS 21680. Thus, the inhibition is all-or-none, consistent with covalent anchoring of the ligand in its usual binding site.

EXAMPLE 6

This example shows that 1,3,7-trimethyl-8-(3-chlorostyryl) xanthine (CSC) is a highly selective $A_2$-adenosine receptor antagonist in vivo.

CSC and 2-[(2-aminoethylamino)-carbonylethylphenylethylamino]-5'-N-ethylcarboxamidoadenosine (APEC) were synthesized as described (Jacobson et al., *J. Med. Chem.*, in press; Jacobson et al., *J. Mol Recognit.*, 2, 170–178 (1989b)). All other xanthines and adenosine analogs are commercially available.

Biochemical activity of CSC was determined as follows. Antagonism of NECA-elicited stimulation of adenylate cyclase via an $A_{2a}$ receptor in rat pheochromocytoma (PC12) cell membranes or in human platelets was assayed as described (Ukena et al., *Life Sc.*, 38, 797–807 (1986b)). Antagonism of $N^6$-phenylisopropyladenosine-elicited inhibition of adenylate cyclase via an $A_1$ receptor in rat adipocyte membranes was assayed as described (Ukena et al., supra). $K_B$ values were calculated using the Schild equation from the ratio of $EC_{50}$ values for agonist in the presence and absence of antagonist.

Locomotor activity of CSC was determined as follows. Adult male mice of the NIH (Swiss) strain weighing 25–30 g were housed in groups of 10 animals per cage with a light-dark cycle of 12:12 h. The animals were given free access to standard pellet food and water and were acclimatized to laboratory conditions for 24 h prior to testing. Each animal was used only once in the activity monitor.

Locomotor activity of individual animals was studied in an open field using a Digiscan activity monitor (Omnitech Electronics Inc., Columbus, Ohio) equipped with an IBM-compatible computer. The computer-tabulated measurements represent multivariate locomotor analysis with specific measures, such as simultaneous measurements of ambulatory, rearing, stereotypical, and rotational behaviors. Data were collected in the morning, for three consecutive intervals of 10 minutes each, and analyzed separately and as a group. Statistical analysis was performed using the Student t test. The results are reported as mean ± standard error for each point. All drugs were dissolved in a 20:80 v/v mixture of Alkamuls EL-620 (Rhone-Poulenc, Cranbury, N.J.) and phosphate-buffered saline, except for CSC, which was dissolved initially in DMSO and diluted in at least 20 volumes of vehicle. Drugs were administered i.p. in a volume corresponding to 5 ml/kg body weight. Where applicable, the antagonist was injected 10 minutes before the agonist. $ED_{50}$ values were determined using regression analysis on the InPlot software (GraphPAD, San Diego, Calif.). The results are shown in Table VI.

TABLE VI

Receptor affinities and effects of various xanthines on adenosine agonist-elicited inhibition ($A_1$) or stimulation ($A_2$) of adenylate cyclase. Values are means or means ± S.E.M. (n = 3–4).

| Compound | Inhibition of Binding ($K_i$, μM) | | Adenylate Cyclase ($K_B$, μM) | | | Behavorial stimulation[d] |
|---|---|---|---|---|---|---|
| | Rat cortex[a] $A_1$ | Rat striatum[b] $A_{2a}$ | Rat adipocytes $A_1$ | Human platelets $A_{2a}$ | Rat PC12 cells $A_{2a}$ | |
| caffeine | 44 | 41 | 59[a] | 30 | 37 | +++(20) |
| DMPX | 45 | 16 | 94[a] | 4.0 | 9.6 | +++(10) |
| CPT | 0.024 | 1.4 | n.d. | 0.14 | n.d. | ++[c](10) |
| CPX | 0.0009 | 0.47 | 0.0006[b] | 0.14 | 0.25 | −(1) |
| CSC | 28 | 0.054 | 1.32 ± 0.26 | 0.26 ± 0.07 | 0.060 ± 0.014 | +(5) |

[a]vs. agonist ligand [$^3$H]$N^6$-phenylisopropyladenosine
[b]vs. agonist ligand [$^3$H]N-ethylcarboxamidoadenosine, except vs. agonist ligand [$^3$H]CGS 21680 for CSC
[c]stimulatory effect disappears within 20 min post-injection (Baumgold et al., Biochem. Pharmacol., 43, 889–894 (1992))
[d]degree of stimulation indicated by + through +++, with a typical dose (mg/g, i.p.) shown in parentheses
n.d. not determined In reversing adenosine agonist effects on adenylate cyclase (Table VI), CSC was 22-fold selective for $A_{2a}$ receptors in rat pheochromocytoma (PC12) cells versus $A_1$ receptors in rat adipocytes. CSC displayed a lower potency in adenylate cyclase effects at $A_{2a}$ receptors in human platelets ($K_B$ 260 nM) than at rat $A_{2a}$ receptors in PC12 cells ($K_B$ 60 nM). This probably reflects the species difference: large differences in potency of xanthines at adenosine receptors of different species have been noted previously (Stone et al., 1988, supra).

Figure 11A:
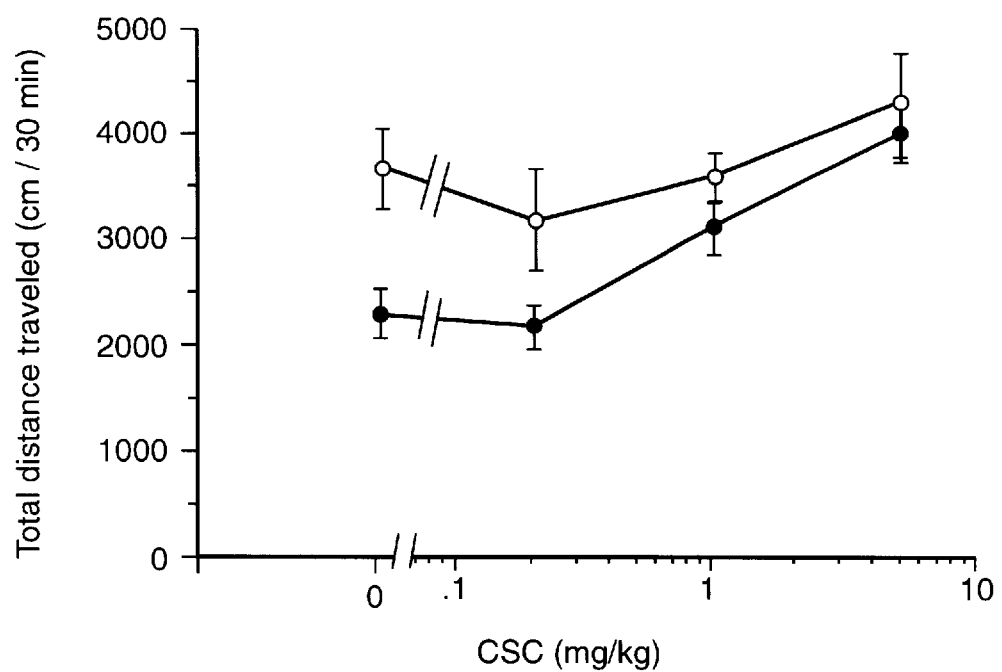
FIG. 11A is a graph of total distance traveled (cm/30 min) versus concentration of 1,3,7-trimethyl-8-(3-chlorostyryl)-xanthine (CSC, mg/kg), which shows the locomotor activity in male NIH Swiss mice by CSC.

The locomotor effects in mice of CSC alone or in combination with the potent and $A_{2a}$-selective agonist APEC (Nikodijevic et al., 1991, supra) were examined. CSC administered i.p. at a maximum soluble dose of 1 mg/kg was found to nearly completely reverse the locomotor depression elicited by APEC at its previously determined (Nikodijevic et al., supra) $ED_{50}$ of 16 μg/kg i.p. as shown in FIG. 11A, which is graph of total distance traveled (cm/30 min) versus CSC (mg/kg), which shows the locomotor activity in male NIH Swiss mice (6 weeks) by the $A_2$-selective adenosine antagonist CSC alone (○) or in the presence of the $A_2$-selective agonist APEC at 16 μg/kg (●). A dose of CSC of 5 mg/kg (injected as a suspension, since the solubility was exceeded at 1 mg/ml of injection vehicle) was found to cause significant locomotor stimulation by 22% over vehicle control value. The total distance traveled in CSC animals was 4223±496 cm/30 min (n=13) versus 3449±198 cm/30 min (n=8) in controls. This stimulation was most pronounced (56% increase versus control) in the last 10 minutes of the 30 min monitoring period. Since CSC was not very efficacious in stimulating locomotor activity at the highest tested dose, the $ED_{50}$ for CSC alone was not determined. The concurrent administration of a 16 μg/kg of dose of APEC with 5 mg/kg CSC had no effect on the locomotor activity. The drug combination resulted in a total distance traveled of 3949±284 cm/30 min (n=14). This level of locomotor activity represents a 73% increase versus APEC alone with 2277±229 cm/30 min (n=13).

CSC (5 mg/kg) had no effect on locomotor depression elicited by the potent A1 agonist CHA at its determined $ED_{50}$ value of 100 μg/kg i.p. Coadministration of both drugs resulted in a total distance traveled of 2029±250 cm/30 min (n=8) versus 2090±438 cm/30 min (n=9) for the CHA control.

Figure 11B:
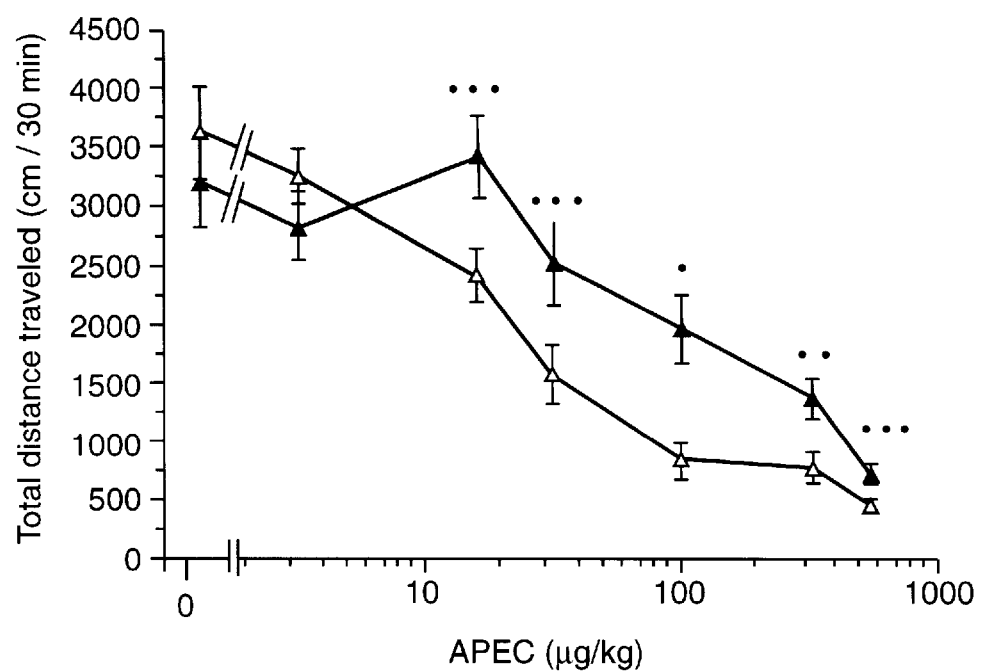
FIG. 11B is a graph of total distance traveled (cm/30 min) versus concentration of 2-[(2-aminoethylamino)-carbonylethylphenylethylamino]-5'-N-ethylcarboxamidoadenosine (APEC, $\mu$g/kg), which shows the locomotor depression in male NIH Swiss mice by APEC.

Dose response curves for locomotor depression by APEC in the absence and presence of CSC are presented in FIG. 11B, which is a graph of total distance traveled (cm/30 min) versus APEC (μg/kg), which shows the locomotor depression in mice by APEC alone (Δ) or in the presence of CSC at 1.0 mg/kg (▲), where n=6–19. The following p values are as indicated: * less than 0.005,  less than 0.01, and * less than 0.025. The $ED_{50}$ for locomotor depression elicited by APEC was right shifted from 20 μg/kg i.p. to 190 μg/kg following administration of 1 mg/kg CSC.

Figure 12:
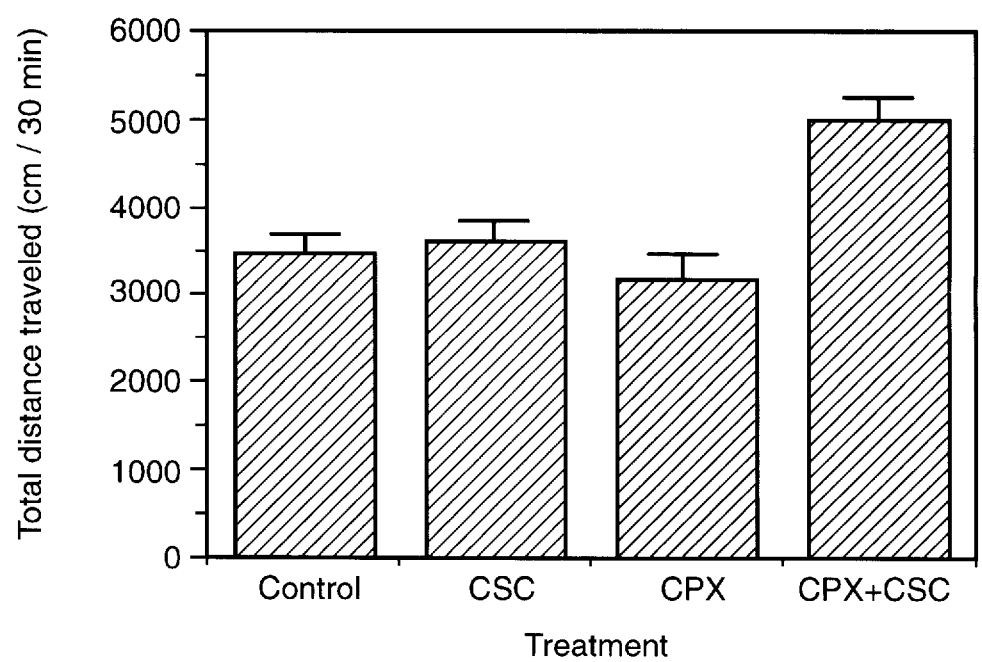
FIG. 12 is a bar graph of total distance traveled (cm/30 min) versus the treatment methods of control, CSC, 8-cyclopentyl-1,3-dipropyl-xanthine (CPX), and CPX+CSC, which shows the synergism of CPX and CSC in stimulating locomotor activity in mice.

The $A_1$-selective antagonist CPX was administered alone and in combination with CSC is shown in FIG. 12, which is a bar graph of total distance traveled (cm/30 min) versus treatment method of control, CSC, CPX, and CPX together with CSC, which shows the synergism of an $A_1$ selective antagonist, namely CPX (0.25 mg/kg, i.p.), and an $A_2$ selective antagonist, namely CSC (1.0 mg/kg, i.p.) in stimulating locomotor activity in mice (n=9–19; * represents a p value of less than 0.001 versus CSC alone). CPX alone resulted in a total distance traveled of 3035±330 cm/30 min (n=14) (i.e., a minimal depressant effect on locomotor activity compared to control). CSC alone (1 mg/kg) had no significant effect on locomotor activity, with a total distance traveled of 3550±230 cm/30 min (n=19). However, the combination of the two antagonists, each at a subthreshold dose, stimulated locomotor activity by 37% (p<0.001) over CSC alone (total distance traveled of 4861±243 cm/30 min, n=9), suggesting a synergism of $A_1$- and $A_2$-antagonist effects in the CNS. Following coadministration, the average distance per move was increased by approximately 30%, and clockwise and anti-clockwise rotations were increased in the range of 30–60% (data not shown).

Since at the highest dose administered there was essentially no effect on the locomotor depression elicited by CHA, CSC is a functionally specific antagonist at $A_{2a}$ versus $A_1$ receptors in mice in vivo.

Selective $A_1$ and $A_{2a}$ antagonists alone are either non-stimulatory or weakly stimulatory in locomotor activity (Table VI), but the combination (as shown for subthreshold doses of CSC and CPX) causes substantial stimulation (FIG. 12). An increase in rotational movement, seen with the combination of $A_1$ and $A_{2a}$ antagonists, is also observed with maximal stimulant doses of caffeine (unpublished results). This suggests the possibility that enhancement of dopaminergic action by blocking both presynaptic ($A_1$) and postsynaptic ($A_{2a}$) mechanisms might be required for substantial locomotor stimulation by xanthines. The pronounced enhancement of locomotor activity by non-selective xanthines (Table VI), such as caffeine and theophylline (Snyder et al., *PNAS USA*, 78, 3260–3264 (1981); Nikodijevic et al., 1991, supra), is consistent with this view. The moderate, but transient, locomotor stimulation by CPT (8-cyclopentyltheophylline) may result from its non-selectivity in vivo at high doses (Table VI). The synergistic behavioral depressant effects of $A_1$ agonists in combination with $A_2$ agonists (Nikodijevic et al., 1991, suPra) is also consonant with this view.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. An 8-styryl xanthine having the formula:

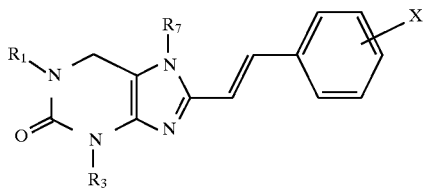

wherein $R_1$, $R_3$, and $R_7$ are methyl and X is one to three substituents, which may be the same or different, selected from the group consisting of amino, $C_1-C_4$ alkylcarbonylamino, succinylamino, halo, amino $C_1-C_4$ alkyloxy, amino $C_1-C_4$ alkenyloxy, isothiocyanato, and diazonium tetrafluoroborate.

2. The 8-styryl xanthine of claim 1, wherein X is at a position selected from the group consisting of 3, 4, 5, and combinations thereof.

3. The 8-styryl xanthine of claim 2, wherein X is selected from the group consisting of 3-amino, 3-$C_1-C_4$ alkylcarbonylamino, 3-succinylamino, 3-halo, 3,5-dihalo, 3-isothiocyanato, and 3-diazonium tetrafluoroborate.

4. The 8-styryl xanthine of claim 1, wherein said $C_1-C_4$ alkylcarbonylamino is acetylamino, said halo is bromo, chloro, fluoro, or iodo, said amino $C_1-C_4$ alkyloxy is 4-amino-butyloxy, and said amino $C_1-C_4$ alkenyloxy is 4-amino-2-trans-buten-1-oxy.

5. The 8-styryl xanthine of claim 4, wherein X is at a position selected from the group consisting of 3, 4, 5, and combinations thereof.

6. The 8-styryl xanthine of claim 5, wherein X is selected from the group consisting of 3-amino, 3-iodo, and 3-diazonium tetrafluoroborate.

7. The 8-styryl xanthine of claim 5, wherein X is selected from the group consisting of 3-acetylamino, 3-succinylamino, 3-fluoro, 3-chloro, 3,5-difluoro, and 3-isothiocyanato.

8. An 8-styryl xanthine having the formula:

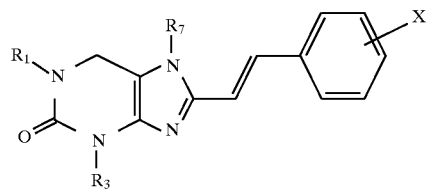

wherein $R_1$ and $R_3$ are propyl, $R_7$ is methyl, and X is one or two amino substituents.

9. An 8-substituted xanthine having the formula:

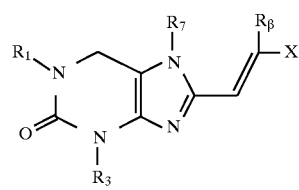

wherein $R_1$, $R_3$, and $R_7$ are methyl, $R_\beta$ is hydrogen or methyl, and X is selected from the group consisting of R, C(=O)OR, and C(=O)NH—R, wherein R is a $C_1-C_6$ alkyl.

10. The 8-substituted xanthine of claim 9, wherein X is n-propyl.

11. The compound of claim 9, wherein said compound is selected from the group consisting of 8-(trans-2-tert-butoxycarbonylvinyl)-1,3,7-trimethylxanthine, and 8-(2-n-propylvinyl)-1,3,7-trimethylxanthine.

12. A compound selected from the group consisting of 1,3,7-trimethyl-8-(3-(di-(tert-butyloxycarbonyl)amino) styryl)xanthine, 1,3,7-trimethyl-8-(4-((tert-butyloxycarbonyl) aminobutyloxy)styryl)xanthine, 1,3,7-trimethyl-8-(3-tert-butyloxycarbonyl aminostyryl)xanthine, and 1,3,7-trimethyl-8-(3,5-dimethoxy-4-(4-amino-butyloxy)styryl)xanthine.

13. A pharmaceutical composition comprising a pharmaceutically acceptable carrier and at least one of the compounds of claim 1.

14. A pharmaceutical composition comprising a pharmaceutically acceptable carrier and at least one of the compounds of claim 6.

15. A pharmaceutical composition comprising a pharmaceutically acceptable carrier and at least one of the compounds of claim 7.

16. A pharmaceutical composition comprising a pharmaceutically acceptable carrier and at least one of the compounds of claim 9.

17. A pharmaceutical composition comprising a pharmaceutically acceptable carrier and at least one of the compounds of claim 10.

18. The 8-substituted xanthine of claim 9, wherein X is selected from the group consisting of C(=O)OC(CH$_3$)$_3$ and C(=O)NH-alkyl.

19. A pharmaceutical composition comprising a pharmaceutically acceptable carrier and at least one of the compounds of claim 18.

20. The 8-styryl xanthine of claim 1, wherein X is a member selected from the group consisting of 3-halo, 3-amino, and 3-acetylamino.

21. An 8-styryl xanthine having the formula:

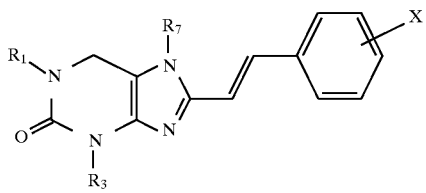

wherein $R_1$, $R_3$, and $R_7$ are methyl and X is two substituents, one of which is methoxy and the other of which is selected from the group consisting of amino, $C_1$–$C_4$ alkylcarbonylamino, succinylamino, halo, amino $C_1$–$C_4$ alkyloxy, amino $C_1$–$C_4$ alkenyloxy, isothiocyanato, and diazonium tetrafluoroborate.

22. The compound of claim 1, wherein said compound is selected from the group consisting of 1,3,7-trimethyl-8-(3-aminostyryl)xanthine, 1,3,7-trimethyl-8-(3-acetylaminostyryl)xanthine, and 1,3,7-trimethyl-8-(3-succinylaminostyryl)xanthine.

23. A compound selected from the group consisting of 1,3,7-trimethyl-8-(3,5-dialkyloxy-4-(amino-$C_1$–$C_4$-alkyloxy)styryl)xanthine and 1,3,7-trimethyl-8-(3,5-dialkyloxy-4-(amino-$C_1$–$C_4$-alkenyloxy)styryl)xanthine.

24. A pharmaceutical composition comprising a pharmaceutically acceptable carrier and at least one of the compounds of claim 21.

25. A pharmaceutical composition comprising a pharmaceutically acceptable carrier and at least one of the compounds of claim 22.

26. A pharmaceutical composition comprising a pharmaceutically acceptable carrier and the compound of claim 12.

27. A pharmaceutical composition comprising a pharmaceutically acceptable carrier and at least one of the compounds of claim 23.

28. The 8-styryl xanthine of claim 20 where X is 3-chloro.

* * * * *